United States Patent
Lavallo et al.

(10) Patent No.: US 9,994,595 B2
(45) Date of Patent: Jun. 12, 2018

(54) CATALYST AND BATTERY COMPONENTS DERIVED FROM CONDENSATION REACTIONS WITH CARBA-CLOSO-DODECABORATE AMINES

(71) Applicant: THE REGENTS OF THE UNVERSITY OF CALIFORNIA, Oakland, CA (US)

(72) Inventors: Vincent Lavallo, Oakland, CA (US); Ahmad El Hellani, Oakland, CA (US); Allen Chan, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days. days.

(21) Appl. No.: 15/126,245

(22) PCT Filed: Mar. 16, 2015

(86) PCT No.: PCT/US2015/020827
§ 371 (c)(1),
(2) Date: Sep. 14, 2016

(87) PCT Pub. No.: WO2015/139060
PCT Pub. Date: Sep. 17, 2015

(65) Prior Publication Data
US 2017/0084954 A1  Mar. 23, 2017

Related U.S. Application Data

(60) Provisional application No. 61/953,623, filed on Mar. 14, 2014.

(51) Int. Cl.
| | | |
|---|---|---|
| C07F 5/02 | (2006.01) |
| C07F 15/00 | (2006.01) |
| C07F 15/04 | (2006.01) |
| C07F 1/00 | (2006.01) |
| C07F 1/08 | (2006.01) |
| C07F 1/10 | (2006.01) |
| C07F 3/02 | (2006.01) |
| B01J 31/22 | (2006.01) |
| B01J 31/24 | (2006.01) |
| C07C 2/76 | (2006.01) |
| C07C 5/333 | (2006.01) |
| H01M 10/0565 | (2010.01) |
| H01M 10/0568 | (2010.01) |

(52) U.S. Cl.
CPC ........... *C07F 5/027* (2013.01); *B01J 31/2265* (2013.01); *B01J 31/2295* (2013.01); *B01J 31/2404* (2013.01); *C07C 2/76* (2013.01); *C07C 5/3335* (2013.01); *C07C 5/3337* (2013.01); *C07F 1/00* (2013.01); *C07F 1/08* (2013.01); *C07F 1/10* (2013.01); *C07F 3/02* (2013.01); *C07F 5/02* (2013.01); *C07F 15/006* (2013.01); *C07F 15/0033* (2013.01); *C07F 15/04* (2013.01); *C07F 15/045* (2013.01); *H01M 10/0565* (2013.01); *H01M 10/0568* (2013.01); *B01J 2231/46* (2013.01); *B01J 2231/766* (2013.01); *B01J 2531/16* (2013.01); *B01J 2531/17* (2013.01); *B01J 2531/824* (2013.01); *B01J 2531/827* (2013.01); *B01J 2531/847* (2013.01); *C07C 2531/22* (2013.01); *H01M 2300/0025* (2013.01); *H01M 2300/0085* (2013.01)

(58) Field of Classification Search
CPC ........................................................ C07F 5/027
See application file for complete search history.

(56) References Cited

PUBLICATIONS

Douglass et al. Inorg. Chem. 1998, 37, 6361-6365.*
Vyakaranam et al. J. Am. Chem. Soc. 2007, 129, 4172-4174.*
Asay et al. Chem. Commun. 2015, 51, 5359.*
Pecyna et al. Inorg. Chem. 2014, 53, 12617-12626.*
Bertrand G. et al., "Stable Cyclic Carbenes and Related Species beyond Diaminocarbenes," Angewandte Chemie Int, Ed. 2010, 49, pp. 8810-8849.
Diez-Gonzalez Silvia et al., "N-Heterocyclic Carbenes in Late Transition Metal Catalysis," Chemical Review, (Received Feb. 24, 2009), 2009, vol. 109, No. 8, pp. 3612-3676.
Arnold Polly L et al., "F-Block N-Heterocyclic Carbene Complexes," Chemical Review, (Received Nov. 13, 2008), 2009, 109, pp. 3599-3611.
Vignolle Joan et al., "Stable Noncyclic Singlet Carbenes," Chemical Review, (Received Dec. 17, 2008), 2009, 109, pp. 3333-3384.
Lin Joseph C.Y. et al., "Coinage Metal—N-Heterocyclic Carbene Complexes," Chemical review, (Received Nov. 10, 2008), 2009, 109, pp. 3561-3598.
Hahn Ekkehardt F. et al., "Heterocyclic Carbenes: Synthesis and Coordination Chemistry," Angewandte Chemie Int. Ed. 2008, 47, pp. 3122-3172.

(Continued)

*Primary Examiner* — Matthew P Coughlin
(74) *Attorney, Agent, or Firm* — Mintz Levin Cohn Ferris Glovsky Popeo P.C.

(57) ABSTRACT

Described herein is the fusion of two families of unique carbon-containing molecules that readily disregard the tendency of carbon to form four chemical bonds, namely N-heterocyclic carbenes (NHCs) and carborane anions. Deprotonation of an anionic imidazolium salt with lithium diisopropylamide at room temperature leads to a mixture of lithium complexes of C-2 and C-5 dianionic NHC constitutional isomers as well as a trianionic (C-2, C-5) adduct. Judicious choice of the base and reaction conditions allows for the selective formation of all three stable polyanionic carbenes. In solution, the so-called abnormal C-5 NHC lithium complex slowly isomerizes to the normal C-2 NHC, and the process can be proton catalyzed by the addition of the anionic imidazolium salt. These results indicate that the combination of two unusual forms of carbon atoms can lead to unexpected chemical behavior, and that this strategy paves the way for the development of a broad new generation of NHC ligands for catalysis.

23 Claims, 38 Drawing Sheets

(56) References Cited

PUBLICATIONS

Igau Alain et al., "Analogous α,α-Bis-Carbenoid Triply Bonded Species: Synthesis of a Stable $\Lambda^3$-Phosphinocarbene-$\Lambda^5$Phosphaacetylene," J. Am. Chem. Soc., (Received 29, 1988),1988, vol. 110, No. 19, pp. 6463-6466.

Arduengo Anthony J. III et al. "A Stable Crystalline Carbene," J. Am. Soc., (Received Sep. 26, 1990), 1991, vol. 113, No. 1., pp. 361-363.

Schaper Lars-Ame et al., "Synthesis and Application of Water-Soluble NHC Transition-Metal Complexes," Angewandte Chemie, Int. Ed., (Received Jun. 29, 2012),2013, 52, pp. 270-289.

Xiong Yun et al., "A Cyclic Silylone ("Siladicarbene") with an Electron-Rich Silicon(0)Atom," Angewandte Chemie Int. Ed. 2013, 52, pp. 7147-7150.

Droge Thomas et al., "The Measure of All Rings—N-Heterocyclic Carbenes," Angewandte Chemie, 2010, Int, Ed,2010, 49, pp. 6940-6952.

Samojłowicz Cezary et al., "Ruthenium-Based Olefin Metathesis Catalysts Bearing N-Heterocyclic Carbene Ligands," Chemical Review, (Received Nov. 14, 2008), 2009, 109, pp. 3708-3742.

Martin Caleb D. et al.,"Carbene-stabilized main group radicals and radical ions," Chem. Sci., (Received Apr. 30, 2013), 2013, 4, pp. 3020-3030.

Wang Yuzhong et al., "Carbene-stabilized main group diatomic allotropes," Dalton Transactions, (Received Jun. 20, 2011), 2012, 41, pp. 337-345.

Mondal Kartik Chandra et al., "Formation of Trichlorosilyl-Substituted Carbon-Centered Stable Radicals through the Use of π-Accepting Carbenes," Angewandte Chemie, 2013, 125, pp. 12020-12023.

Mondal Kartik Chandra et al., "Formation of Trichlorosilyl-Substituted Carbon-Centered Stable Radicals through the Use of π-Accepting Carbenes," Angewandte Chemie, 2013, 125, pp. 11804-11807.

Grossmann Andre et al., "N-Heterocyclic Carbene Catalyzed Domino Reactions," Angewandte Chemie, Int, Ed, 2012, 51, pp. 314-325.

Denmark Scott E. et al., "Lewis Base Catalysis in Organic Synthesis," Angewandte Chemie, Int, Ed, 2008, 47, pp. 1560-1638.

Marion Nicolas et al., "N-Heterocyclic Carbenes as Organocatalysts," Angewandte Chemie, Int, Ed, 2007, 46, pp. 2988-3000.

Grundemann Stephan et al., "Abnormal binding in a carbene complex formed from an imidazolium salt and a metal hydride complex,", Chem. Commun., (Received Aug. 24, 2001), 2001, pp. 2274-2275.

Crabtree Robert H., "Abnormal, mesoionic and remote N-heterocyclic carbene complexes," Coordination Chemistry Reviews 257, 2013, pp. 755-766.

Kruger Anneke et al., "Non-classical N-Heterocyclic Carbene Complexes,"Chem Sci., 2011, (Published on Nov. 26, 2010), pp. 134-165.

Schuster Oliver et al., "Beyond Conventional N-Heterocyclic Carbenes: Abnormal, Remote, and Other Classes of NHC Ligands with Reduced Heteroatom Stabilization," Chem. Reb. 2009, vol. 109, No. 8, pp. 3445-3478.

Kruger Anneke et al., "Abnormal N-heterocyclic Carbenes: More than Just Exceptionally Strong Donor Ligands," Aust. J. Chem., 2011, 64, pp. 1113-1117.

Arnold Polly L. et al., "Abnormal N-heterocyclic carbenes," Coordination Chemistry Review, (Received May 1, 2006), 2007, 251, pp. 596-609.

Yang Liangru et al., "Rhodium(III) Complexes Containing C4-Bound N-Heterocyclic Carbenes: Synthesis, Coordination Chemistry, and Catalytic Activity in Transfer Hydrogenation,", Organometallics, (Received Feb. 7, 2008), 2008, 27, pp. 3161-3171.

Heckenroth Marion et al., "Neutral Ligands with Exceptional Donor Ability for Palladium-Catalyzed Alkene Hydrogenation," Angewandte Chemie, 2007, 119, pp. 6409-6412.

Heckenroth Marion et al., "Neutral Ligands with Exceptional Donor Ability for Palladium-Catalyzed Alkene Hydrogenation," Angewandte Chemie, 2007, 46, pp. 6293-6296.

Aldeco-Perez Eugenia et al., "Isolation of a C5-Deprotonated Imidazolium, a Crystalline "Abnormal" N-Heterocyclic Carbene," Science, vol. 326, Oct. 23, 2009, pp. 556-559.

Albrecht Martin, "Carbenes in Action," Science, vol. 326, Oct. 23, 2009, pp. 532-533.

Wang Yuzhong et al., "A Viable Anionic N-Heterocyclic Dicarbene," J. Am. Chem. Soc., (Received Jul. 26, 2010), 2010, vol. 132, No. 41, pp. 14370-14372.

Kruger Anneke et al., "Chelating C4-Bound Imidazolylidene Complexes through Oxidative Addition of Imidazolium Salts to Palladium(0)," Eur. J. Inog. Chem. 2012, pp. 1394-1402.

Mas-Marza Elena et al., "A Versatile Class of Ligands for the Preparation of Discrete Molecules of Homo-and Hetero-Binuclear Complexes for Improved Catalytic Applications," Angewandte Chemie, 2007, 119, pp. 3803-3805.

Mas-Marza Elena et al., "A Versatile Class of Ligands for the Preparation of Discrete Molecules of Homo-and Hetero-Binuclear Complexes for Improved Catalytic Applications," Angewandte Chemie, 2007, 46, pp. 3729-3731.

Douvris Christors et al., "Chemistry of the Carba-closo-dodecaborate(−) Anion, CB11H12-," Chem. Rev. 2013, 113, pp. 179-233.

Spokoyny Alexander M., "New ligand platforms featuring boron-rich clusters as organomimetic substituents," Pure Appl. Chem., 2013, vol. 85, No. 5, pp. 903-919.

Brusselle Damien et al., "Lyotropic Lamellar Phase Formed from Monolayered θ-Shaped Carborane-Cage Amphiphiles, "Angewandte Chemie, 2013, 125, pp. 12336-12340.

Brusselle Damien et al., "Lyotropic Lamellar Phase Formed from Monolayered θ-Shaped Carborane-Cage Amphiphiles, "Angewandte Chemie, 2013, 52, pp. 12114-12118.

Olid David et al., "Methods to produce B—C, B—P, B—N and B—S bonds in boron clusters," Chem. Soc. Reb.,(Received Oct. 26 , 2012), 2013, 42, pp. 3318-3336.

Scholz Matthias et al., "Carbaboranes as Pharmacophores: Properties, Synthesis, and Application Strategies," Chem. Rev. 2011, 111, pp. 7035-7062.

Roesky H. W. et al., "1-$B_9H_9CH^-$ and $B_{11}H_{11}CH^-$," Journal of the American Chemical Society, (Received Dec. 19, 1966),Published Mar. 1, 1967, 89:5, pp. 1274-1275.

Reed Christopher A., "$H^+$, $CH_3^+$, and $R_3Si^+$Carborane Reagents: When Triflates Fail," Accounts of Chemical Research, (Received May 29, 2009), Jan. 2010, vol. 43, No. 1, pp. 121-128.

Boere Rene T. et al., "Quantum-Chemical and Electrochemical Investigation of the Electrochemical Windows of Halogenated Carborate Anions," Chem. Eur. J. 2013, 19, pp. 1784-1795.

Bolli Christoph et al., "[NO][$HCB_{11}Cl_{11}$]—Synthesis, Characterization, Crystal Structure, and Reaction with $P_4$," Z. Anorg. Allg. Chem., (Received Oct. 11, 2011), 2012, pp. 559-564.

Ramirez-Contreras Rodrigo et al., "Synthesis of a Silylium Zwitterion," Angewandte Chemie, 2013, 125, pp. 10503-10505.

Ramirez-Contreras Rodrigo et al., "Synthesis of a Silylium Zwitterion," Angewandte Chemie, 2013, 52, pp. 10313-10315.

Himmelspach Alexander et al., "Tetrahedral Gold(I) Clusters with Carba-closo-dodecaboranylethynido Ligands: [{12-$(R_3PAu)_2C\_C\equiv closo-1-CB_{11}H_{11}$}$_2$]," Angewandte Chemie, Int. Ed. 2011, 50, pp. 2628-2631.

Douvris Christos et al., "Hydrodefluorination and Other Hydrodehalogenation of Aliphatic Carbon-Halogen Bonds Using Silylium Catalysis," J. America Chemical Society, (Received Jan. 22, 2010), 2010, 132, pp. 4946-4953.

Douvris Christos et al., "Hydrodefluorination of Perfluoroalkyl Groups Using Silylium-Carborane catalysts," Science, Aug. 29, 2008, vol. 321, pp. 1188-1190.

Lavallo Vincent et al., "Perhalogenated Carba-closo-dodecaborate Anions as Ligand Substituents: Applications in Gold Catalysis," Angewandte Chemie, 2013, 125, pp. 3254-3258.

(56) References Cited

OTHER PUBLICATIONS

Lavallo Vincent et al., "Perhalogenated Carba-closo-dodecaborate Anions as Ligand Substituents: Applications in Gold Catalysis," Angewandte Chemie, 2013, 52, pp. 3172-3176.

El-Hellani Ahmad et al., "Structure and Bonding of a Zwitterionic Iridium Complex Supported by a Phosphine with the Parent Carba-closo-dodecaborate $CB_{11}H_{11}$—Ligand Substituent," Organometallics, (Received Oct. 11, 2013), 2013, 32, pp. 6887-6890.

Kolychev Eugene L. et al., "Iridium(I) Complexes with Anionic N-Heterocyclic Carbene Ligands as Catalysts for the Hydrogenation of Alkenes in Nonpolar Media," J. America Chemical Society, (Received Jul. 2, 2013), 2013, 135, pp. 12448-12459.

Kronig Sabrina et al., "Anionic N-Heterocyclic Carbenes That Contain a Weakly Coordinating Borate Moiety," Angewandte Chemie, 2012, 124, pp. 3294-3298.

Kronig Sabrina et al., "Anionic N-Heterocyclic Carbenes That Contain a Weakly Coordinating Borate Moiety," Angewandte Chemie, 2012, 51, pp. 3240-3244.

Jelnek Tomas et al., "Chemistry of Compounds With the I-CARBA-closo-ODECABORANE(12) Framework," Collection Czechoslovak Chem. Commun., (Received Oct. 22, 1984), 1986, vol. 51, pp. 819-829.

Wright James H. II et al., "Click-Like Reactions with the Inert $HCB_{11}Cl_{11}$—Anion Lead to Carborane-Fused Heterocycles with Unusual Aromatic Character," Inorganic Chemistry, (Received Mar. 29, 2013), 2013, 52, pp. 6223-6229.

Asay Matthew et al., "Isolation of a Carborane-Fused Triazole Radical Anion," Angewandte Chemie, 2013, 125, pp. 11774-11777.

Asay Matthew et al., "Isolation of a Carborane-Fused Triazole Radical Anion," Angewandte Chemie, 2013, 52, pp. 11560-11563.

Boyd Lynn A. et al., "EXO-π-bonding to an *ortho*-carborane hypercarbon atom:systematic icosahedral cage distortions reflected in the structures of the fluoro-, hydroxy- and amino-carboranes, $1-X-2-Ph-1,2-C_2B_{10}H_{10}$ (X = F, OH or $NH_2$) and related anions," Dalton Trans., (Received Apr. 28, 2004), 2004, pp. 2786-2799.

Weller Andrew S. et al., "Rhodium cyclooctadiene complexes of the weakly co-ordinating carborane anion [$closo$-$CB_{11}H_{12}$]. Isolation and crystal structures of $[(COD)Rh(\eta^2-CB_{11}H_{12})]$ and $[(COD)Rh(THF)_2][CB_{11}H_{12}]$," Journal of Organometallic Chemistry 614-615, (Received Mar. 27, 2000), 2002, ages 113-119.

Vinas Clara et al., "Modulation of Agostic B-H→Ru Bonds in *exo*-Monophosphino-7,8-Dicarba-*nido*-undecaborate Derivatives," Organometallics, vol. 15, No. 18, (Received Nov. 22, 1995), 1996, pp. 3850-3858.

Teixidor Francesc et al., "Modulation of the B(3)-H→Ru Distances in 7,8-Dicarba-nido-undecaborat Derivatives," Organometallics, (Received Jan. 28, 1994), 1994, 13, pp. 2751-2760.

Teixidor Francesc et al., "A Novel B-H→RU Agostic Bond. Crystal Structure of $[RuCl\{7,8-\mu-S(CH_2CH_2)S-C_2B_9H_{10}\}(PPh_3)^- Me_2CO$," Chem. SOC., Chem. Commun., (Received Jun. 23, 1992), 1992, pp. 1281-1282.

Mendoza-Espinosa Daniel et al., "Synthesis of 4- and 4,5-Functionalized Imidazol-2-ylidenes from a Single 4,5-Unsubstituted Imidazol-2-ylidene,", J. Am. Chem. Soc., vol. 132, No. 21, (Received Mar. 29, 2010), 2010, pp. 7264-7265.

Day Benjamin M. et al., "Nomml-to-Abnormal Rearrangement and NHC Activation in Three-Coordinate Iron(II) Carbene Complexes," , J. Am. Chem. Soc., 135, (Received Aug. 19, 2013), 2013, pp. 13338-13341.

Planas Jose Giner et al., "Self-Assembly of Mercaptane-Metallacarborane Complexes by an Unconventional Cooperative Effect: A C-H•••S-H•••H-B Hydrogen/Dihydrogen Bond Interaction," J. Am. Chem. Soc., 127, (Received Aug. 1, 2005), 2005, pp. 15976-15982.

Gossage Robert A. et al., "Hetero-Aggregate Compounds of Aryl and Alkyl Lithium Reagents: A Structurally Intriguing Aspect of Organolithium Chemistry," Angewandte Chemie, Int. Ed. 2005, 44, pp. 1448-1454.

Noorden Richard Van, "A Better Battery Chemists are reinventing rechargeable cells to drive down costs and boost capacity," Nature, vol. 507, Mar. 6, 2014, pp. 26-28.

Mohtadi Rana et al., "Magnesium batteries: Current state of the art, issues and future perspectives," Beilstein J. Nanotechnol. (Received Mar. 18, 2014), 2014, 5, pp. 1291-1311.

Yoo Hyun Deog et al., "Mg rechargeable batteries: an on-going challenge," Energy Environ. Sci., (Received Mar. 13, 2013), 2013, 6, pp. 2265-2279.

Muldoon John et al., "Electrolyte roadblocks to a magnesium rechargeable battery," Energy Environ. Sci., (Received Oct. 31, 2011), 2012, 5, pp. 5941-5950.

Carter Tyler J. et al," Boron Clusters as Highly Stable Magnesium-Battery Electrolytes," Angewandte Chemie, Int. Ed., (Received Nov. 27, 2013), 2014, 53, pp. 3173-3177.

Schmidbaur Hubert et al., "Silver-free Gold(I) Catalysts for Organic Transformations," B:J. Chem. Sci., (Received Feb. 16, 2011), 2011, 66, pp. 329-350.

Gomez-Suarez Adrian et al., "Dinuclear Gold Catalysis: Are Two Gold Centers Better than One ?," Angewandte Chemie, Int. Ed., (Received May 9, 2012), 2012, 51, pp. 8156-8159.

Loh Charles C.J. et al., "Merging Organocatalysis and Gold Catalysis—A Critical Evaluation of the Underlying Concepts," Chem. Eur. J., 2012, 18, pp. 10212-10225.

Garayalde David et al., "Gold-Containing and Gold-Generated 1,n-Dipoles as Useful Platforms toward Cycloadditions and Cyclizations," American Chemical Society Catal. (Received Jan. 19, 2012), 2012, 2, pp. 1462-1479.

Wang Dawei et al., ""Silver Effect" in Gold(I) Catalysis: An Overlooked Important Factor," J. Am. Chem. Soc., (Received Apr. 22, 2012), 2012, 134, pp. 9012-9019.

Lu Bei-Li et al., "Strained small rings in gold-catalyzed rapid chemical transformations," Chem. Soc. Rev., (Received Nov. 1, 2011), 2012, 41, pp. 3318-3339.

Liu Le-Ping et al., "Recent advances in the isolation and reactivity of organogold complexes," Chem. Soc. Rev., (Received Nov. 28, 2011), 2012, 41, pp. 3129-3139.

Rudolph Matthias et al., "Gold catalysis in total synthesis—an update, " Chem. Soc. Rev., (Received Oct. 6, 2011), 2012, 41, pp. 2448-2462.

Pina Cristina Della et al., "Update on selective oAdation using gold, " Chem. Soc. Rev., (Received Apr. 1, 2011), 2012, 41, pp. 350-369.

Rudolph Matthias et al., "Heterocycles from gold catalysis," Chem. Commun., (Received Feb. 10, 2011), 2011, 47, pp. 6536-6544.

Bandini Marco, "Gold-catalyzed decorations of arenes and heteroarenes with C—C multiple bonds," Chem. Soc. Rev., (Received Jul. 14, 2010), 2011, 40, pp. 1358-1367.

Malacria Max et al., "Activation of Allenes by Gold Complexes: A Theoretical Standpoint," Top Curr Chem, Published : Feb. 3, 2011, 302, pp. 157-182.

Hashmi A. Stephen K., "Homogeneous Gold Catalysis Beyond Assumptions and Proposals—Characterized Intermediates," Angewandte Chemie, Int. Ed., (Received Dec. 15, 2009), 2010, 49, pp. 5232-5241.

Gorin David J. et al., "Ligand Effects in Homogeneous Au Catalysis," Chemical Review, (Received Feb. 13, 2008), 2008, 108, pp. 3351-3378.

Klinkenberg Jessica L. et al., "Catalytic Organometallic Reactions of Ammonia," Angewandte Chemie, Int. Ed., (Received Apr. 20, 2010), 2011, 50, pp. 86-95.

Krossing Ingo, "Gold(I)-1,3-Diene Complexes: Connecting Structure, Bonding, and Reactivity," Angewandte Chemie, Int. Ed., (Received Aug. 11, 2011), 2011, 50, pp. 11576-11578.

Muller Thomas E. et al., "Hydroamination: Direct Addition of Amines to Alkenes and Alkynes," Chemical Review, (Received Jan. 22, 2008), 2008, vol. 108, No. 9, pp. 3795-3892.

Widenhoefer Ross A. et al., "Gold-Catalyzed Hydroamination of C—C Multiple Bonds," Eur. J. Org. Chem., (Received May 5, 2006), 2006, pp. 4555-4563.

Fleischer Steffer et al., "Consecutive Intermolecular Reductive Hydroamination: Cooperative Transition-Metal and Chiral Bronsted Acid Catalysis," Chem. Eur. J., (Received Jan. 11, 2012), 2012, 18, pp. 9005-9010.

(56) References Cited

OTHER PUBLICATIONS

Alvarado Edwin et al., "N-Heterocyclic Carbenes and Imidazole-2-thiones as Ligands for the Gold(I)-Catalysed Hydroamination of Phenylacetylene," Chem. Eur. J., (Received Apr. 26, 2012), 2012, 18, pp. 12112-12121.
Kinjo Rei et al., "Gold-Catalyzed Hydroamination of Alkynes and Allenes with Parent Hydrazine," Angewandte Chemie, (Received Jan. 28, 2011), 2011, 123, pp. 5674-5677.
Kinjo Rei et al., "Gold-Catalyzed Hydroamination of Alkynes and Allenes with Parent Hydrazine," Angewandte Chemie, (Received Jan. 28, 2011), 2011, 50, pp. 5560-5563.
Butler Kristina L. et al. "Gold(I)-Catalyzed Stereoconvergent, Intermolecular Enantioselective Hydroamination of Allenes," Angewandte Chemie, (Received Feb. 28, 2012), 2012, 124, pp. 5265-5268.
Butler Kristina L. et al. "Gold(I)-Catalyzed Stereoconvergent, Intermolecular Enantioselective Hydroamination of Allenes," Angewandte Chemie, (Received Feb. 28, 2012), 2012, 51, pp. 5175-5178.
Hesp Kevin D. et al., "Stereo- and Regioselective Gold-Catalyzed Hydroamination of Internal Alkynes with Dialkylamines," J. Am. Chem. Soc., (Received Oct. 13, 2010), 2010, vol. 132, No. 51, pp. 18026-18029.
Leyva-Perez Antonio et al., "Gold(I) Catalyzes the Intermolecular Hydroamination of Alkynes with Imines and Produces α,α',N-Triarylbisenamines: Studies on Their Use As Intermediates in Synthesis," J. Org. Chem., (Received Aug. 26, 2010), 2010, vol. 75, No. 22, pp. 7769-7780.
Lavallo Vincent et al., "Homogeneous Catalytic Hydroamination of Alkynes and Allenes with Ammonia," Angewandte Chemie, (Received Mar. 8, 2008), 2008, 120, pp. 5302-5306.
Lavallo Vincent et al., "Homogeneous Catalytic Hydroamination of Alkynes and Allenes with Ammonia," Angewandte Chemie, (Received Mar. 8, 2008), 2008, 47, pp. 5224-5228.
Mizushima Eiichiro et al., "Au(I)-Catalyzed Highly Efficient Intermolecular Hydroamination of Alkynes," Organic Letters, (Received Jul. 16, 2003), 2003, vol. 5, No. 18, pp. 3349-3352.
Aldeco-Perez Eugenia et al., "Isolation of a C5-Deprotonated Imidazolium, a Crystalline "Abnormal" N-Heterocyclic Carbene," Science, Oct. 23, 2009, vol. 326, pp. 556-559.
Bellemin-Laponnaz Stephane et al., "Group 1 and 2 and Early Transition Metal Complexes Bearing N-Heterocyclic Carbene Ligands: Coordination Chemistry, Reactivity, and Applications," Chem. Rev., (Received Apr. 24, 2014), 2014, 114, pp. 8747-8774.
Wang Yuzhong et al., "A Viable Anionic N-Heterocyclic Dicarbene," J. Am. Chem. Soc., (Received Jul. 26, 2010), 2010, 132, pp. 14370-14372.
Etienne Michel et al., "Intramolecular C—C agostic complexes: C—C sigma interactions by another name," Chem. Soc. Rev., (Received Aug. 5, 2013), 2014, 43, pp. 242-259.
Brookhart Maurice et al., "Agostic interactions in transition metal compounds," PNAS, (Received Feb. 8, 2007), Published Apr. 24, 2007, vol. 104, No. 17, pp. 6908-6914.

* cited by examiner

CATALYST AND BATTERY COMPONENTS DERIVED FROM CONDENSATION REACTIONS WITH CARBA-CLOSO-DODECABORATE AMINES

CROSS-REFERENCES TO RELATED APPLICATIONS

The present application claims priority to U.S. Provisional Pat. Appl. No. 61/953,623, filed on Mar. 14, 2014, which application is incorporated herein by reference in its entirety.

FIELD OF THE INVENTION

This patent application discloses catalysts, including but not limited to, fused N-heterocyclic carbenes with carborane anions, as well as methods of making the same, which are useful in the field of catalysis and energy storage.

BACKGROUND OF THE INVENTION

In the last two decades, stable carbene chemistry has been the focus of extensive research.[1] This is largely due to the fact that NHCs, such as the imidazolylidenes 1, have found utility as ligands for catalysts[1b, 1f, 2] and the stabilization of reactive species,[3] as well as catalysts in their own right[4] (FIG. 1). Typically, NHCs 1 are generated from imidazolium cations by deprotonation of the most acidic proton in the C-2 position of the aromatic ring with a strong Brønsted base. In 2001, Crabtree and coworkers[5] made a key discovery that it was possible for imidazolylidenes to adopt a C-5 coordination mode with transition metals. Evidence has since mounted that these "abnormal" NHCs[6] convey distinct and sometimes superior catalytic properties[6f, 6g] to the metals they bind, compared to the normal C-2 isomer. In 2009, Bertrand and coworkers reported that if the acidic proton in the C-2 position of the imidazolium salt precursor was substituted by a hydrocarbon fragment, deprotonation at C-2 could be blocked and abnormal C-5 imidazolylidenes 2 could be isolated as metal free species (FIG. 1).[7] In 2010, Robinson and coworkers reported[8a] that imidazolium salts could be deprotonated at both the C-2 and C-5 positions to afford anionic species 3 that can bind to two metal fragments (FIG. 1).[8]

Another class of molecules that contain an unusual form of carbon, wherein the carbon atom forms 6 chemical bonds with neighboring elements, are icosahedral carboranes.[9] In contrast to carbenes, icosahedral carboranes are extraordinarily stable molecules and certain members of these families, such as the carba-closo-dodecaborate anion $HCB_{11}H_{11}^-$ 4, reported by Knoth in 1967,[10] are legendary for their inert properties (FIG. 1). The carborane anion 4 delocalizes its charge throughout the 12 cage atoms, rendering the cluster and its derivatives very weakly coordinating. The combination of weak coordinative ability and resistance to chemical decomposition explains why these molecules are widely used as counteranions for highly reactive cationic species.[9a, 11]

Over the last decade, numerous technological advances in rechargeable portable devices and electric vehicles have been made. However, innovations that reduce the cost, improve the sustainability, and increase the storage capacity offered by state-of-the-art lithium ion technology has not kept pace with this revolution.[20] The need for advances in battery technology is particularly urgent for the development of practical electric automobiles that can travel significantly further than 300 miles per charge[20] Magnesium-based batteries[21] are attractive energy technologies that have the potential to disrupt the current predominance of lithium ion batteries in the marketplace. In contrast to Li, Mg is less expensive, much more abundant (4% of the earth's crust), more tolerant of air, and does not form hazardous dendrites. The absence of dendrite formation during Mg deposition allows the utilization of pure Mg anodes, which drastically increases the energy storage capacity of the battery. In addition, since Mg is a small divalent atom it can store twice the amount of electrons and thus more energy than Li (theoretical volumetric capacity of metallic Mg=3832 mA h $cm^{-3}$; Li=2062 mA h $cm^{-3}$). However, a key barrier to the development of practical high capacity Mg batteries, is that suitable electolytes are elusive.[21] Electrolytes for Mg batteries must be completely resistant to decomposition at the prefered voltage windows (1-5 v vs $Mg^{0/+2}$). The present invention provides new materials to meet these needs.

BRIEF SUMMARY OF THE INVENTION

In a first aspect, the invention provides compounds according to Formula 1:

(1)

For compounds of Formula 1, $Het^N$ is a heterocycle containing at least one nitrogen atom. In certain embodiments, $Het^N$ is an N-heterocyclic carbene (NHC) moiety or an NHC precursor moiety. $R^B$ is a carba-closo-dodecaborate substituent. $R^W$ is selected from a carba-closo-dodecaborate substituent (i.e., $R^B$), H, halogen, alkyl, aryl, silyl, siloxy, alkoxy, and aryloxy. Each $R^B$, alkyl, aryl, silyl, siloxy, alkoxy, and aryloxy in $R^W$ is optionally substituted with at least one member independently selected from halogen, hydroxyl, hydroxide, alkyl, aryl, silyl, siloxy, alkoxy, aryloxy amino, alkylamino, arylamino, dialkylamino, diarylamino, haloalkyl, thio, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, and nitro. In some embodiments, each of $R^B$, alkyl, aryl, silyl, siloxy, alkoxy, and aryloxy in $R^W$ is optionally substituted with a member independently selected from halogen, hydroxyl, and hydroxide. A is present or absent. When present, A represents one or more cations, each of which is optionally coordinated by 1-8 neutral or anionic ligands.

In compounds of Formula 1, carba-closo-dodecaborate substituent $R^B$ has the structure:

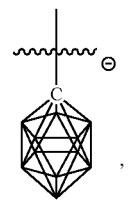

wherein each unlabeled vertex is a boron atom substituted with $R^1$ (i.e., a B—$R^1$ group). Each $R^1$ is independently selected from H, halogen, hydroxyl, hydroxide, alkyl, aryl, silyl, siloxy, alkoxy, aryloxy, amino, alkylamino, arylamino, dialkylamino, diarylamino, haloalkyl, thio, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, and alkoxy. Each alkyl, aryl, silyl, siloxy, alkoxy, and aryloxy in $R^1$ is optionally substituted with at least one member independently selected from halogen, hydroxyl, hydroxide, alkyl, aryl, silyl, siloxy, alkoxy, aryloxy, amino, alkylamino, arylamino, dialkylamino, diarylamino, haloalkyl, thio, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, and nitro. In some embodiments, each $R^1$ is independently selected from H, halogen, alkyl, aryl, silyl, siloxy, alkoxy, and aryloxy. In some embodiments, each alkyl, aryl, silyl, siloxy, alkoxy, and aryloxy in $R^1$ is optionally substituted with a member independently selected from halogen, hydroxyl, and hydroxide.

In some embodiments, the invention provides compounds according to Formula 2:

In a related aspect, the invention provides a compound having the structure selected from Formula (I), Formula (II), Formula (III), Formula (IV), Formula (V), Formula (VI), Formula (VII), Formula (VIII), Formula (IX), Formula (X), Formula (XI), Formula (XII), Formula (XIII), Formula (XIV), Formula (XV), Formula (XVI), and Formula (XVII) as described herein. In certain embodiments, the invention provides a compound having a structure according to Formula (I), Formula (II), or Formula (III):

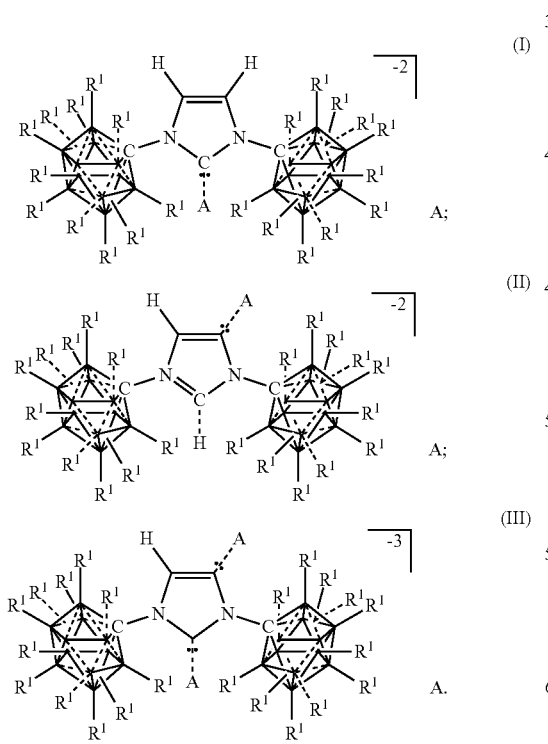

In Formula (I), Formula (II), or Formula (III), each $R^1$ is independently selected from H, halogen, alkyl, aryl, silyl, siloxy, alkoxy, and aryloxy. Each unlabeled vertex bound to $R^1$ represents a boron atom. A is selected from $Li^+$, $Na^+$, $K^+$, $Cs^+$, $HN(alkyl)_3^+$, $N(alkyl)_4^+$, $Mg^{2+}$, $Ca^{2+}$, $Zn^{2+}$, $Al^{3+}$, and $Ag^+$. A can be coordinated by 0-8 solvent molecules.

In another aspect, the invention provides provides a process for preparing a compound according Formula (G):

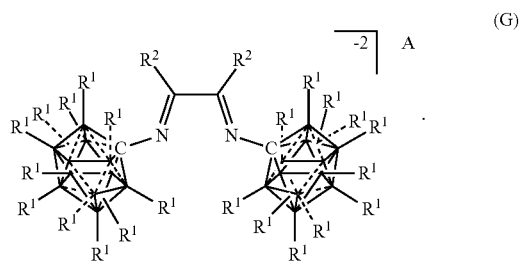

The process for preparing a compound according to Formula (G) includes condensing a compound according to Formula (A)

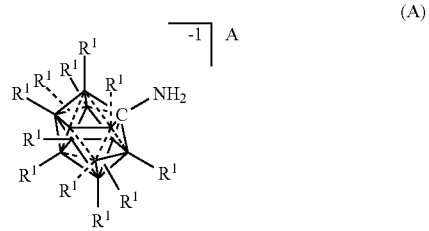

with a compound according to Formula (F):

under conditions sufficient to form the compound of Formula (G).

In processes for preparing a compound according to Formula (G), each unlabeled vertex bonded to $R^1$ represents a boron atom; and A represents one or more cations, each of which is optionally coordinated by 1-8 neutral or anionic ligands. In some embodiments, each $R^1$ and each $R^2$ is independently selected from H, halogen, alkyl, aryl, silyl, siloxy, alkoxy, and aryloxy; each alkyl, aryl, silyl, siloxy, alkoxy, and aryloxy is optionally substituted with a member independently selected from halogen, hydroxyl, and hydroxide;

In another aspect, the invention provides a process for preparing a compound according Formula (H):

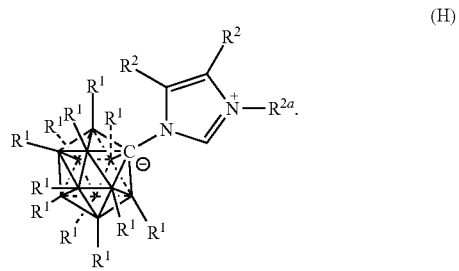

The process for preparing a compound according to Formula (C) includes condensing a compound according to Formula (A):

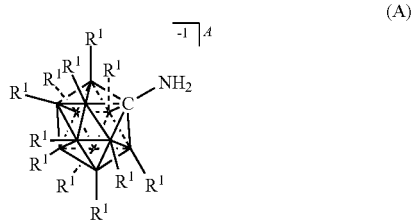

with a compound according to Formula (J):

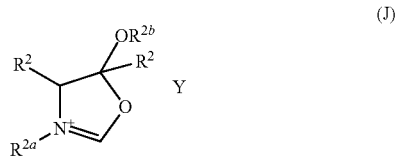

under conditions sufficient to form the compound of Formula (H).

In processes for preparing a compound according to Formula (H), each unlabeled vertex bonded to $R^1$ represents a boron atom; A is a cation which is optionally coordinated by 1-8 neutral or anionic ligands; and Y is an anion. In some embodiments, each $R^1$ and each $R^2$ is independently selected from H, halogen, alkyl, aryl, silyl, siloxy, alkoxy, and aryloxy; wherein each alkyl, aryl, silyl, siloxy, alkoxy, and aryloxy is optionally substituted with a member independently selected from halogen, hydroxyl, and hydroxide; $R^{2a}$ is selected from alkyl and aryl; and $R^{2b}$ is selected from —C(O)-alkyl and —C(O)-aryl.

100%=83% deuterium incorporation at C-5 and a relative ratio of ($83_{C-5}$:$17_{C-2}$) for the 2 deuterated compounds. The formation of a small amount of the C-2 deuterated product by a competitive imidazolium catalyzed isomerization followed by deuteration at C-2 is also observed.

Figure 31:
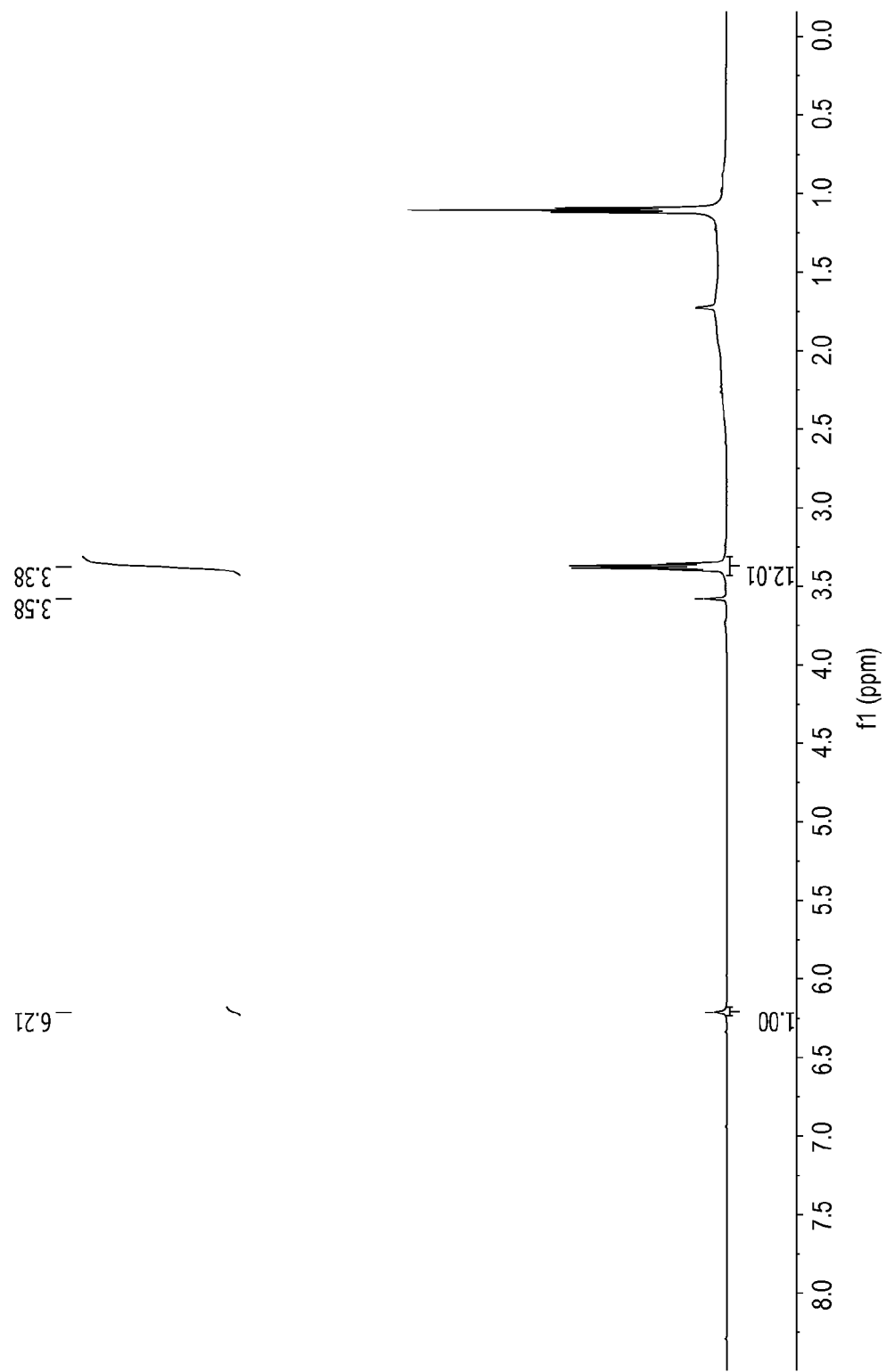

FIG. 31 shows a $^1$H-NMR of 10 in THF-$d_8$, showing three displaced ether molecules.

Figure 32:
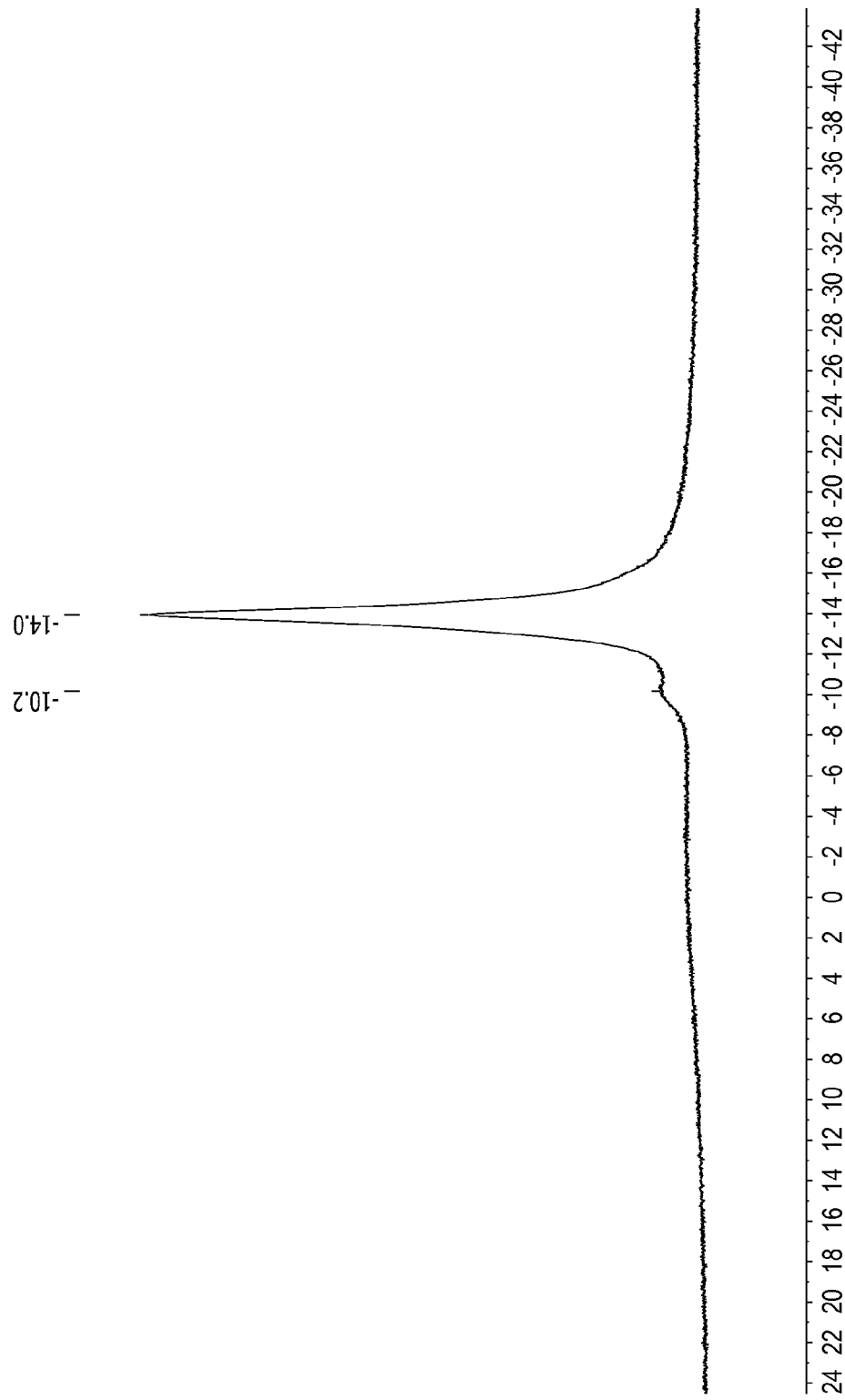

FIG. 32 shows a $^{11}$B-($^1$H-dec) NMR of 10 in THF-$d_8$.

Figure 33:
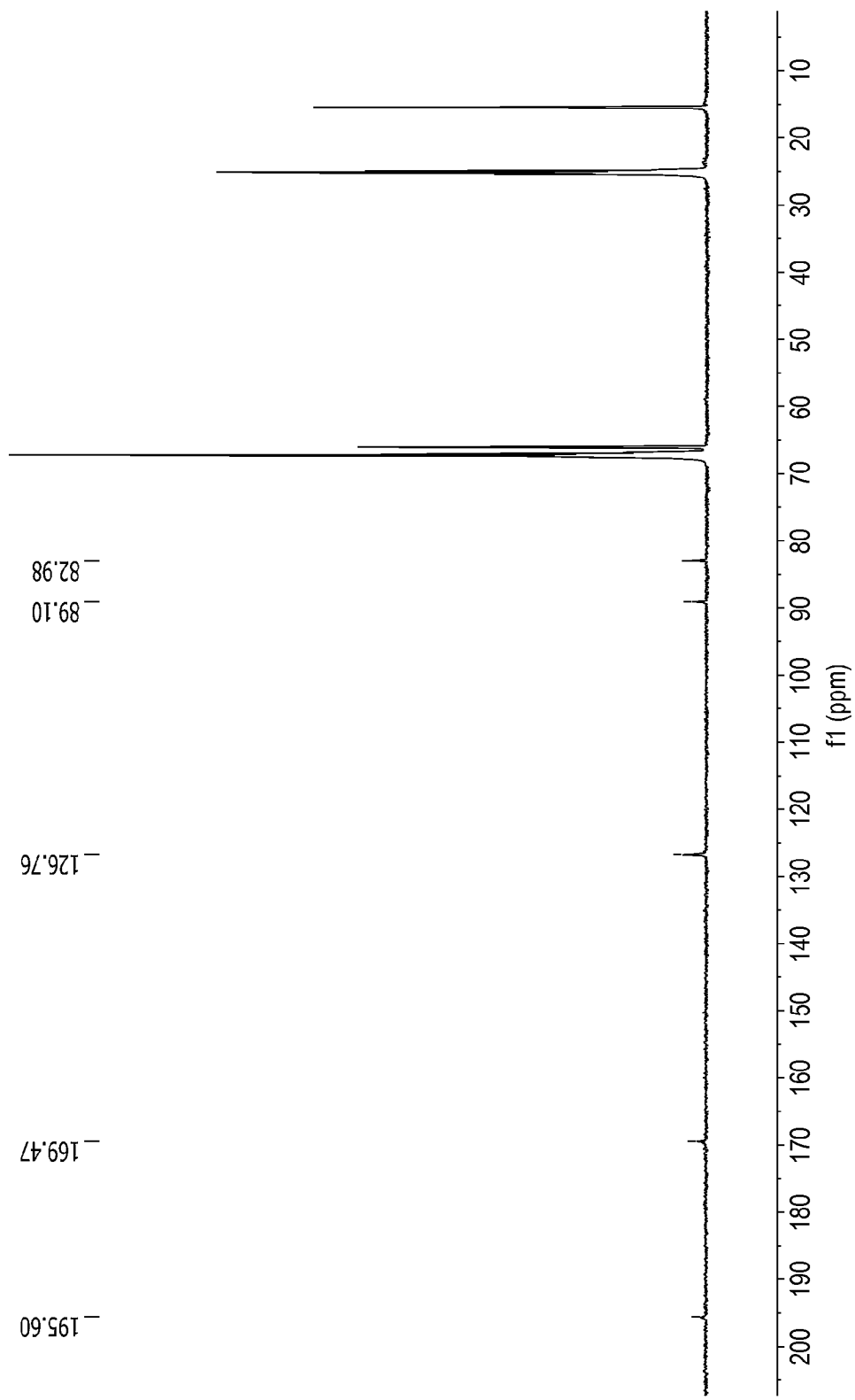

FIG. 33 shows a $^{13}$C-($^1$H-dec) NMR spectrum of 10 in THF-$d_8$.

Figure 34:
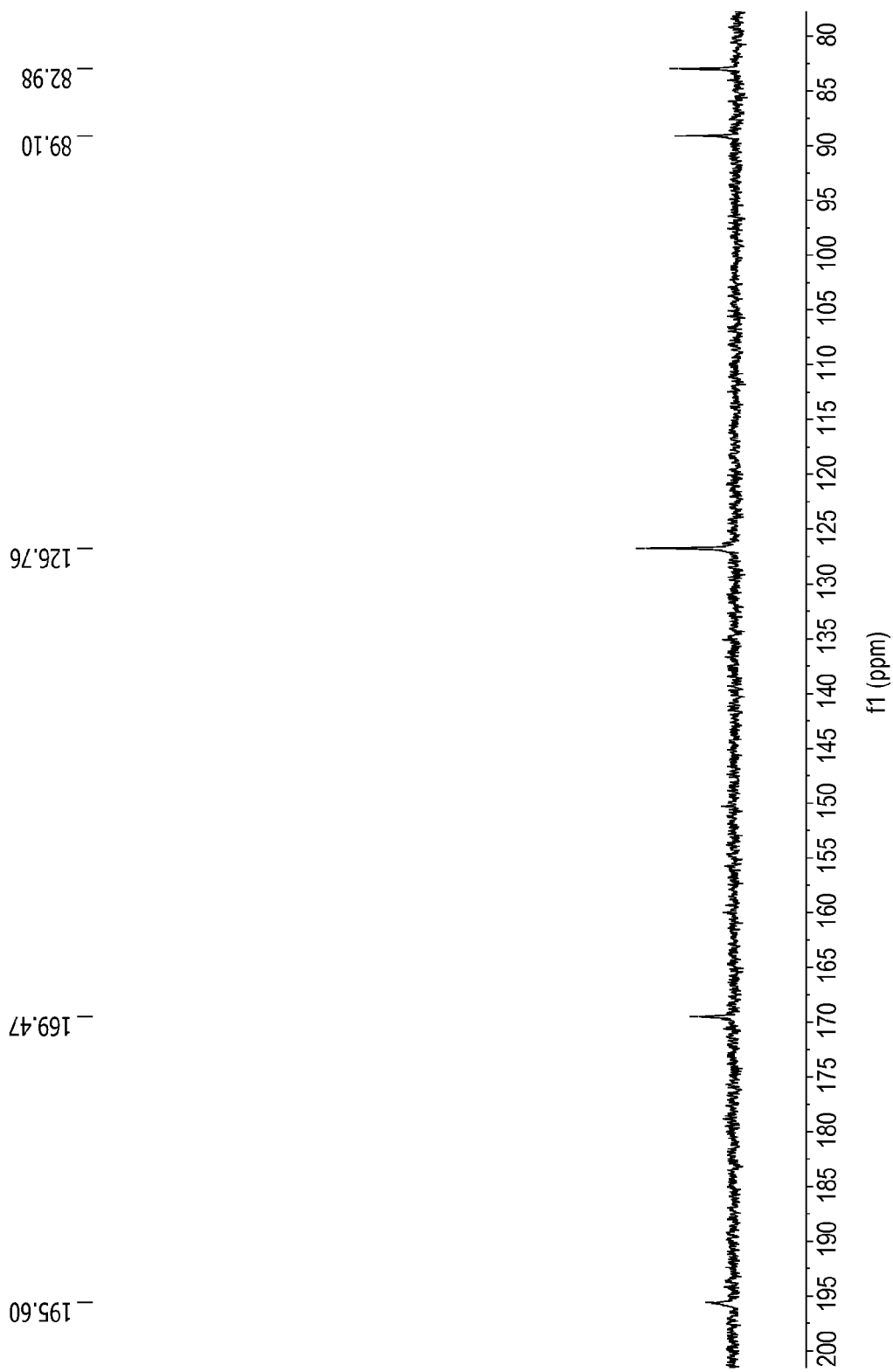

FIG. 34 shows an expanded view of the $^{13}$C-($^1$H-dec) NMR spectrum of 10 in THF-$d_8$.

Figure 35:
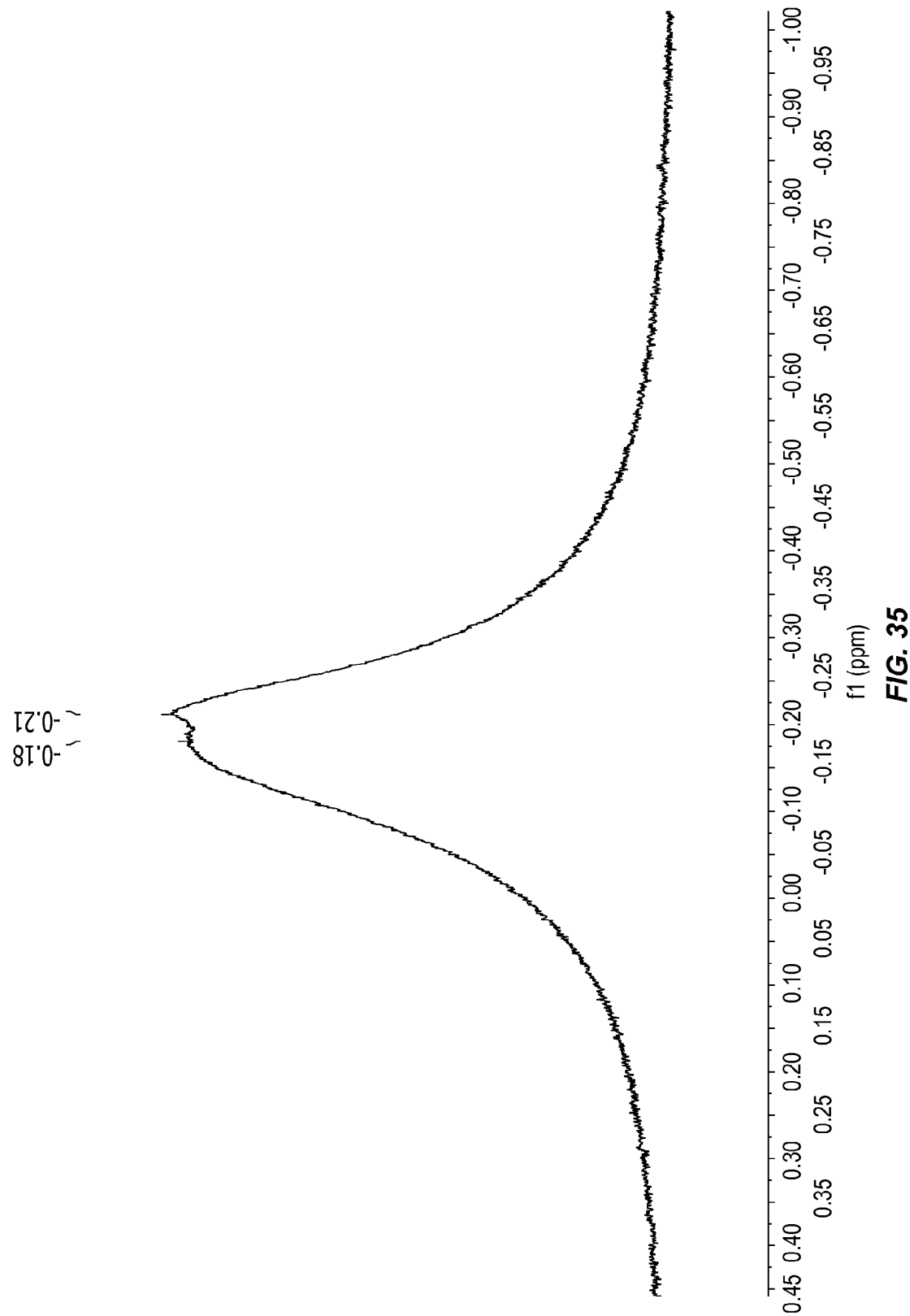

FIG. 35 shows a $^7$Li-NMR spectrum of 10 in THF.

Figure 36:
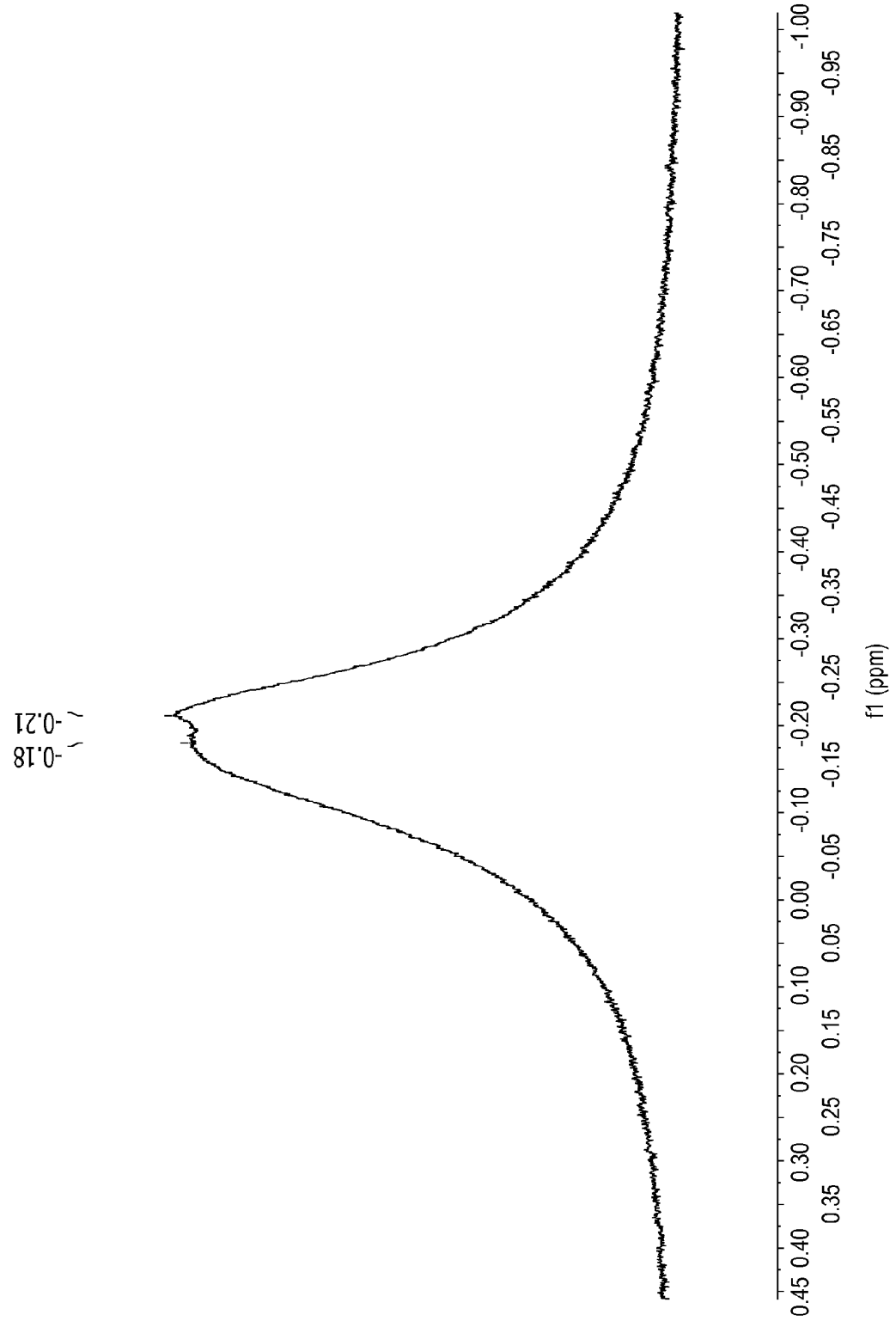

FIG. 36 shows an xpanded view of $^7$Li-NMR spectrum of 10 in THF showing two $^7$Li resonances.

Figure 37:
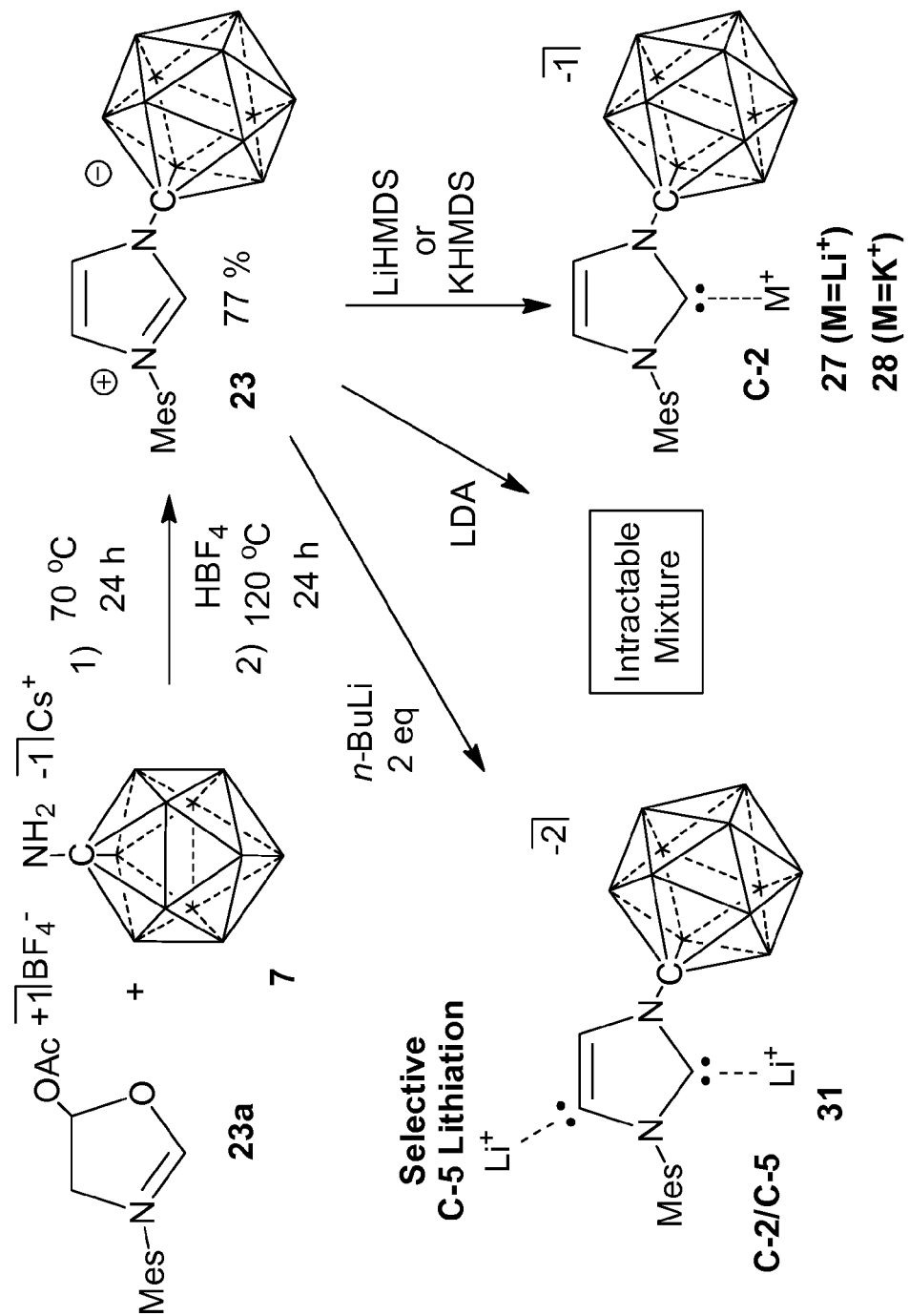

FIG. 37 shows the synthesis of zwitterionic imidazolium 23 and its reaction with different bases to form anionic 27, 28 and dianionic 31 NHCs. The second lithiation of 23 with n-BuLi occurs with perfect selectivity at the C-5 position to form 31. M=Li or K, unsubstituted vertices=B—H.

Figure 38:
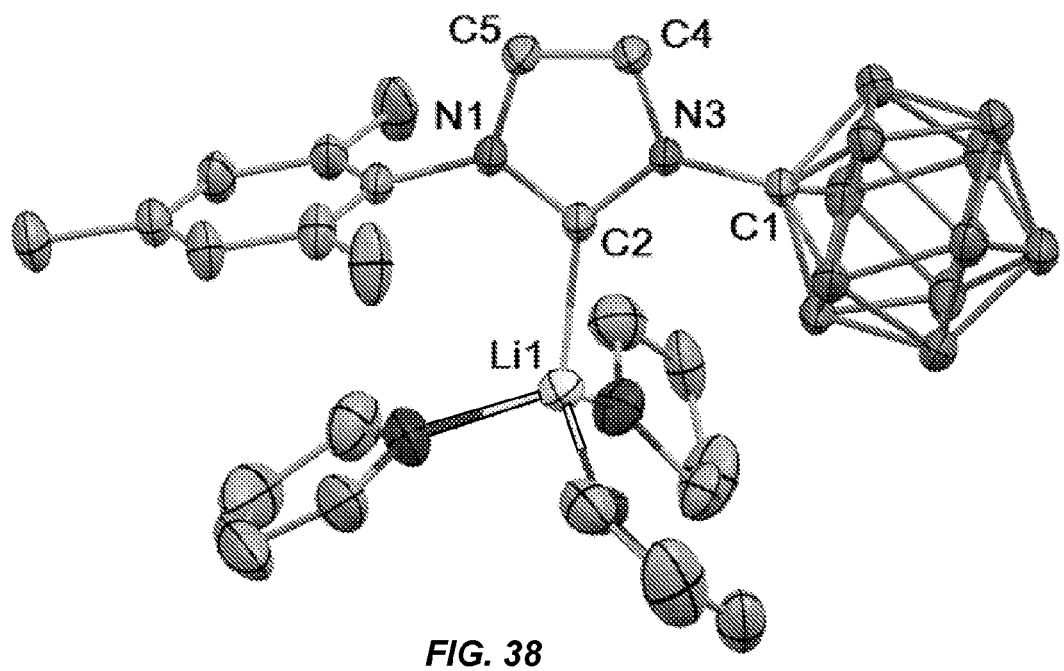

FIG. 38 shows the solid state structure of 27.

Figure 39:
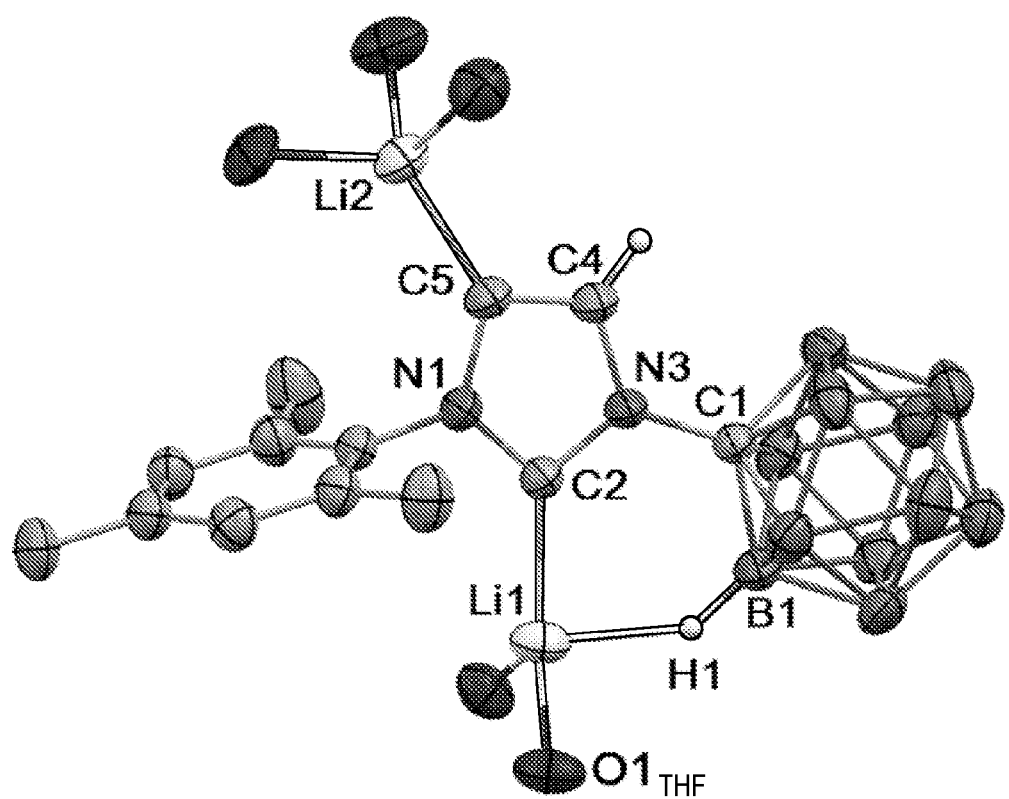

FIG. 39 shows the solid state structure of 31. Carbon rings of THF molecules and most hydrogen atoms (except H1, and C4-H) are omitted for clarity.

DETAILED DESCRIPTION OF THE INVENTION

I. General

The instant patent application sets forth, in part, the fusion of carbenes with carborane anions to selectively produce stable lithium and magnesium adducts of dianionic normal C-2 and abnormal C-5 imidazolylidene constitutional isomers, as well as a trianionic C-2/C-5 deprotonated species from a single precursor. Judicious choice of the base and reaction conditions allows for the selective formation of all three stable polyanionic carbenes. In certain embodiments, these molecules are prepared via a a novel condensation reaction between unusual anionic carboranyl amines and ketone or aldehyde derivatives. The combination of two unusual forms of carbon atoms lead to unexpected chemical behavior, and the discovery of this behavior provides new opportunities for catalysis and energy storage.

II. Definitions

As used herein, the terms "zwitterionic" and "zwitterion" refer to a neutral compound having both positive and negative charged groups therein.

As used herein, the terms "halide" and "halogen" refer to F, Cl, Br, or I, as well as anions thereof.

As used herein, the term "alkyl," by itself or as part of another substituent, refers to a hydrocarbon group derived from an alkane by removing one hydrogen atom. Examples of alkyl include, but are not limited to, methyl, ethyl, isopropyl, n-propyl, n-butyl, t-butyl, isopentyl, and n-pentyl. Alkyl can include any straight-chain or branched-chain alkyl alkyl group having from about 1 to about 16 carbon atoms. In certain instances, alkyl groups include numeric designators indicating number of carbon atoms. For example, $C_{1-10}$ alkyl refers to an alkyl group having from one to ten carbon atoms with the remaining valences filled occupied by hydrogen atoms. In some embodiments of the invention, alkyl groups are those with 1 to 8 carbon atoms, such as a straight or branched-chain alkyl group with 1 to 6 carbon atoms or a straight or branched-chain alkyl group with 1 to 4 carbon atoms. In certain embodiments, an alkyl group can be substituted with from one to twelve substituents selected from halogen, haloalkyl, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, and nitro.

As used herein, the term "haloalkyl," by itself or as part of another substituent, refers to an alkyl group where some or all of the hydrogen atoms are replaced with halogen atoms. As for alkyl groups, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

As used herein, the term "aryl," by itself or as part of another substituent, refers to a group derived from an aromatic compound by removing one hydrogen atom. Examples of aryl include, but are not limited to, phenyl, mesityl, 2,6,-diisopropylphenyl, napthyl, and benzyl. In certain embodiments, an aryl group can be substituted with from one to five substituents selected from halogen, haloalkyl, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, and nitro.

As used herein, the term "alkoxy," by itself or as part of another substituent, refers to a group having the formula —O—R, wherein R is alkyl.

As used herein, the term "aryloxy," by itself or as part of another substituent, refers to a group having the formula —O—R, wherein R is aryl.

As used herein, the term "silyl," by itself or as part of another substituent, refers to a group having the formula —Si—$R_3$, wherein R is alkyl or aryl. The term "siloxy" refers to a group having the formula —O—Si—$R_3$, wherein R is alkyl or aryl.

As used herein, the term "carbonyl," by itself or as part of another substituent, refers to —C(O)—, i.e., a carbon atom double-bonded to oxygen and bound to two other groups in the moiety having the carbonyl.

As used herein, the term "thio," by itself or as part of another substituent, refers to (=S), i.e., a sulfur atom double-bonded to a another atom in the group having the thio moiety.

As used herein, the term "amino," by itself or as part of another substituent, refers to a group having the formula —$NR_2$ wherein each R group is independently selected from hydrogen, alkyl, and aryl as described herein.

As used herein, the term "carbamoyl," by itself or as part of another substituent, refers to a group having the formula —C(O)$NR_2$ wherein each R group is independently selected from hydrogen, alkyl, and aryl as described herein.

As used herein, the term "methylenedioxy," by itself or as part of another substituent, refers to a diradical having the formula —O—$CH_2$—O—, wherein the oxygen radicals are bound to the same atom in a group having the methylenedioxy moiety or to different atoms in the group having the methylenedioxy moiety.

As used herein, the term "cyano," by itself or as part of another substituent, refers to a moiety having the formula —CN, i.e., a carbon triple-bonded to nitrogen and bound to one other group in the moiety having the cyano.

As used herein the term "heterocycle," by itself or as part of another substituent, refers to heteroaryl and heterocycloalkyl groups. In general, the carborane compounds of the invention contain at least one heterocycle having at least one nitrogen atom. "Heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (=O), among many others.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

As used herein the term "neutral ligand" refers to an uncharged compound capable of binding to cations (including metallic cations). Examples of neutral ligands include, but are not limited to, ammonia, water, triphenylphosphine, 2,2'-bipyridine, 1,10-phenanthroline, 2,2',2"-terpyridine, tetrahydrofuran, diethyl ether, and the like.

As used herein the term "anionic ligand" refers to a negatively-charged species capable of binding to cations (including metallic cations). Examples of anionic ligands include, but are not limited to, carboylates and halides.

As used herein the term "anion" refers to a negatively-charged ion.

As used herein the term "cation" refers to a positively-charged ion.

As used herein, the term "carbene transfer agent" refers to a compound capable of forming a carbene. Carbene transfer agents include, but are not limited to, diazo compounds such as ethyl diazoacetate; t-butyl diazoacetate; 2,3,4-trimethyl-3-pentyl diazoacetate; menthyl diazoacetate; 2,5-dimethyl-4-hexen-2-yl diazoacetate; 3-(diazoacetyl)amino propionate, and diazoacetylamino acetate.

As used herein, the term "carba-closo-dodecaborate anion" refers to a compound having the formula $[R^4CB_{11}(R^1)_{11}]^{-1}$ as depicted below:

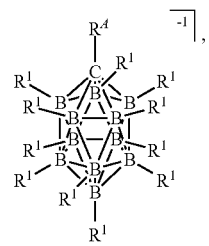

wherein $R^1$ is selected from H, halogen, alkyl, aryl, silyl, siloxy, haloalkyl, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, and alkoxy. In certain embodiments, $R^1$ is selected from H, halogen, alkyl, aryl, silyl, siloxy, and alkoxy. $R^4$ represents the remaining portion of the carba-closo-dodecaborate anion.

In some embodiments, the "carba-closo-dodecaborate substituent" having the formula $[R^4CB_{11}(R^1)_{11}]^{-1}$ is represented by:

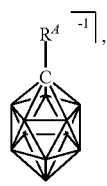

wherein the vertices which are not labeled "C" represent B—$R^1$. $R^4$ represents the remaining portion of the molecule to which the carba-closo-dodecaborate substituent is covalently bound.

Figure 1:
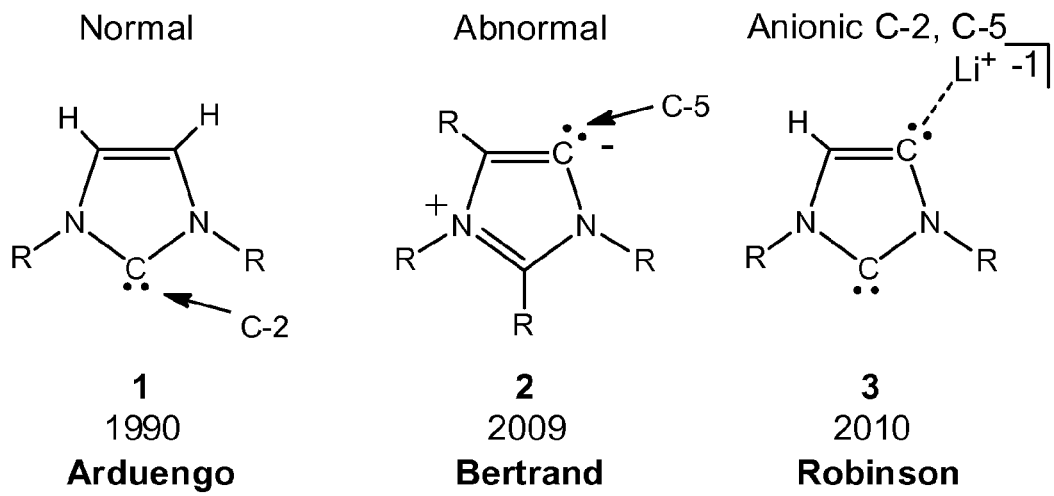
FIG. 1 shows different classes of NHCs and an icosahedral carborane anion. Generic representations of a normal (C-2) 1, abnormal (C-5) 2, anionic dicarbene 3 (C-2, C-5) (R=alkyl or aryl), and the carba-closo-dodecaborate anion 4 (chemical formula=$HCB_{11}H_{11}^-$, unlabeled vertices=B—H).
Figure 1:
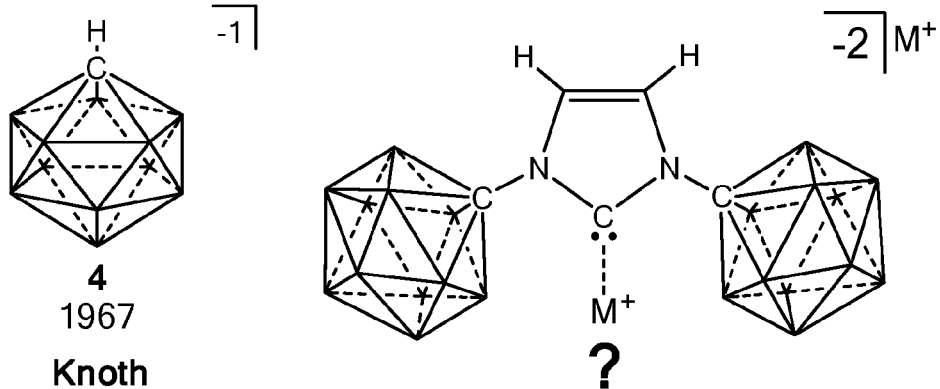

As shown in FIG. 1, for example, structure 4 is a carba-closo-dodecaborate anion wherein $R^4$ is H, each unlabeled vertex represents a boron atom substituted with R', and each $R^1$ is H. In certain embodiments, $R^4$ is a nitrogen-containing substituent wherein a nitrogen atom is covalently bound to the carbon atom of a carba-closo-dodecaborate anion or a carba-closo-dodecaborate substituent. $R^4$ can be, but is not limited to, an imidazolyl group or a diimino group.

III. Compositions

Figure 2:
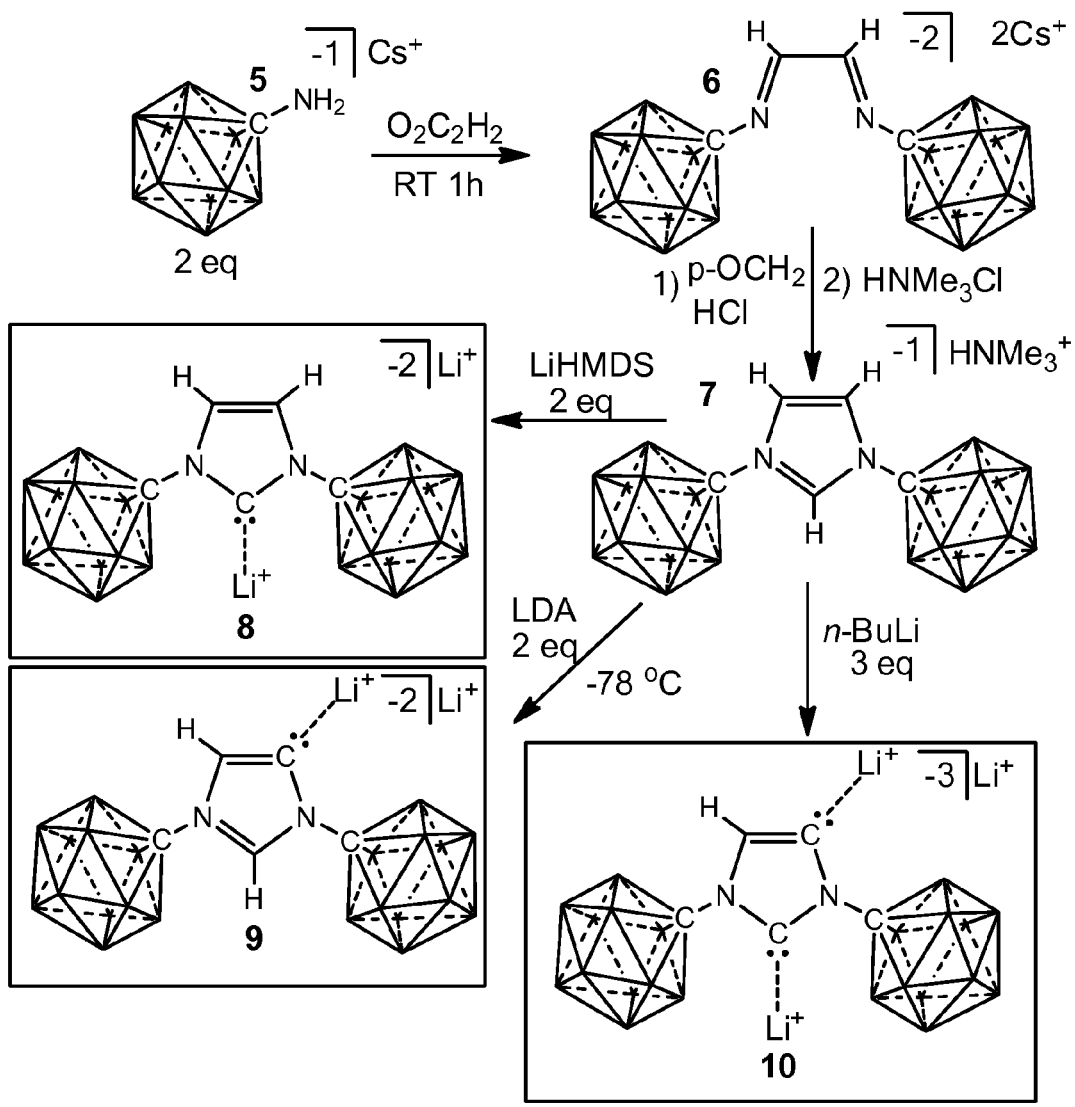
FIG. 2 shows synthesis of polyanionic normal (C-2) 8, abnormal (C-5) 9, and C-2/C-5 deprotonated species 10 (unlabeled carborane vertices=B—H).

The present invention includes the use of the carba-closo-dodecaborate anion 4 (FIG. 1) and its derivatives (including halogenated derivatives) as alkyl and aryl surrogates for ligand and catalyst design.[12] Methods set forth herein include synthesizing a normal NHC that would be rendered dianionic, as a result of containing two negatively charged and weakly coordinating[13] N-carboranyl substituents (FIG. 1). When generated with an alkali or alkali-metal containing base, such an NHC would inevitably form a complex with one of the two countercations. Although the prerequisite anionic carboranyl amine 5 was reported over 25 years ago, and is accessible in large quantities from decaborane $(B_{10}H_{14})$,[14] this unusual anionic amine has never been reported to undergo condensation reactions with aldehydes or ketones (FIG. 2).

In some embodiments, the invention provides compounds according to Formula 1:

(1)

In some embodiments, $Het^N$ of Formula 1 is an N-heterocyclic carbene (NHC) moiety or an NHC precursor moiety. $R^B$ is a carba-closo-dodecaborate substituent. $R^W$ is selected from a carba-closo-dodecaborate substituent (i.e., $R^B$), H, halogen, alkyl, aryl, silyl, siloxy, alkoxy, and aryloxy, each of which is substituted with a member independently selected from halogen, hydroxyl, and hydroxide. A is present or absent. When present, A represents one or more cations.

In some embodiments, $Het^N$ is an imidazolium moiety. In some embodiments, $Het^N$ is an triazolium moiety. In some embodiments, $Het^N$ is a pyrrolidinium moiety.

Typically, the $R^B$-$Het^N$-$R^W$ group in compounds of Formula 1 will be neutral or will have a net negative charge. The net charge of the $R^B$-$Het^N$-$R^W$ group can be represented as "x," as shown in Formula 1a. In general, a cation "A" in a compound of the invention will be present in an amount sufficient to neutralize the net charge associated with the $R^B$-$Het^N$-$R^W$ group. If "x" is −2 and A is a Li$^+$ cation in Formula 1a, for example, "y" in FIG. 1a will be 2. If "x" is −3 and A is a Li$^+$ cation in Formula 1a, "y" will be 3. If "x" is −2 and A is a Ca$^{2+}$ cation in Formula 1a, "y" in FIG. 1a will be 1.

(1a)

In some embodiments, $Het^N$ in Formula 1 is selected from:

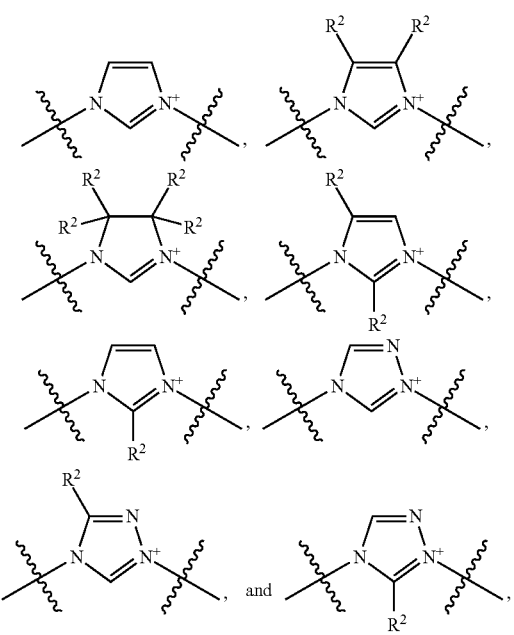

wherein each R² is independently selected from H, halogen, alkyl, aryl, silyl, siloxy, alkoxy, and aryloxy. In R², each alkyl, aryl, silyl, siloxy, alkoxy, and aryloxy is optionally substituted with a member independently selected from halogen, hydroxyl, and hydroxide (i.e., an O⁻ group).

In some embodiments, Het$^N$ in Formula 1 is:

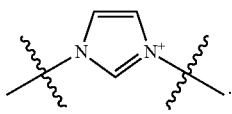

In some embodiments, Het$^N$ in Formula 1 is selected from:

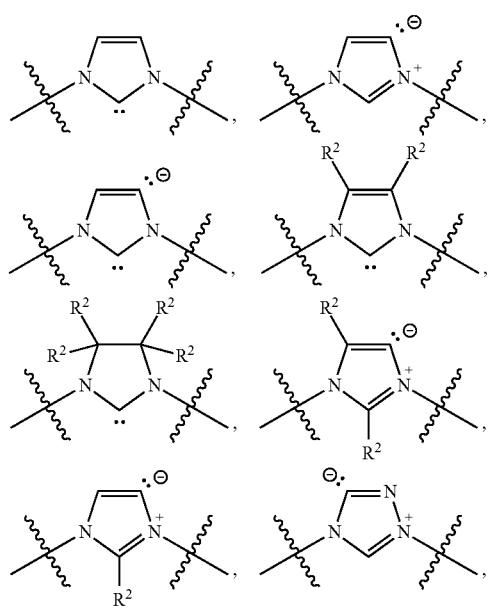

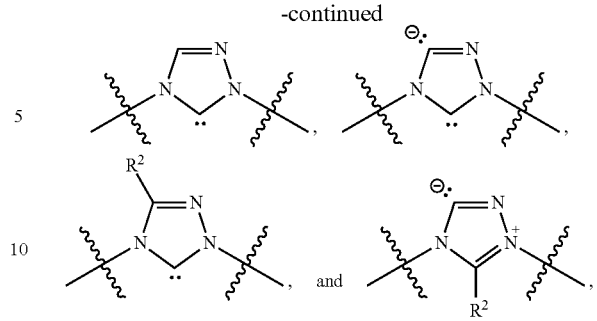

wherein each R² is independently selected from H, halogen, alkyl, aryl, silyl, siloxy, alkoxy, and aryloxy. Each R² is independently and optionally substituted as described above.

In some embodiments, Het$^N$ in Formula 1 is selected from:

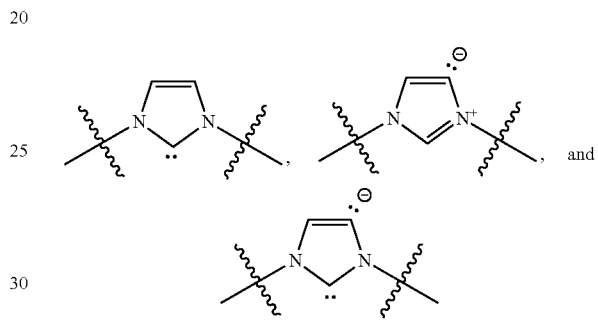

In compounds of Formula 1, carba-closo-dodecaborate substituent R$^B$ has the structure:

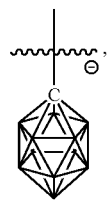

wherein each unlabeled vertex is a boron atom substituted with R¹ (i.e., a B—R¹ group). Each R¹ is independently selected from H, halogen, alkyl, aryl, silyl, siloxy, alkoxy, haloalkyl, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, and aryloxy. In R¹, each alkyl, aryl, silyl, siloxy, alkoxy, and aryloxy is optionally substituted with a member independently selected from halogen, hydroxyl, hydroxide, haloalkyl, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, and alkoxy.

In certain embodiments, R¹ is independently selected from H, halogen, alkyl, aryl, silyl, siloxy, alkoxy, and aryloxy. In certain embodiments, each alkyl, aryl, silyl, siloxy, alkoxy, and aryloxy in R¹ is optionally substituted with a member independently selected from halogen, hydroxyl, and hydroxide.

In some embodiments, R$^W$ in Formula 1 is alkyl or aryl. Compounds wherein R$^W$ is a carba-closo-dodecaborate substituent can be represented by Formula 2:

(2)

For compounds of Formula 2, Het$^N$ is an N-heterocyclic carbene (NHC) moiety or an NHC precursor moiety, each R$^B$ is a carba-closo-dodecaborate substituent, and A is present or absent. When present, A represents one or more cations.

In some embodiments, Het$^N$ is an imidazolium moiety. In some embodiments, Het$^N$ is an triazolium moiety. In some embodiments, Het$^N$ is a pyrrolidinium moiety.

Typically, the R$^B$-Het$^N$-R$^B$ group in compounds of the invention will be neutral or will have a net negative charge. The net charge of the R$^B$-Het$^N$-R$^B$ group can be represented as "x," as shown in Formula 2a. In general, a cation "A" in a compound of the invention will be present in an amount sufficient to neutralize the net charge associated with the R$^B$-Het$^N$-R$^B$ group. If "x" is −2 and A is a Li$^+$ cation in Formula 2a, for example, "y" in FIG. 2a will be 2. If "x" is −3 and A is a Li$^+$ cation in Formula 2a, "y" will be 3. If "x" is −2 and A is a Ca$^{2+}$ cation in Formula 2a, "y" in FIG. 2a will be 1.

(2a)

In some embodiments, Het$^N$ is selected from:

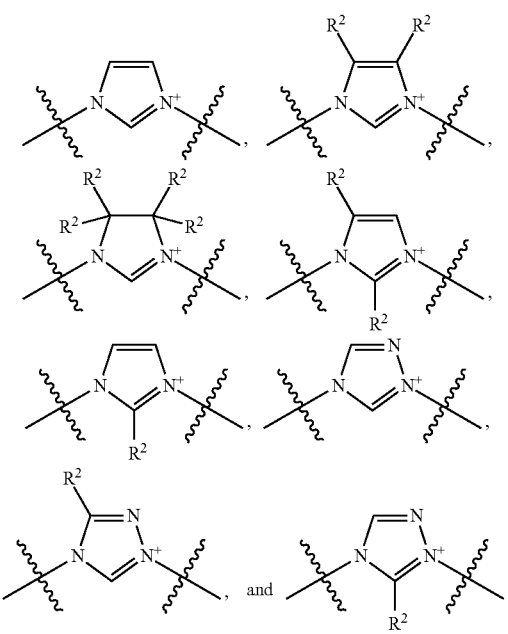

wherein each R$^2$ is independently selected from H, halogen, alkyl, aryl, silyl, siloxy, alkoxy, and aryloxy. In R$^2$, each alkyl, aryl, silyl, siloxy, alkoxy, and aryloxy is optionally substituted with a member independently selected from halogen, hydroxyl, and hydroxide (i.e., an O$^−$ group).

In some embodiments, Het$^N$ is:

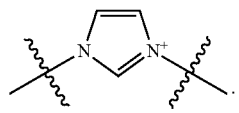 [SMILES: *n1cc[n+](*)c1]

In some embodiments, Het$^N$ is selected from:

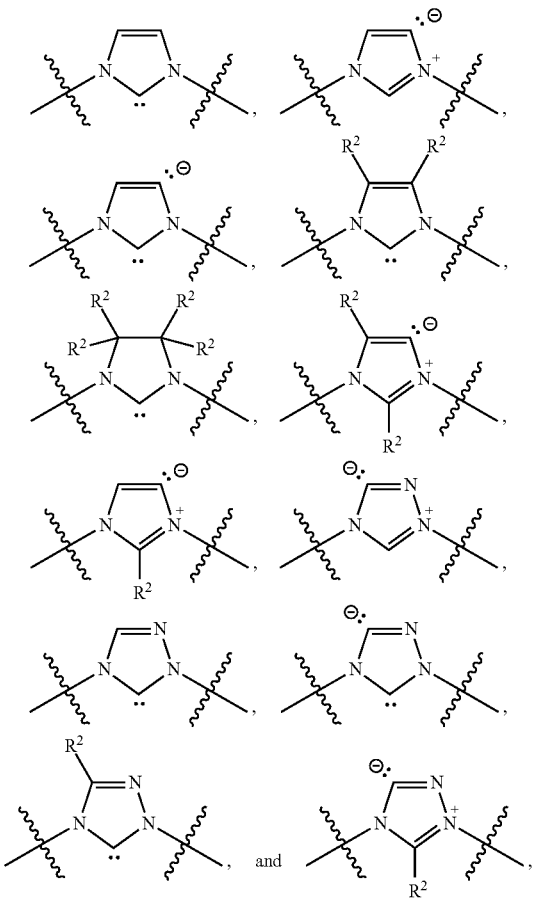

wherein each R$^2$ is independently selected from H, halogen, alkyl, aryl, silyl, siloxy, alkoxy, and aryloxy. Each R$^2$ is independently and optionally substituted as described above.

In some embodiments, Het$^N$ is selected from:

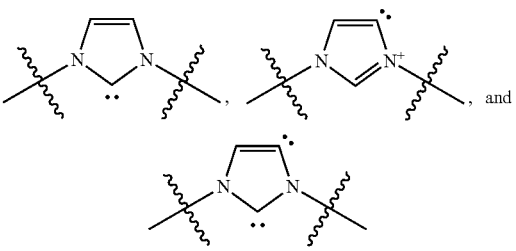

In compounds of Formula 2, carba-closo-dodecaborate substituent R$^B$ has the structure:

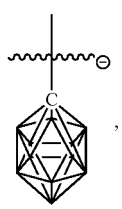

wherein each unlabeled vertex is a boron atom substituted with $R^1$ (i.e., a B—$R^1$ group). Each $R^1$ is independently selected from H, halogen, alkyl, aryl, silyl, siloxy, alkoxy, haloalkyl, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, and aryloxy. In $R^1$, each alkyl, aryl, silyl, siloxy, alkoxy, and aryloxy is optionally substituted with a member independently selected from halogen, hydroxyl, hydroxide, haloalkyl, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, and alkoxy.

In certain embodiments, $R^1$ in compounds of Formula 2 is independently selected from H, halogen, alkyl, aryl, silyl, siloxy, alkoxy, and aryloxy. In certain embodiments, each alkyl, aryl, silyl, siloxy, alkoxy, and aryloxy in $R^1$ is optionally substituted with a member independently selected from halogen, hydroxyl, and hydroxide.

In some embodiments, the invention provides a compound having the structure selected from Formula (I), Formula (II), Formula (III), Formula (IV), Formula (V), Formula (VI), Formula (VII), Formula (VIII), Formula (IX), Formula (X), Formula (XI), Formula (XII), Formula (XIII), Formula (XIV), Formula (XV), Formula (XVI), and Formula (XVII):

(I)

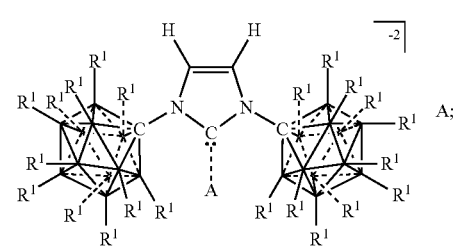

(II)

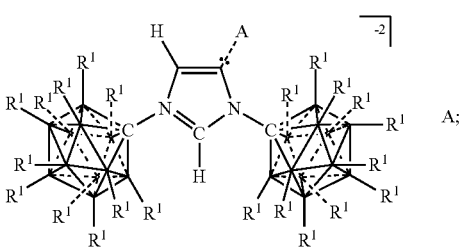

(III)

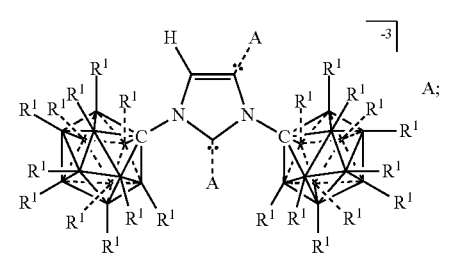

(IV)

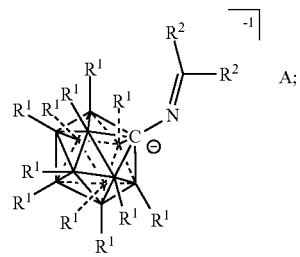

(V)

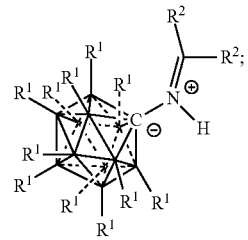

(VI)

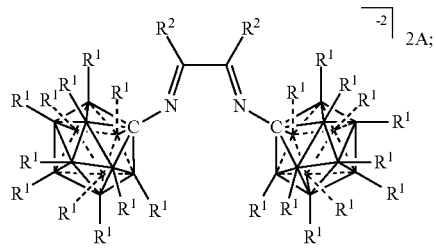

(VII)

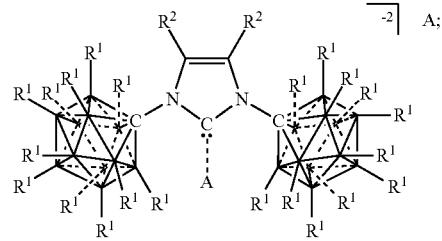

(VIII)

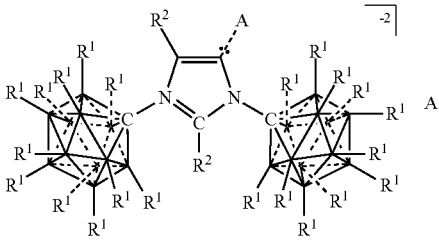

(IX)

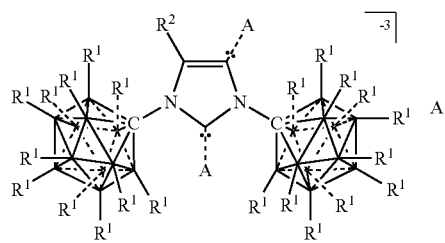

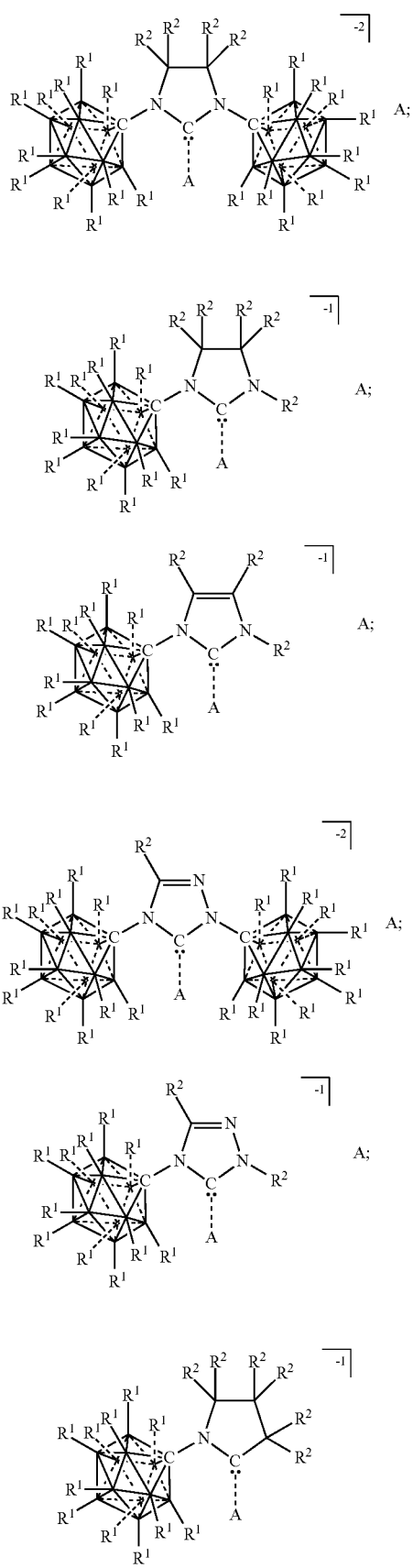

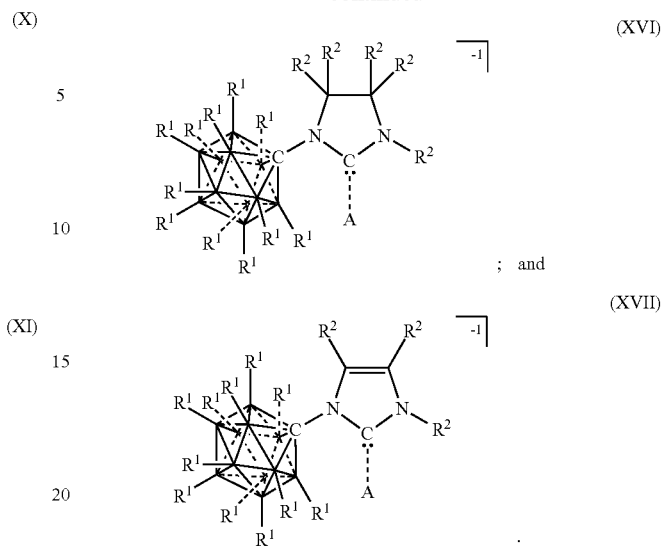

In Formulas (I)-(XVII), each $R^1$ and $R^2$ is independently selected from H, halogen, alkyl, aryl, silyl, siloxy, alkoxy, haloalkyl, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, alkoxy, and aryloxy, wherein each alkyl, aryl, silyl, siloxy, alkoxy, and aryloxy is optionally and independently substituted with halogen, hydroxyl, hydroxide (i.e., O⁻), haloalkyl, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, or alkoxy. In structures (I)-(XVII), A is a cation.

In certain embodiments, the invention provides compounds according to Formulas (I)-(XVII) wherein each $R^1$ and $R^2$ is independently selected from H, halogen, alkyl, aryl, silyl, siloxy, alkoxy, and aryloxy, wherein each alkyl, aryl, silyl, siloxy, alkoxy, and aryloxy is optionally and independently substituted with halogen, hydroxyl, or hydroxide (i.e., O⁻).

In some embodiments, A is selected from $Li^+$, $Na^+$, $K^+$, $Cs^+$, $HN(alkyl)_3^+$, $N(alkyl)_4^+$, $Mg^{2+}$, $Ca^{2+}$, $Zn^{2+}$, $Al^{3+}$, and $Ag^+$.

In some embodiments, each $R^1$ and $R^2$ is independently selected from H, alkyl, and aryl.

In some embodiments, the invention provides compounds having the following structure:

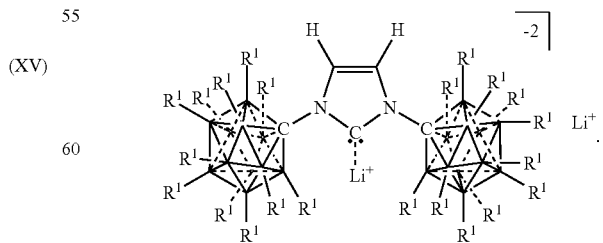

In some embodiments, the invention provides compounds having the following structure:

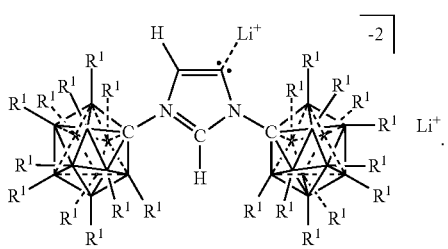

In some embodiments, the invention provides compounds having the following structure:

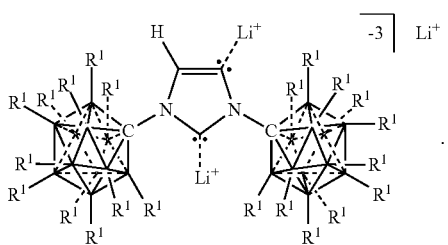

In some embodiments, each $R^1$ is a halogen independently selected from F, Cl, Br, and I. In some embodiments, $R^1$ is H. In some embodiments, $R^1$ is Cl. In some embodiments, $R^1$ is Br. In some embodiments, $R^1$ is I. In some embodiments, $R^1$ is alkyl. In some embodiments, $R^1$ is alkoxy. In some embodiments, $R^1$ is siloxy.

In some embodiments, A is $Li^+$.

In some embodiments, each $R^2$ is a halogen independently selected from F, Cl, Br, and I. In some embodiments, $R^2$ is H. In some embodiments, $R^2$ is Cl. In some embodiments, $R^2$ is Br. In some embodiments, $R^2$ is I. In some embodiments, $R^2$ is alkyl. In some embodiments, $R^2$ is alkoxy. In some embodiments, $R^2$ is siloxy.

In some embodiments, the invention provides compounds having the following structure:

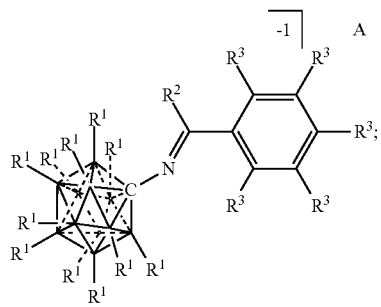

wherein each $R^3$ is independently selected from H, hydroxyl, hydroxide, halogen, alkyl, aryl, silyl, and alkoxy.

In some embodiments, the invention provides compounds having the following structure:

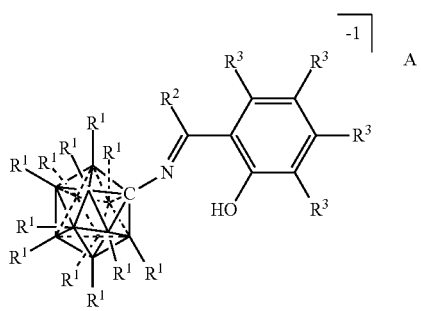

In some embodiments, the invention provides compounds having the following structure:

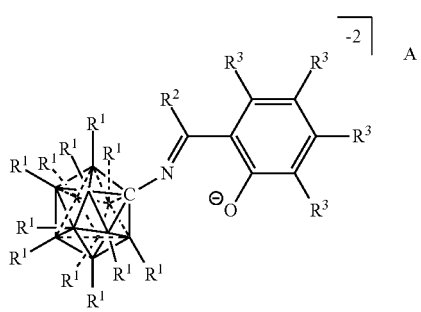

In some embodiments, compounds of the invention as described herein further comprise a transition metal. In some embodiments, the transition metal is selected from Fe, Ru, Os, Co, Rh, Ir, Ni, Pd, Pt, Cu, Ag, and Au. In some embodiments, the transition metal is selected from Fe, Ru, Co, Ni, and Pd.

In a related aspect, the invention provides compositions comprising: a solvent selected from dimethoxy ethane, dioxane, pyridine, tetrahydrofuran, diethyl ether, benzene, toluene, acetonitrile, methylene chloride, chloroform, dimethyl formamide, and acetone; a compound of the invention as described above; and a transition metal selected from Fe, Ru, Os, Co, Rh, Ir, Ni, Pd, Pt, Cu, Ag, and Au.

IV. Methods for Synthesizing Carborane Compounds

The present invention provides various methods for making the compounds described above. In certain embodiments, the methods include one or more steps set forth in the Examples.

Accordingly, some embodiments of the invention provide a process for preparing a compound according to Formula (C):

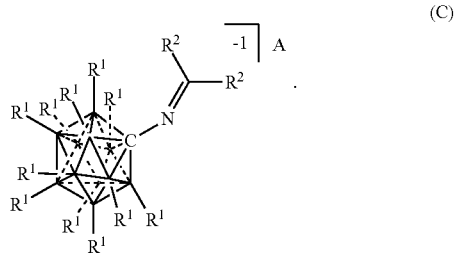

(C)

The process for preparing a compound according to Formula (C) includes condensing a compound according to Formula (A):

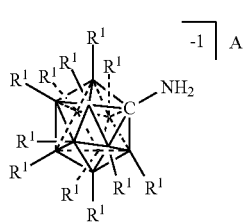
(A)

with a compound according to Formula (B)

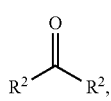
(B)

under conditions sufficient to form the compound of Formula (C).

In processes for preparing a compound according to Formula (C), each unlabeled vertex bonded to $R^1$ represents a boron atom; each $R^1$ and each $R^2$ is independently selected from H, halogen, alkyl, aryl, silyl, siloxy, aryloxy, haloalkyl, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, and nitro; each alkyl, aryl, silyl, siloxy, alkoxy, and aryloxy is optionally substituted with a member independently selected from phosphine, phosphite halogen, hydroxyl, hydroxide, haloalkyl, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, or alkoxy; and A is a cation.

In some embodiments, the invention provides processes for preparing a compound according to Formula (C) wherein each $R^1$ and each $R^2$ is independently selected from H, halogen, alkyl, aryl, silyl, siloxy, alkoxy, and aryloxy; and each alkyl, aryl, silyl, siloxy, alkoxy, and aryloxy is optionally substituted with a member independently selected from halogen, hydroxyl, and hydroxide.

In some embodiments, the invention provides a process for preparing a compound according Formula (D),

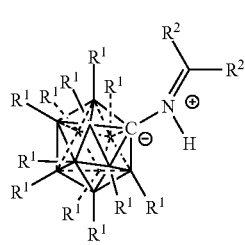
(D)

The process for preparing a compound according to Formula (D) includes condensing a compound according to Formula (E)

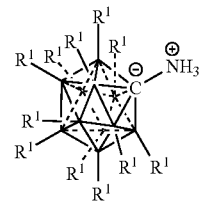
(E)

with a compound according to Formula (B):

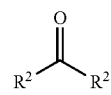
(B)

under conditions sufficient to form the compound of Formula (D).

In processes for preparing a compound according to Formula (D), each unlabeled vertex bonded to $R^1$ represents a boron atom; each $R^1$ and each $R^2$ is independently selected from H, halogen, alkyl, aryl, silyl, siloxy, alkoxy, aryloxy, haloalkyl, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, and nitro; each alkyl, aryl, silyl, siloxy, alkoxy, and aryloxy is optionally substituted with a member independently selected from phosphine, phosphite, halogen, hydroxyl, hydroxide, haloalkyl, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, and alkoxy; and A is a cation.

In some embodiments, the invention provides processes for preparing a compound according to Formula (D) wherein each $R^1$ and each $R^2$ is independently selected from H, halogen, alkyl, aryl, silyl, siloxy, alkoxy, and aryloxy; and each alkyl, aryl, silyl, siloxy, alkoxy, and aryloxy is optionally substituted with a member independently selected from halogen, hydroxyl, and hydroxide.

In some embodiments, the invention provides a process for preparing a compound according Formula (G):

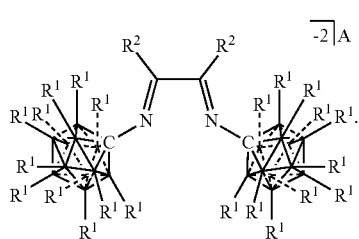
(G)

The process for preparing a compound according to Formula (G) includes condensing a compound according to Formula (A)

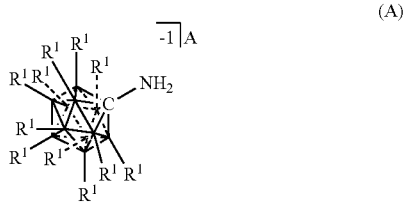

with a compound according to Formula (F):

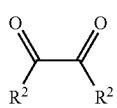

under conditions sufficient to form the compound of Formula (G).

In processes for preparing a compound according to Formula (G), each unlabeled vertex bonded to $R^1$ represents a boron atom; each $R^1$ and each $R^2$ is independently selected from H, halogen, alkyl, aryl, silyl, siloxy, alkoxy, aryloxy, haloalkyl, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, and nitro; each alkyl, aryl, silyl, siloxy, alkoxy, and aryloxy is optionally substituted with a member independently selected from phosphine, phosphite, halogen, hydroxyl, hydroxide, haloalkyl, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, and alkoxy; and A represents one or more cations.

In some embodiments, the invention provides processes for preparing a compound according to Formula (G) wherein each $R^1$ and each $R^2$ is independently selected from H, halogen, alkyl, aryl, silyl, siloxy, alkoxy, and aryloxy; and each alkyl, aryl, silyl, siloxy, alkoxy, and aryloxy is optionally substituted with a member independently selected from halogen, hydroxyl, and hydroxide.

When amine 5 was treated with glyoxal ($O_2C_2H_2$) according to the methods of the invention, a rapid double condensation reaction to afford the dianionic diimine 6 in 96% yield (FIG. 2) was observed. Subsequent treatment of 6 with para-formaldehyde (p-$OCH_2$), activated with HCl, rapidly induced ring closure and formation of the anionic imidazolium salt 7 in 94% isolated yield (FIG. 2). The $^1$H NMR spectrum of 7 showed a characteristic triplet (C—$H_{C-2}$, 1H, $^4J_{(H-H)}$=1.74 Hz,) and doublet (C—$H_{C-4,5}$, 2H, $^4J_{(H-H)}$=1.74 Hz,) at 8.50 and 7.63 ppm, respectively, which correspond to the imidazolium ring protons. The $^{13}$C NMR spectrum of 7 displays two C—H resonances for the symmetrical imidazolium ring (134.6 C—$H_{C-2}$ and 123.7 C—$H_{C-4,5}$ ppm) as well as a quaternary carborane carbon at 67.6 ppm.

Initial attempts to deprotonate 7 with excess lithium diisopropylamide (LDA) at ambient temperature led to a puzzling mixture of three new compounds as indicated by $^1$H NMR spectroscopy (ultimately determined to be 8, 9, 10) (FIG. 2). Two of the three compounds feature a single singlet resonance in the $^1$H NMR spectra at 6.91 and 6.13 ppm, respectively. It was postulated that the low field singlet at 6.91 ppm corresponded to the desired normal dianionic NHC 8, and the higher field resonance at 6.13 ppm might correspond to the C-2/C-5 deprotonated species 10. Interestingly, the third compound displays two distinct doublet resonances that are coupled at 8.26 (C—$H_{C-2}$, $^1$H, $^4J_{(H-H)}$= 1.5 Hz) and 6.31 ppm (C—$H_{C-4}$, $^1$H, $^4J_{(H-H)}$=1.5 Hz), which we tentatively assigned to the abnormal NHC 9.

All three species were persistent in solution, and thus strategies to selectively produce 8, 9 and 10 were developed. It was rationalized that the observed competitive deprotonation reactions might be explained, in part, by kinetic factors resulting from the sterically demanding anionic carborane substituents and the size of the employed base (LDA). Hence, deprotonation was attempted with (LiHMDS), a base with a less sterically congested environment at the amide center, due to the relatively longer N—Si bonds. Indeed, at RT or at −78° C. the deprotonation reaction occurred solely at the C-2 position to cleanly afford the normal dianionic NHC 8 in excellent yield (95%). The $^{13}$C NMR spectrum of 8 showed a symmetrical imidazolium ring with a distinct low field quaternary carbene resonance (196.9 ppm) as well as a signal for the equivalent hypercoordinate carborane carbons (81.4 ppm). $^7$Li NMR spectroscopy showed a resonance that is upfield (−0.52 ppm) from a LiCl standard (0.1 M/THF), which suggests the carbene complexes the alkali cation.

Figure 3:
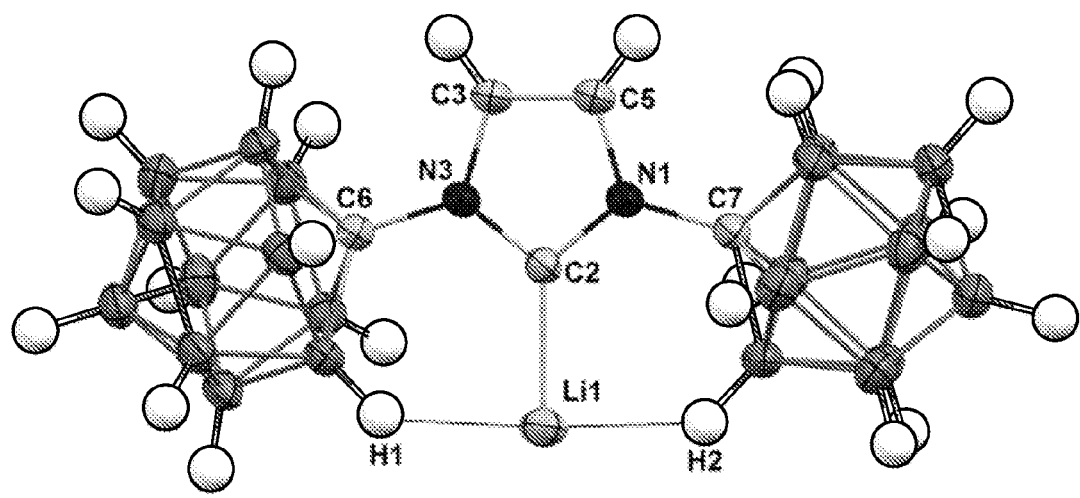
FIG. 3 shows a solid-state structure of the normal dianionic NHC 8. For clarity, two tetrahydrofuran (THF) molecules coordinated to Li' are omitted, as well as the second $Li^+$ countercation (×4 THF). Color code: C=grey, B=brown, H=white, N=blue, Li=pink.

Indeed, a single crystal X-ray diffraction study of 8 revealed that in the solid-state this NHC formed a complex with one of the two lithium countercations of the pendant carborane anions (FIG. 3). All five atoms of the central heterocyclic ring were coplanar (sum of internal pentagon angles=540°) and both N1 and N3 were planar (sum of C—N—C angles=) 360°. Relative to the monoanionic imidazolium precursor 7 (see supporting information for crystallographic data), the nitrogen carbene bond lengths of 8 (N1-C2=1.3657(14), N3-C2=1.3645(15)) were elongated with respect to the imidazolium anion 7 (N1-C2/N3-C2=1.331(2) Å)), which is in line with standard NHCs and their Li complexes.[1f, 8, 13] The carborane-nitrogen bond lengths (N1-C7=1.4521(15), N3-C6=1.4514(14) Å) and carbon boron distances in the cluster (average C-B distance 1.719(3) Å) were nearly identical to the precursor 7 (N1-C7/N3-C6=1.455(3), average C-B distance 1.716(3) Å), indicating no exo-π-conjugation with the carbene ring or disruption of the 3-dimensionally aromatic carborane core of 8.[9a, 15] The carbene/lithium bond length of 2.110(2) Å was in the range reported for standard NHC lithium complexes.[1f, 8, 13] Interestingly, two close B—H contacts with the lithium cation (H1-Li1=2.01, H2-Li1=2.19 Å) suggested the possibility of agostic-like bonding between the carborane anions and the alkali metal center.[12b, 16]

To selectively form the abnormal NHC 9, deprotonation at low temperature with LDA was conducted in an attempt to kinetically favor the attack of the bulky base at the less sterically hindered C-5 position. Carrying out the reaction at −78° C. solely afforded the abnormal NHC that could be isolated as an off-white solid in 98% yield. The $^{13}$C NMR spectra of 9 showed an unsymmetrical imidazolium ring with a distinct quaternary carbene carbon resonance at 174.7 ppm, as well as two signals (82.0 and 76.4 ppm) for the inequivalent hexacoordinate carborane carbons. The carbene carbon of 9 was significantly shielded (+27.2 ppm) compared to Bertrand's neutral abnormal carbene (201.9 ppm), and might be explained by inductive effects from the carborane anions as well as interactions with Li$^+$ in solution.[7a] Analysis of the $^7$Li NMR spectrum of 9 showed a resonance that was nearly identical (−0.51 ppm) to the normal NHC Li$^+$ adduct 8 (−0.52 ppm), which suggests that the carbene is associated with the alkali cation in solution.

Figure 4:
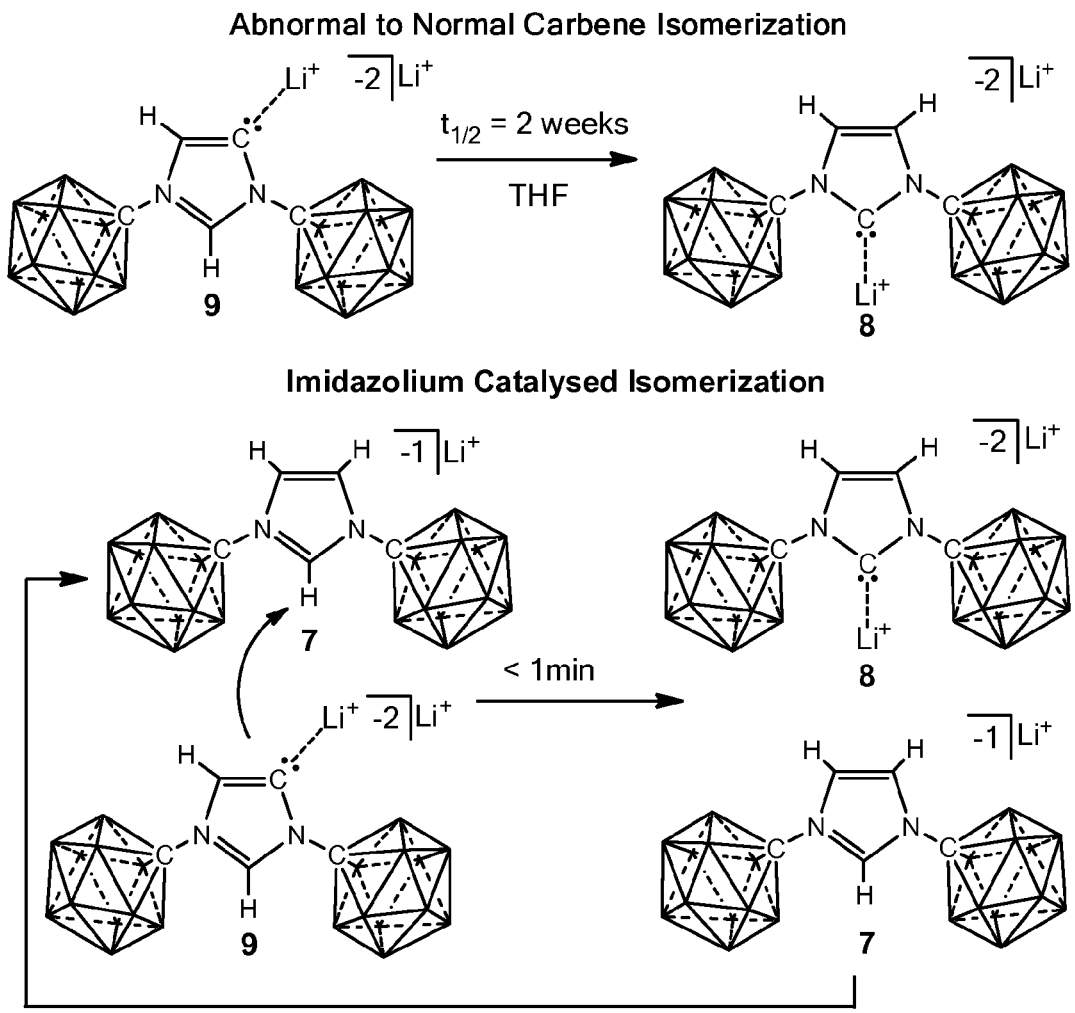
FIG. 4 shows the abnormal NHC Li adduct 9 slowly isomerizes to the normal NHC $Li^+$ complex 8 (top). The process can be proton catalyzed by the anionic imidazolium precursor 7, via the proposed reaction pathway (bottom).

Although crystals suitable for a single crystal X-ray diffraction study were not obtained, the identity of 9 was confirmed by experimentation. Addition of D$_2$O to a pure solution of 9 formed 7 with (83%) deuterium incorporation at the C-5 position. Although 9 was perfectly stable in the solid-state, when a solution of 9 was sealed in an NMR tube under an inert atmosphere and monitored by $^1$H NMR spectroscopy, it partially (t$_{1/2}$=2 weeks) isomerized[17] to the normal NHC Li$^+$ adduct 8 (FIG. 4, top). When a solution of 9 was heated to 50° C., complete isomerization of 9 to 8 was observed after 24 hours. Without wishing to be bound by any particular theory, anionic imidazolium salt 7 is believed to catalyze the process. Treating a $^1$H NMR sample of pure 9 (30 mg) with a trace (<1 mg) of 7, containing Cs$^+$ in lieu of the acidic trimethylammonium countercation, resulted in instant (<1 min) isomerization of 9 to 8. A plausible pathway involves deprotonation of 7 at the C-2 position by 9 to form the normal NHC 8 and regenerate 7 (FIG. 4, bottom).

In order to probe the possibility that the observed formation of the abnormal carbene was solely due to steric effects[18] provided by the carborane anions, a similar cationic imidazolium salt bearing alkyl groups was studies. Having two adamantyl substituents that each have a similar Van der Waals Volume (V$_{vdW}$=136 Å$^3$) to the carba-closo-dodecaborate anions of 7 (V$_{vdW}$=141-148 Å$^3$),[9f] N,N-bis-adamantylimidazolium chloride (the precursor to Arduengo's original stable NHC)[1h] was an ideal model for comparison. All attempts to generate the abnormal constitutional isomer of Arduengo's carbene by deprotonation with LDA, even with an excess of base to prevent potential proton catalyzed isomerization, resulted in the formation of the normal C-2 NHC.

Figure 5:
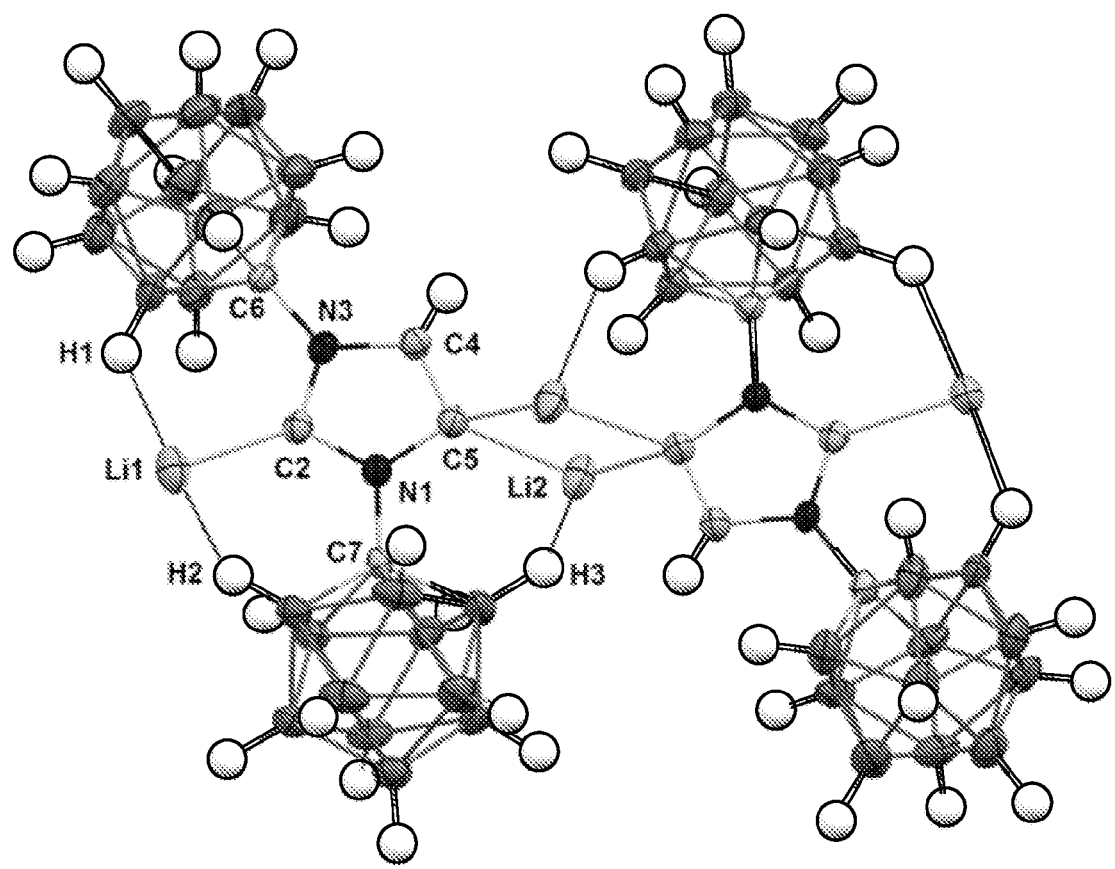
FIG. 5 shows solid-state structure of the dimeric trianionic species 10. For clarity six molecules of coordinated THF have been omitted from the lithium countercations shown above, as well as two additional Li+ countercations (×4 THF). Color code: C=grey, B=brown, H=white, N=blue, Li=pink.
Figure 6:
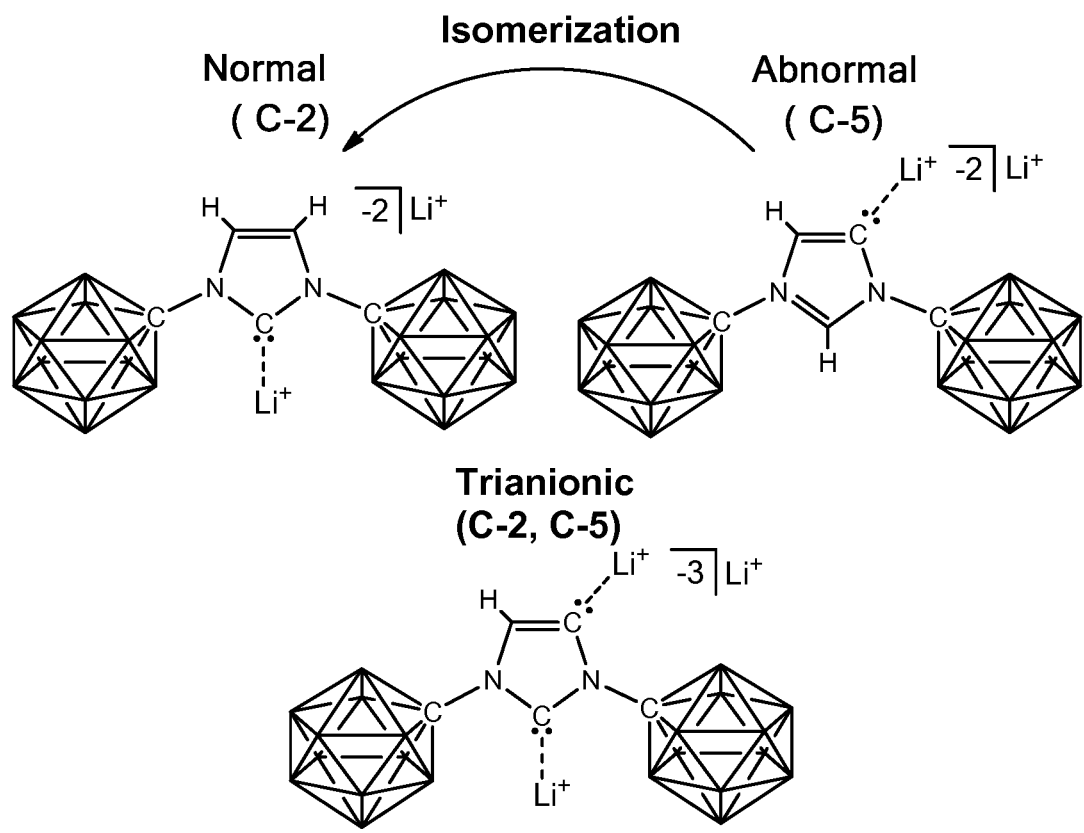
FIG. 6 shows a novel family of polyanionic N-heterocyclic carbene lithium adducts are reported, that feature two N-bonded weakly coordinating carborane anions. Judicious choice of base allows the selective deprotonation of an anionic imidazolium salt to form either a normal C-2 or an abnormal C-5 dianionic imidazolylidene lithium adduct. In solution, the abnormal NHC lithio-species slowly isomerizes to its thermodynamically more stable normal C-2 isomer. Furthermore, when treated with three equivalents of n-BuLi the monoanionic imidazolium salt produces a doubly deprotonated trianionic C-2, C-5 dilithium complex.
Figure 7:
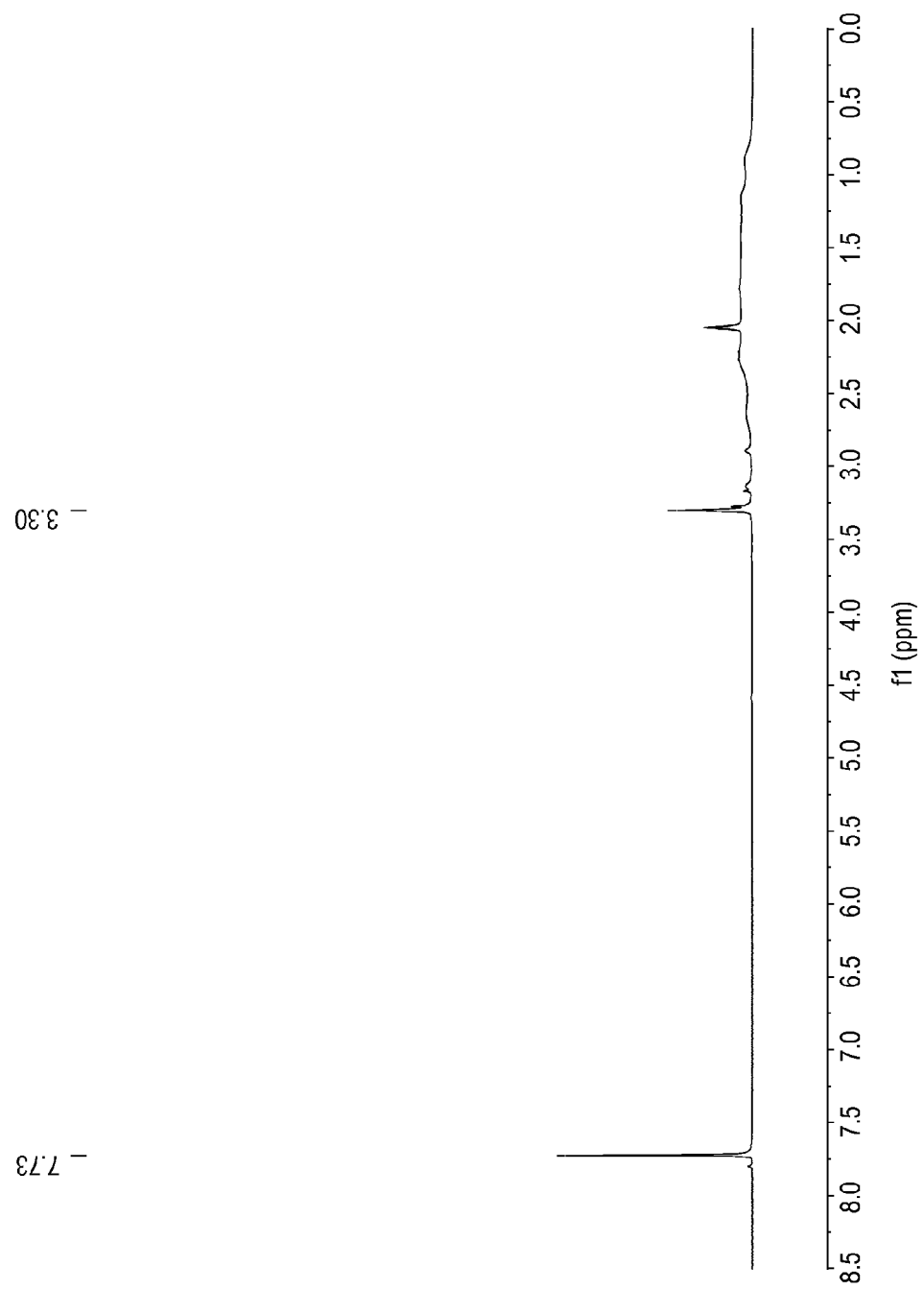
FIG. 7 shows $^1$H-NMR of crude 6($Cs^+$) in acetone-$d_6$ showing some MeOH at 3.30 ppm bound to the $Cs^+$ counter cations.
Figure 8:
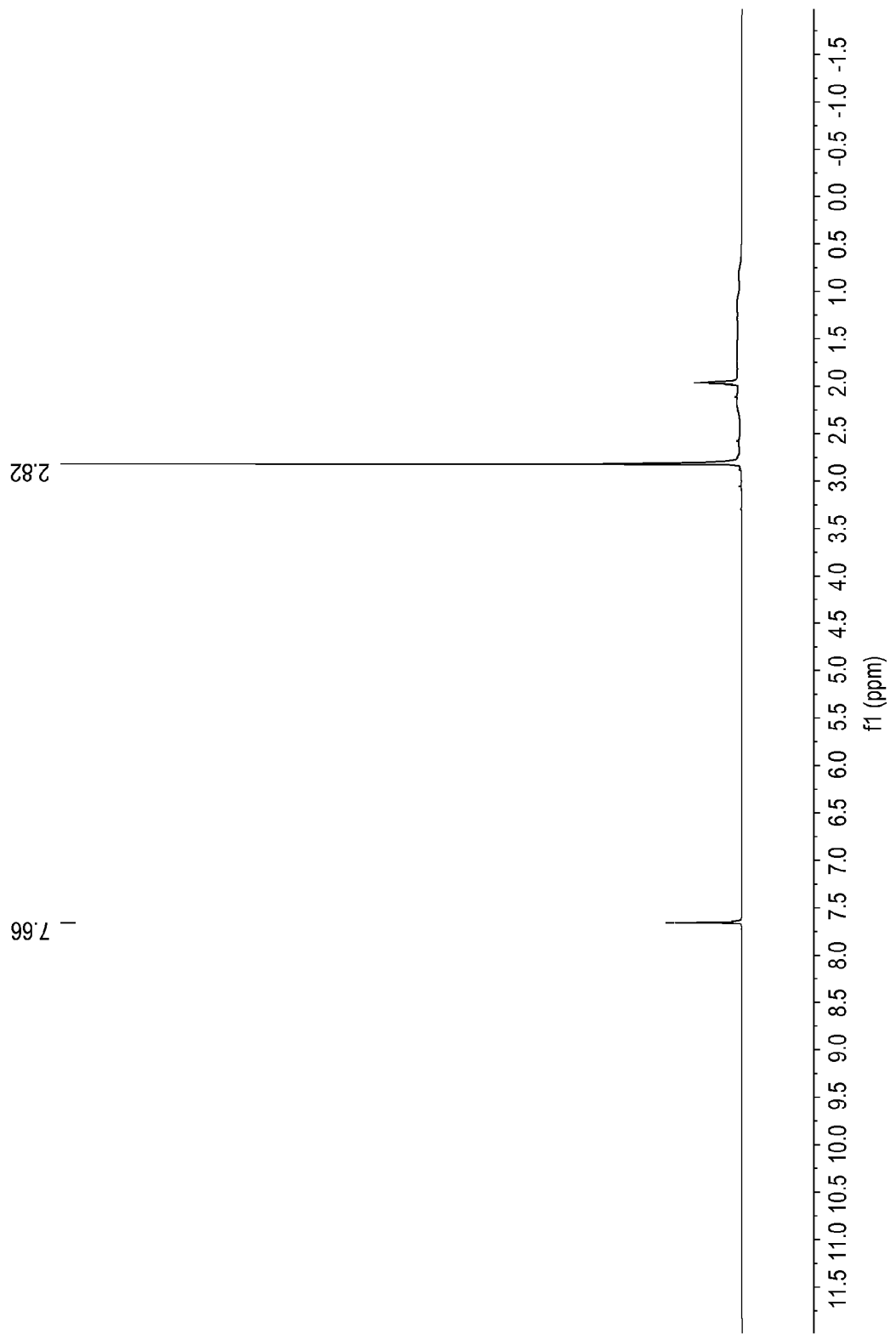
FIG. 8 shows $^1$H-NMR of 6($HNM_3^+$) in acetone-$d_6$ showing the dimine C—H resonance at 7.66 ppm and the $HNMe_3^+$ counter cation at 2.82 ppm (B—H resonances bm 3.11-0.50 ppm).
Figure 9:
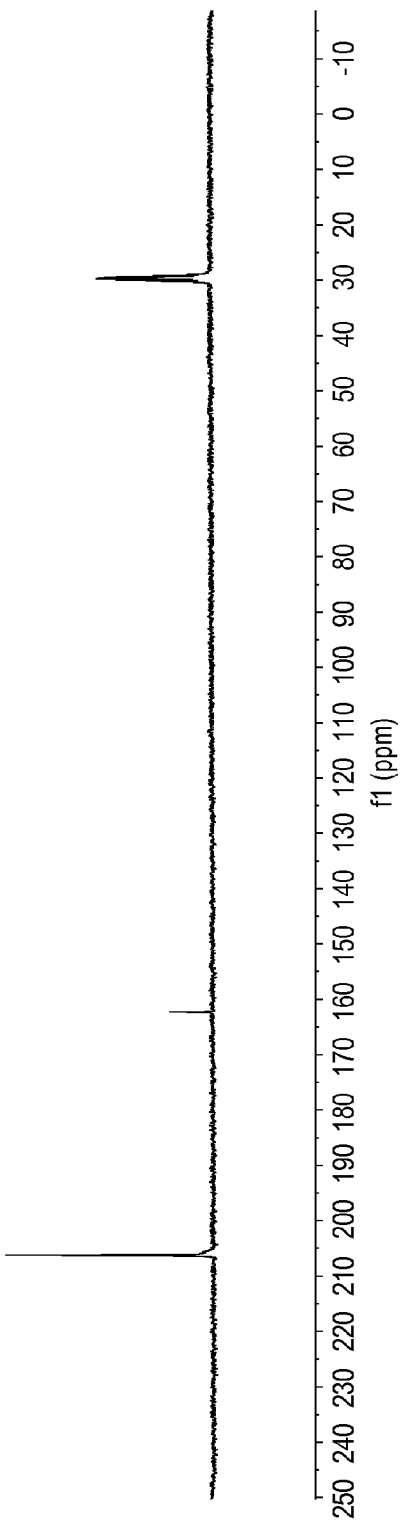
FIG. 9 shows $^{13}$C-($^1$H-dec) NMR of 6($Cs^+$) in acetone-$d_6$.
Figure 10:
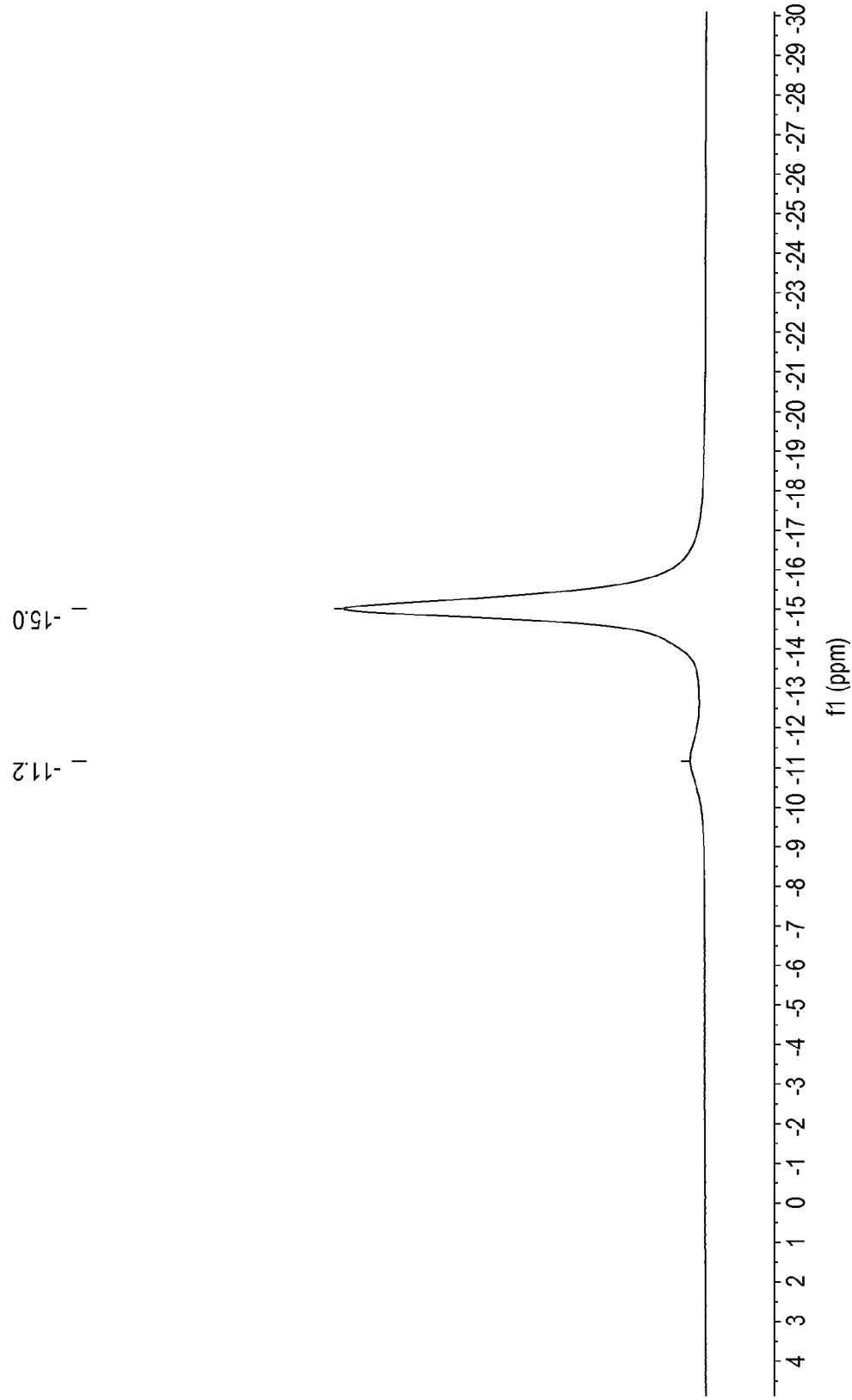
FIG. 10 shows $^{11}$B-($^1$H-dec) NMR of 6($Cs^+$) in acetone-$d_6$.
Figure 11:
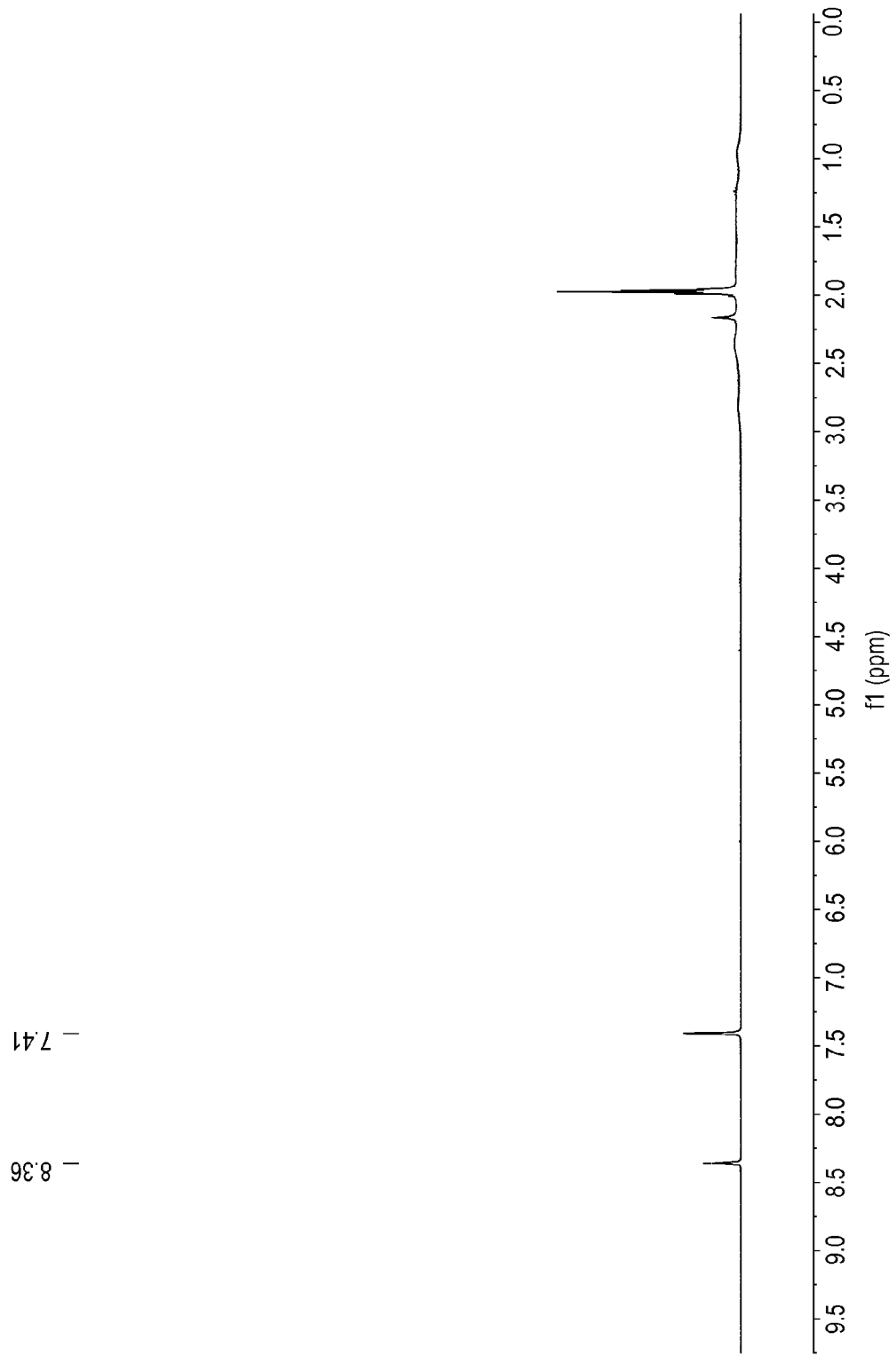
FIG. 11 shows $^1$H-NMR spectrum of 7($Cs^+$) in acetone-$d_6$.
Figure 12:
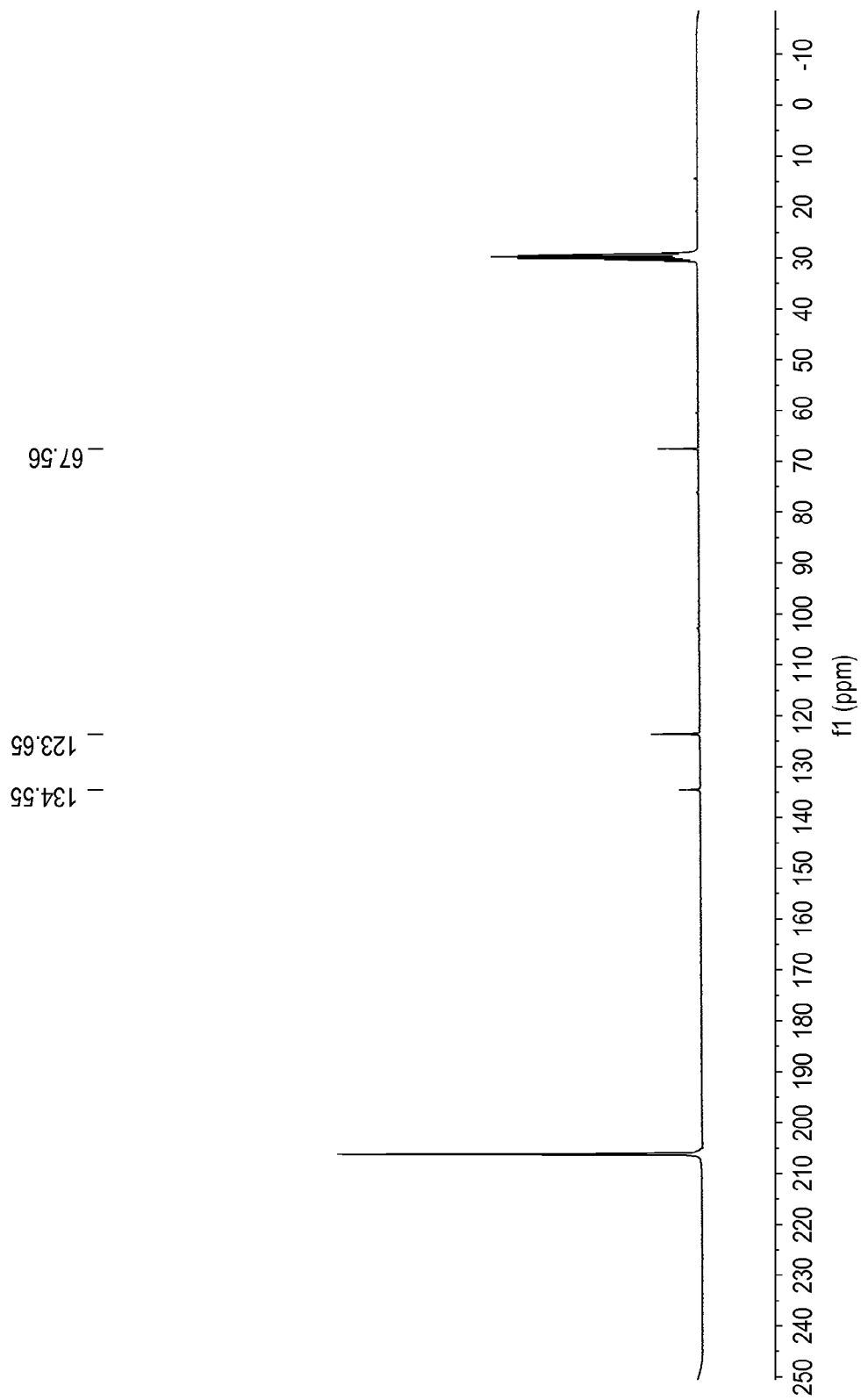
FIG. 12 shows $^{13}$C-($^1$H-dec)-NMR of 7($Cs^+$) in acetone-$d_6$.
Figure 13:
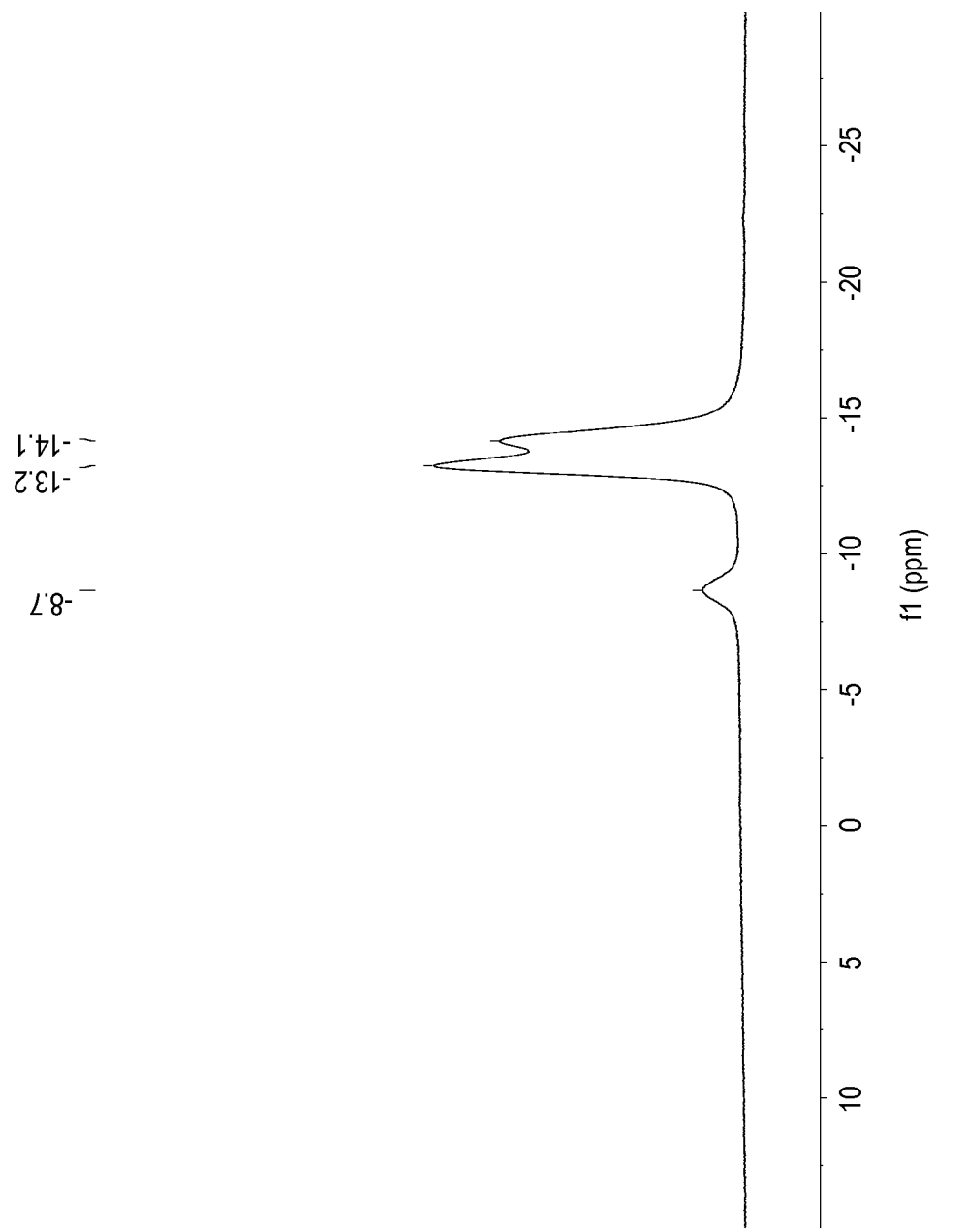
FIG. 13 shows $^{11}$B-($^1$H-dec) NMR spectrum of 7($Cs^+$) in acetone-$d_6$.
Figure 14:
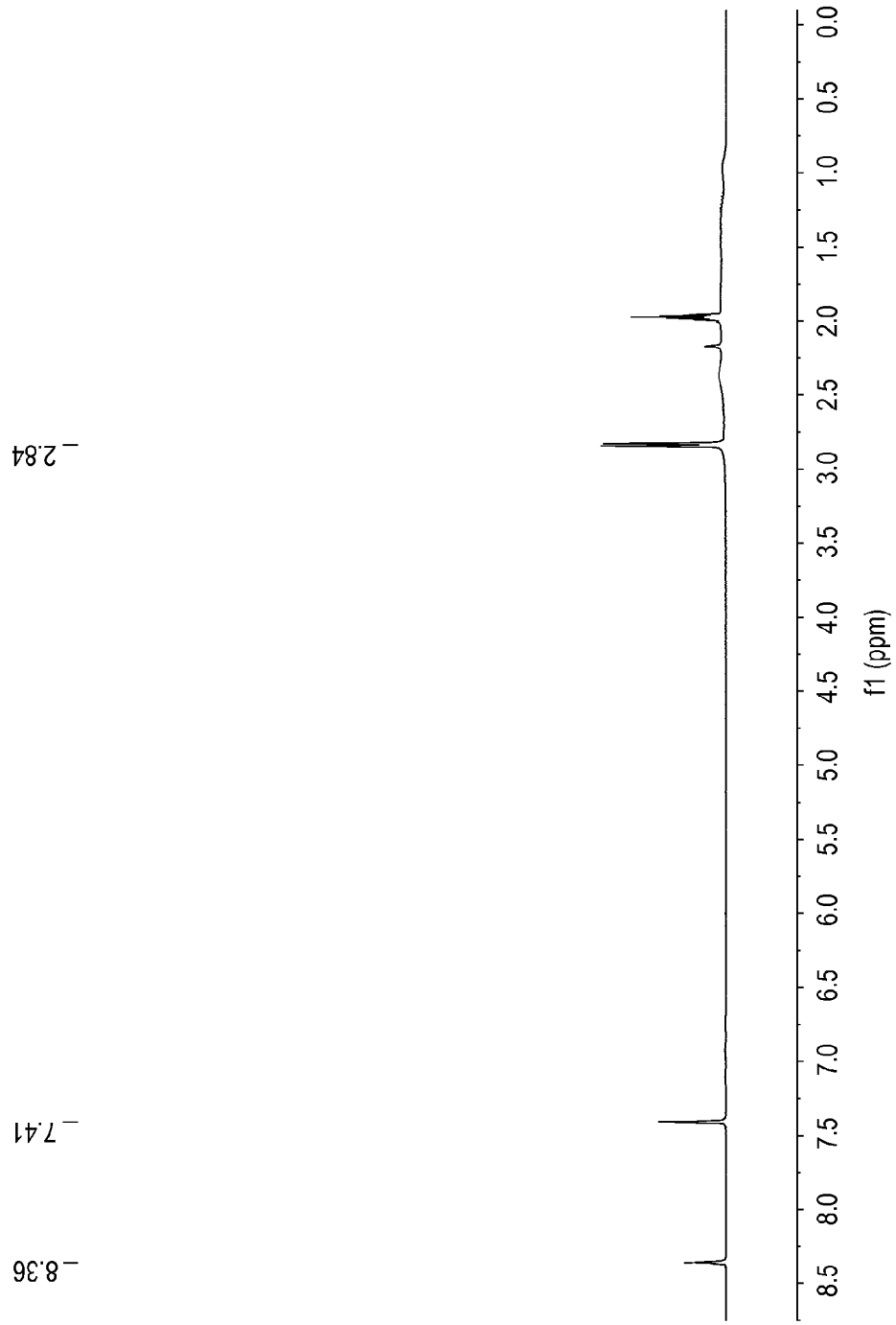
FIG. 14 shows $^1$H-NMR spectrum of 7($HNMe_3^+$) in acetone-$d_6$.
Figure 15:
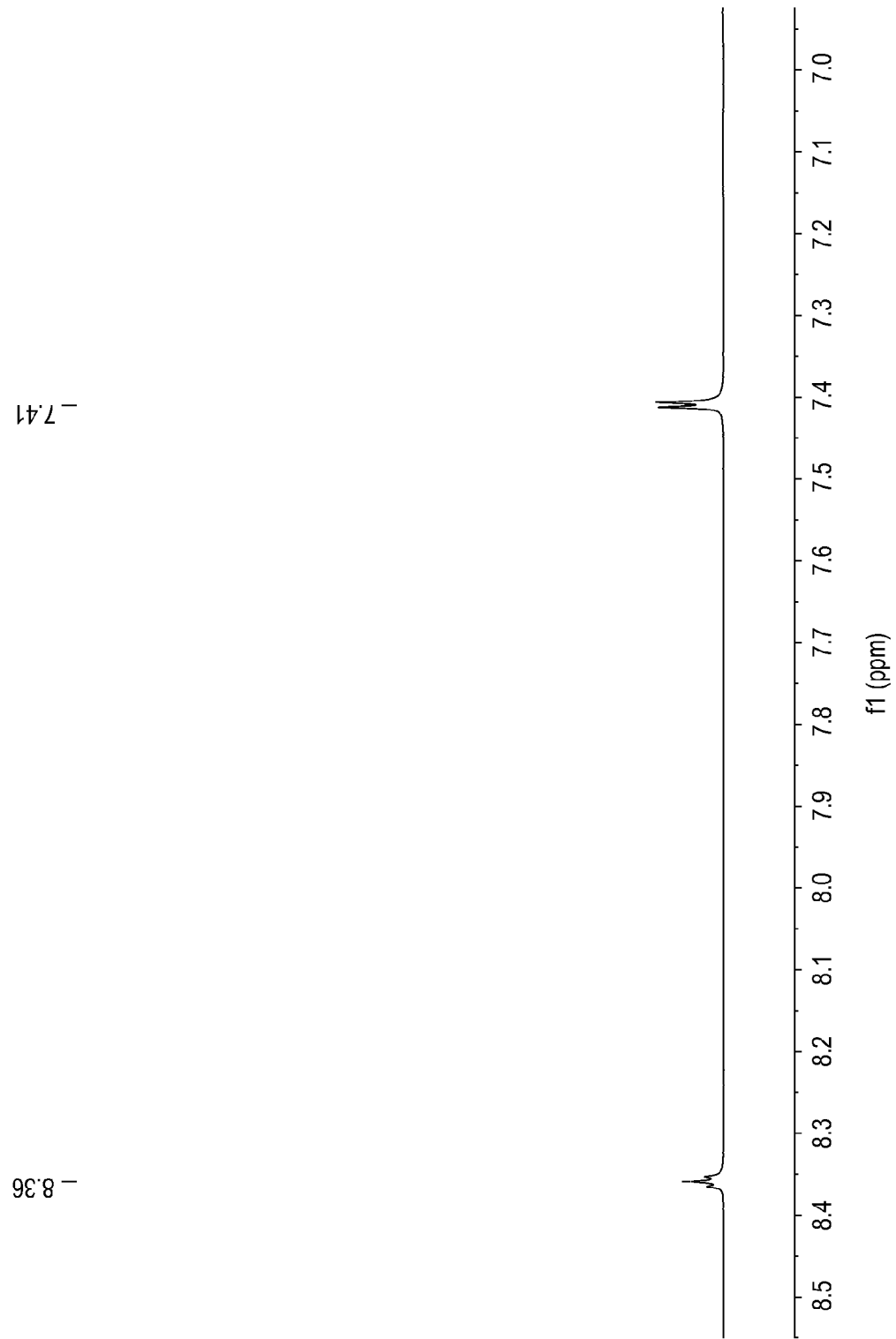
FIG. 15 shows An expanded view of the aromatic region of the $^1$H-NMR spectrum of 7($HNMe_3^+$) in acetone-$d_6$ showing the small $^4$J(H,H) coupling through the imidazolium ring.
Figure 16:
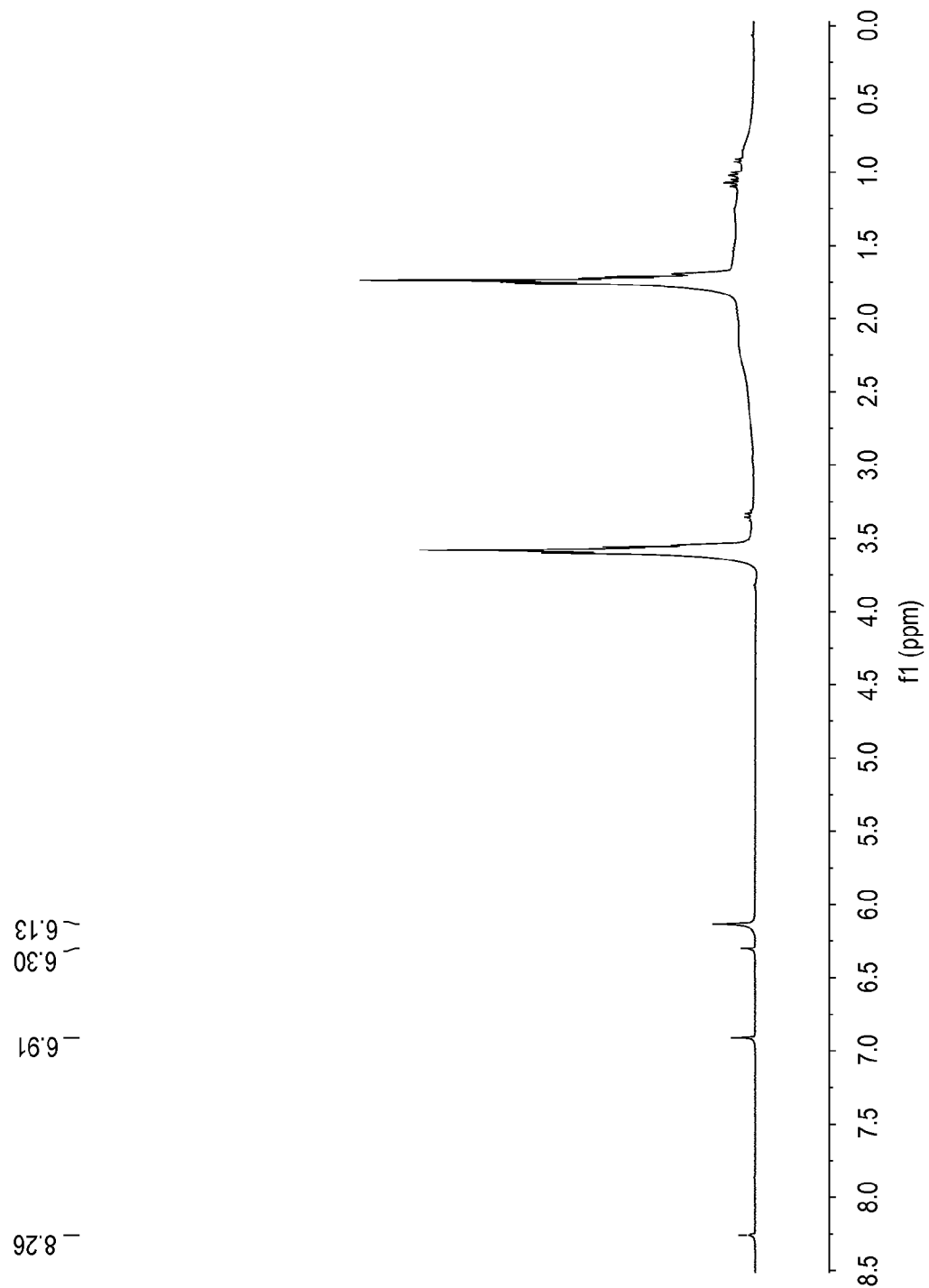
FIG. 16 shows $^1$H-NMR spectrum of a mixture of 8, 9 and 10 in THF-$d_8$.
Figure 17:
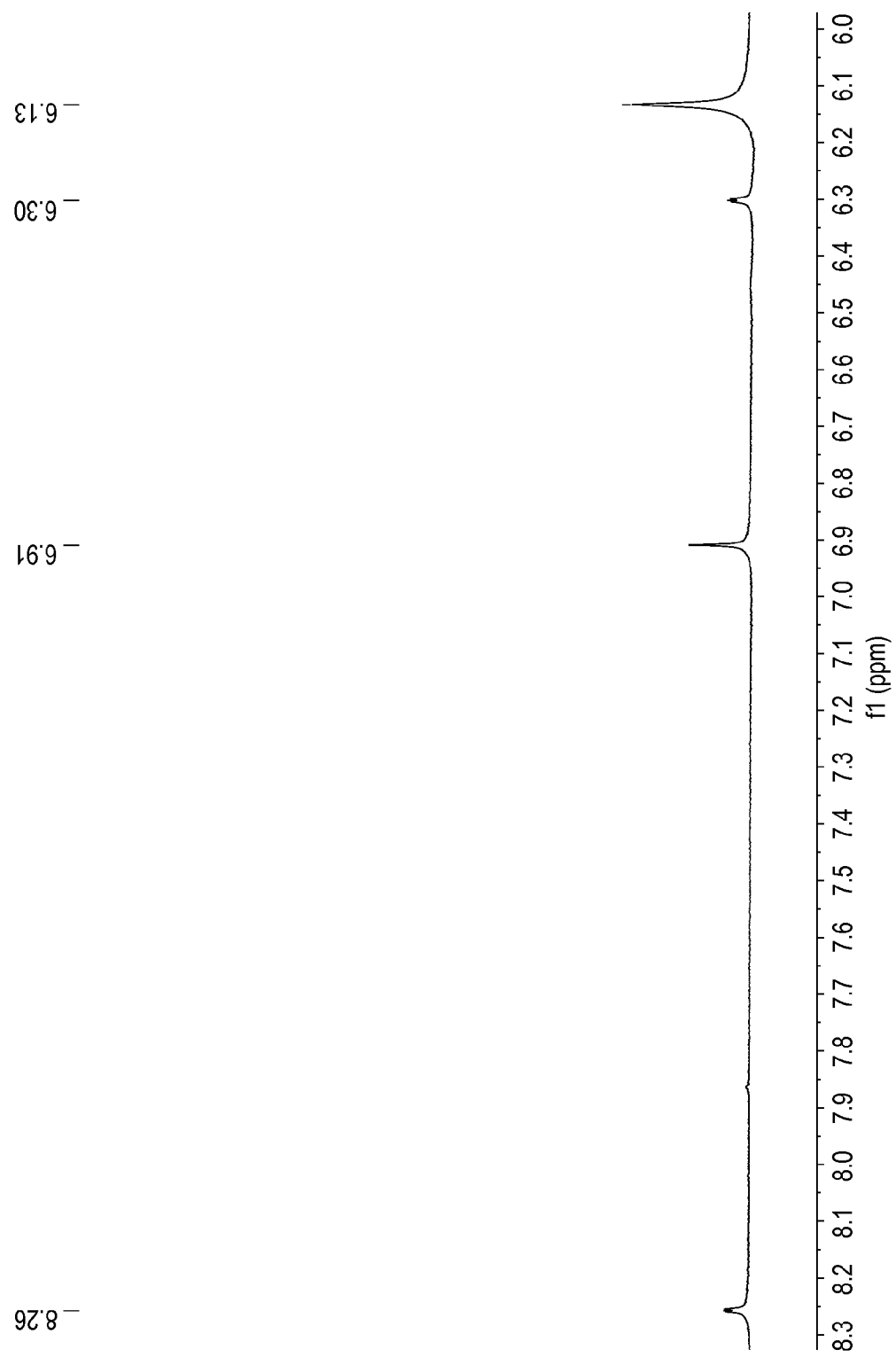
FIG. 17 shows An expanded view of the aromatic region of the $^1$H-NMR of a mixture of 8, 9 and 10 in THF-$d_8$
Figure 18:
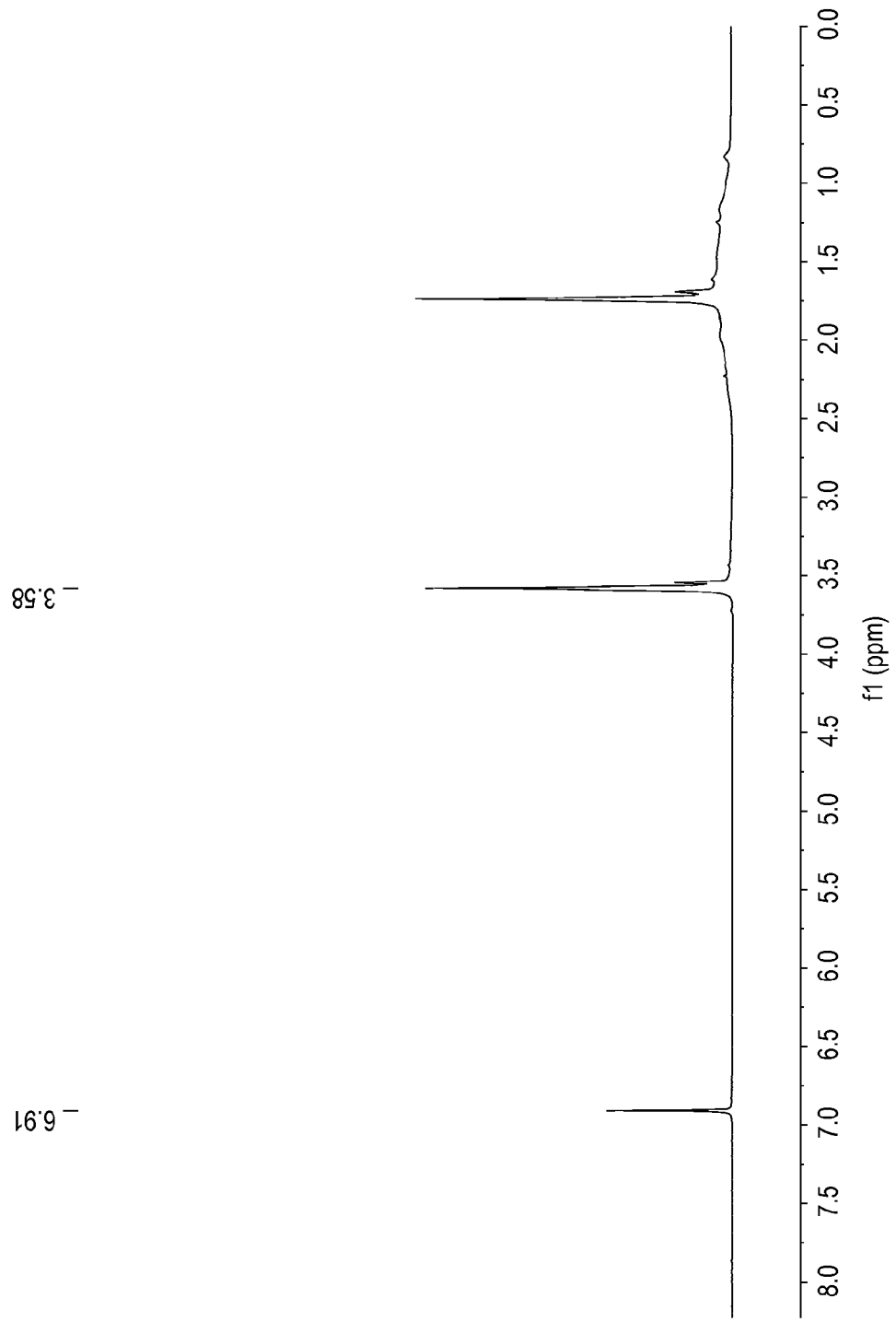
FIG. 18 shows $^1$H-NMR spectrum of 8 in THF-$d_8$, showing coordinated and free THF.
Figure 19:
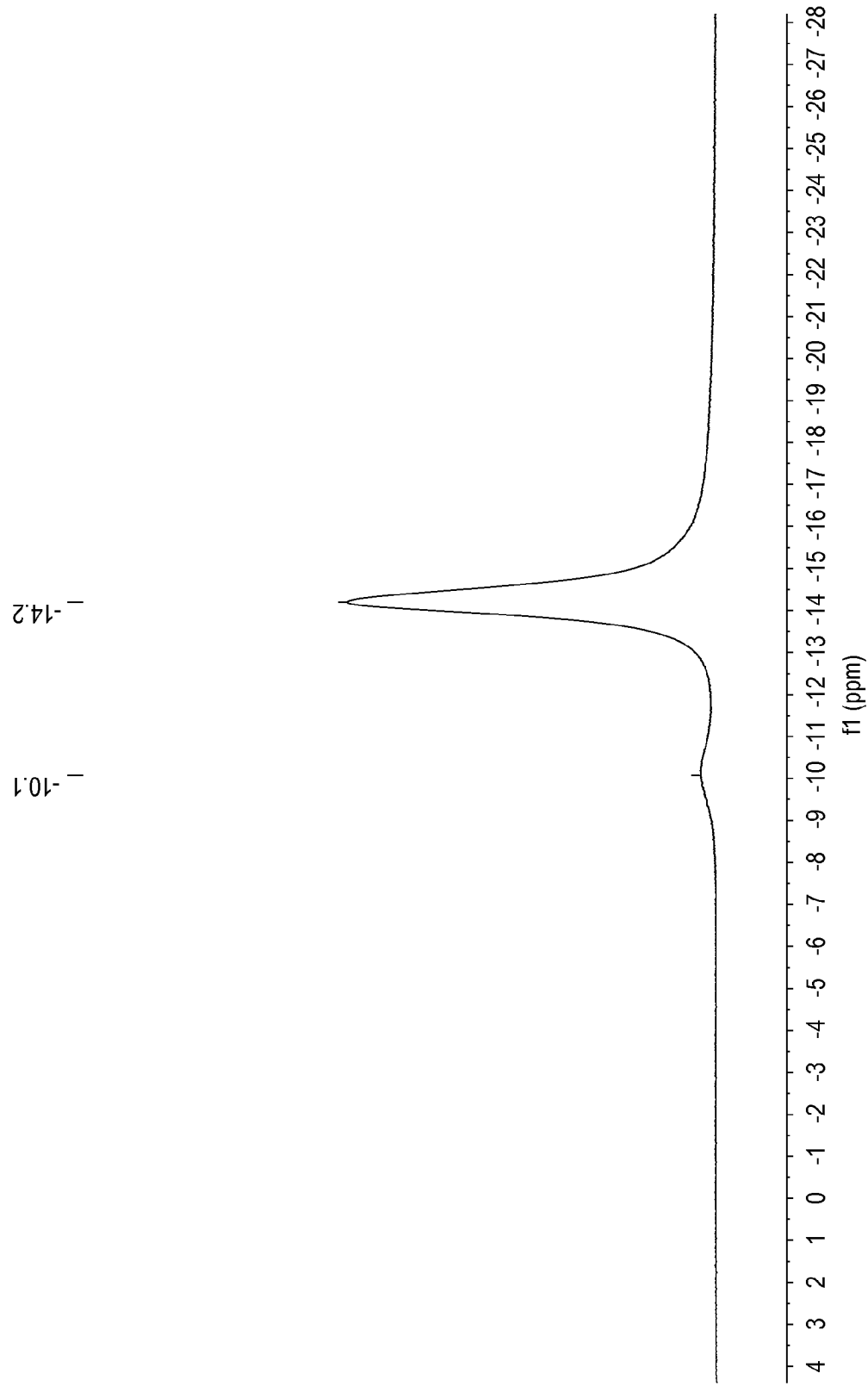
FIG. 19 shows $^{11}$B-($^1$H-dec)-NMR spectrum of 8 in THF-$d_8$.
Figure 20:
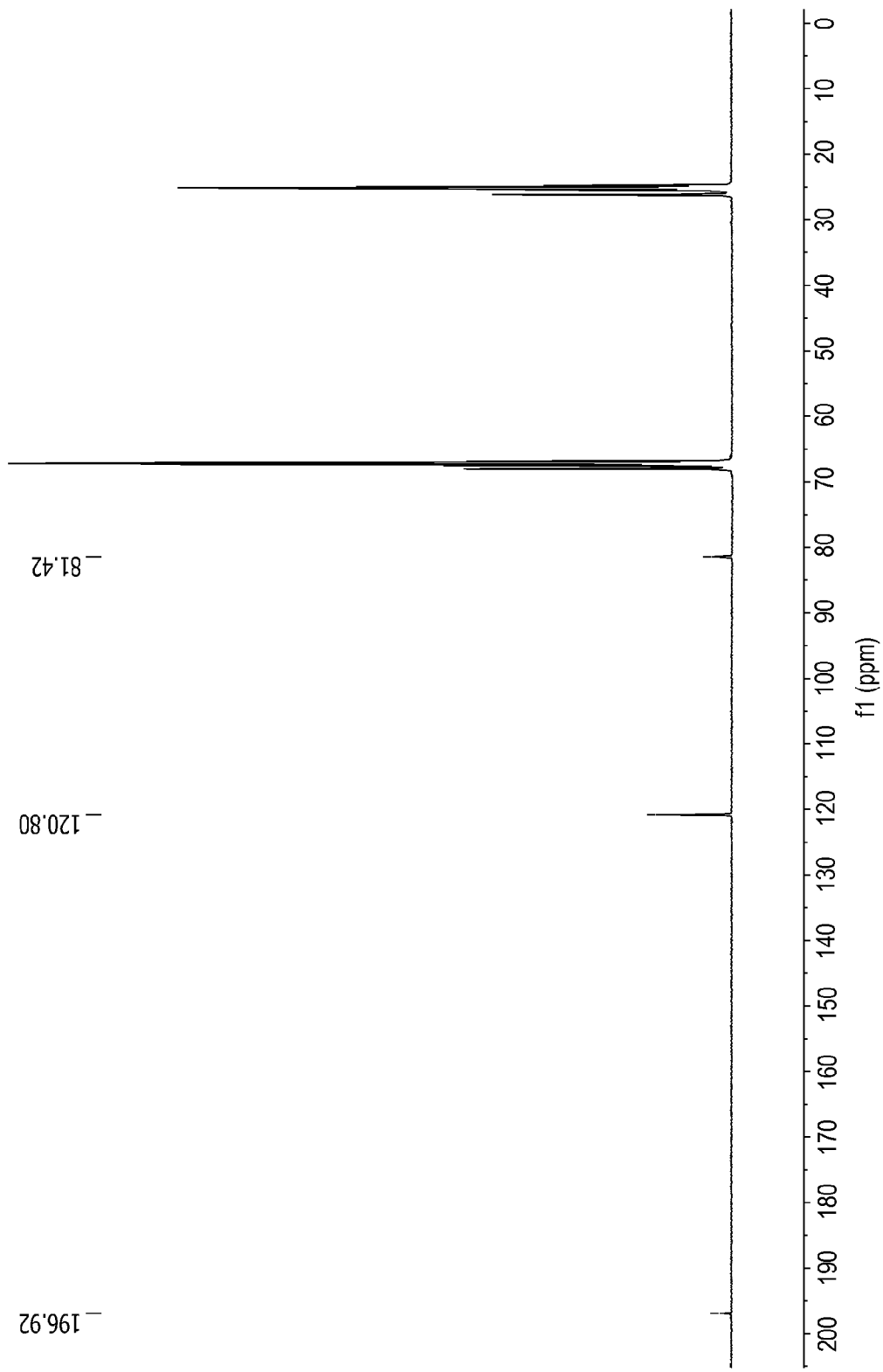
FIG. 20 shows $^{13}$C-($^1$H-dec)-NMR spectrum of 8 in THF-$d_8$.
Figure 21:
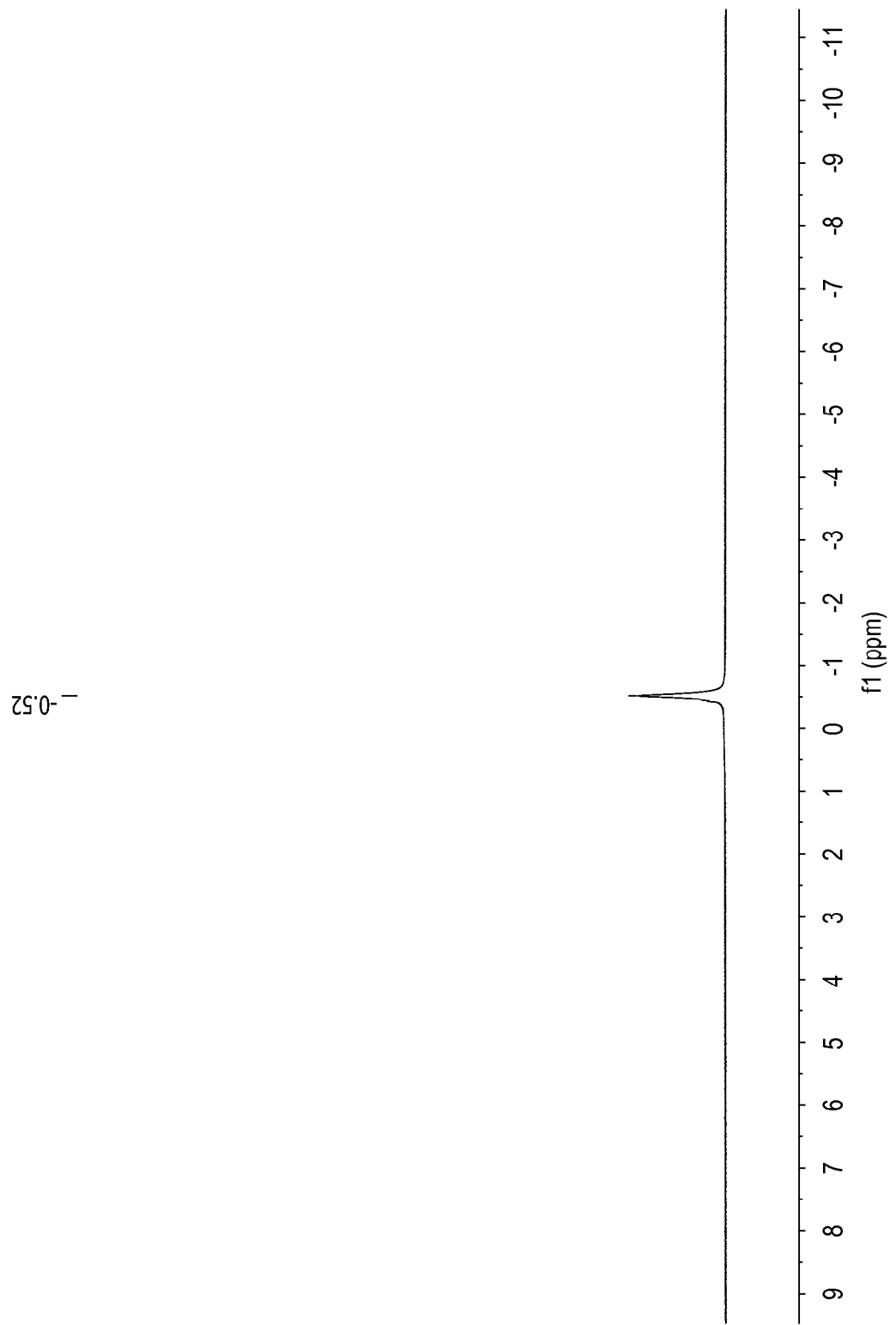
FIG. 21 shows $^7$Li-NMR spectrum of 8 in THF.
Figure 22:
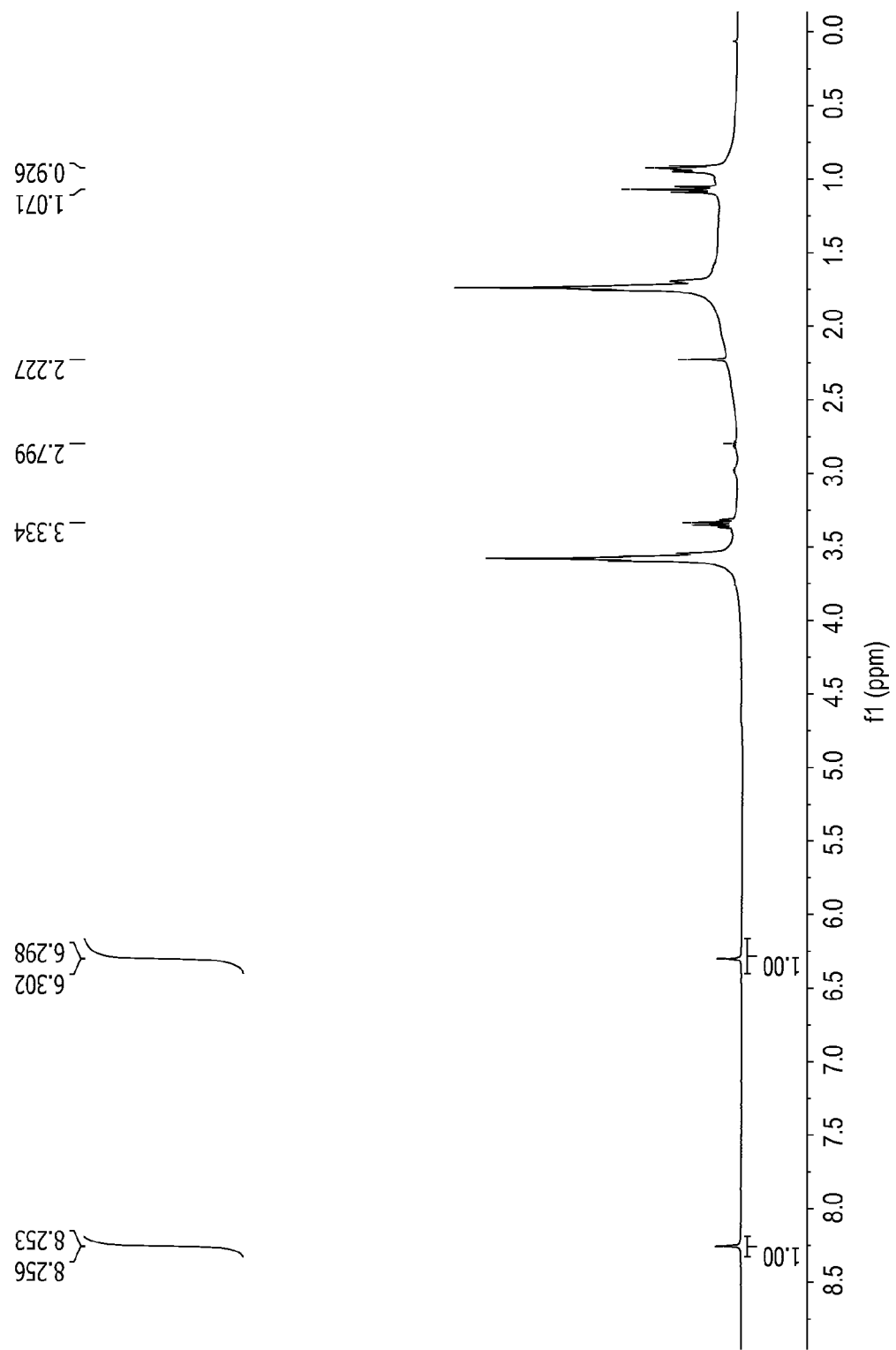
FIG. 22 shows $^1$H-NMR of 9 in THF-$d_8$. Note that diisopropylamine, trimethylamine, THF and $Et_2O$ molecules are bound to the lithium counter cation.
Figure 23:
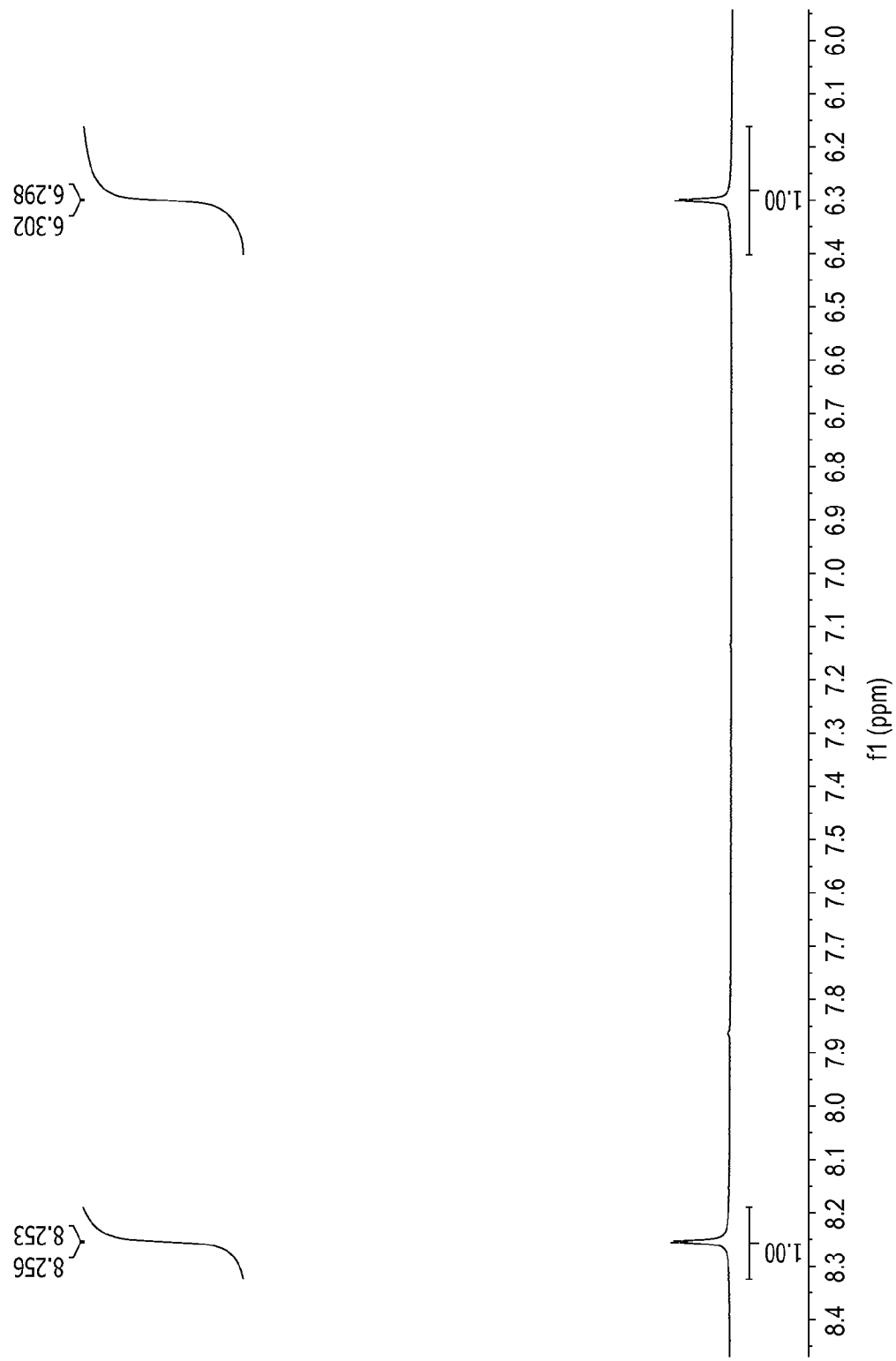
FIG. 23 shows An expanded view of the aromatic region of the $^1$H-NMR of 9 in THF-$d_8$, showing the small J-coupling of the two protons across the imidazolium ring.
Figure 24:
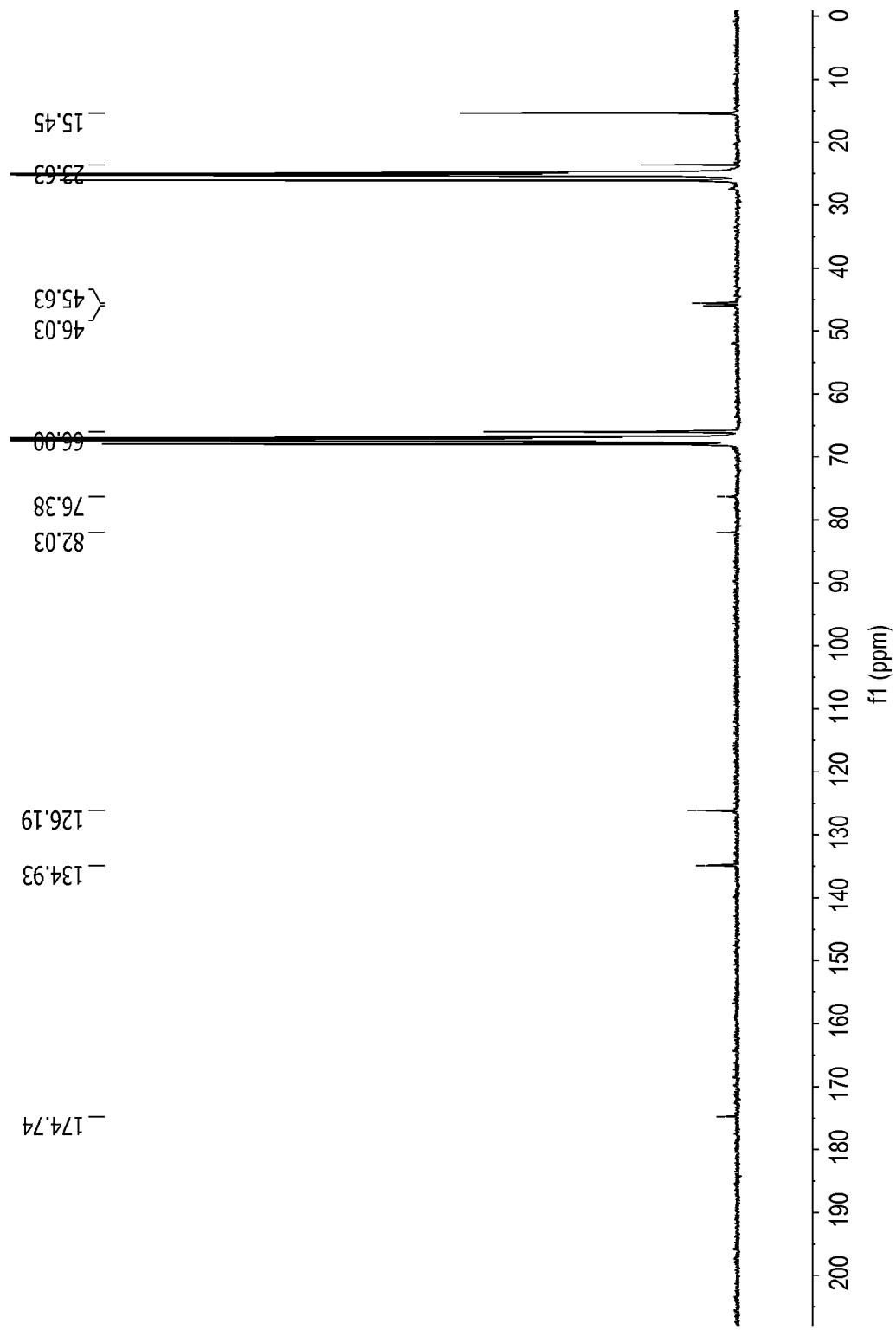
FIG. 24 shows $^{13}$C-($^1$H-dec) NMR spectrum of 9 in THF-$d_8$.
Figure 25:
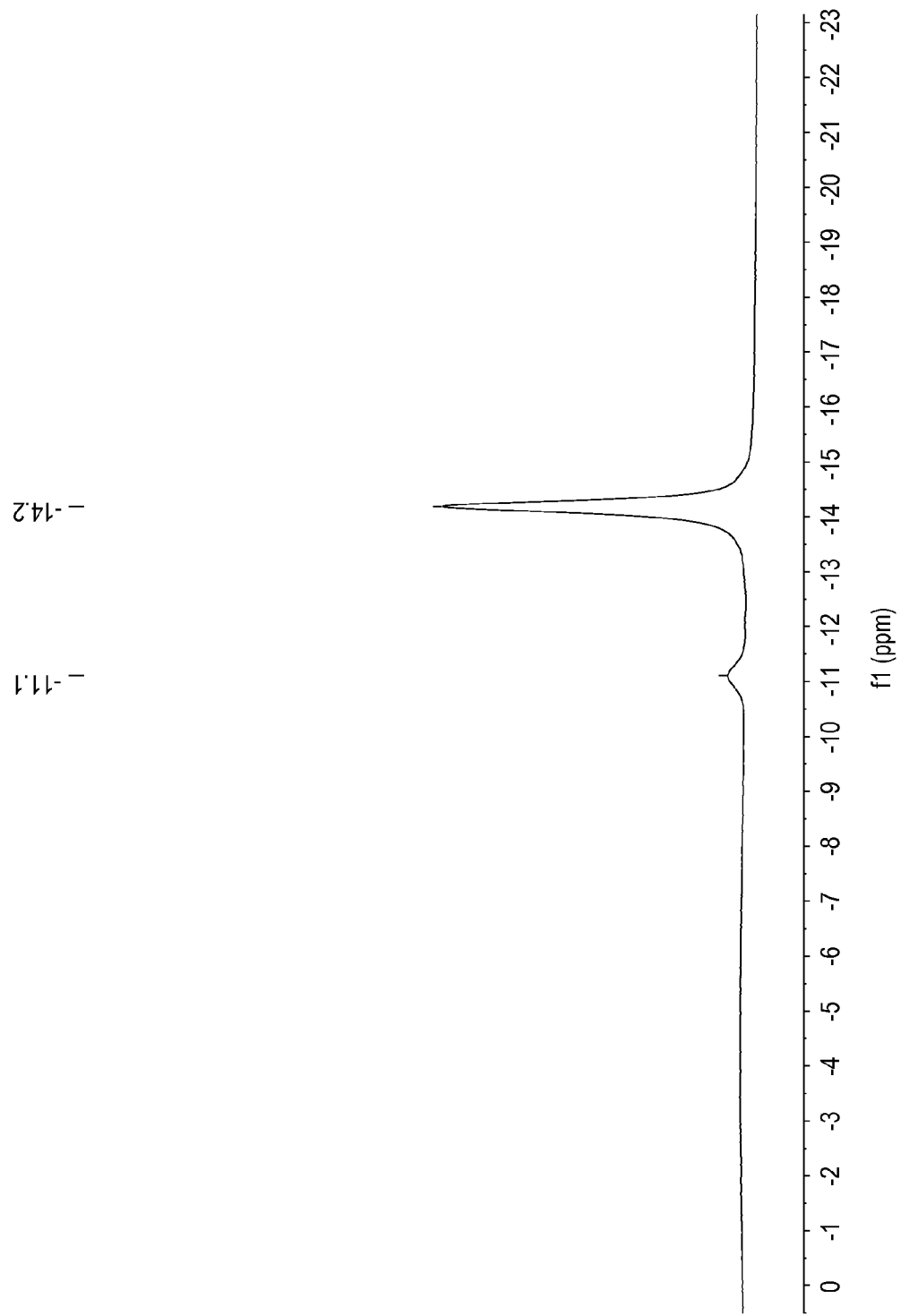
FIG. 25 shows $^{11}$B-($^1$H-dec)-NMR of 9 in THF-$d_8$.
Figure 26:
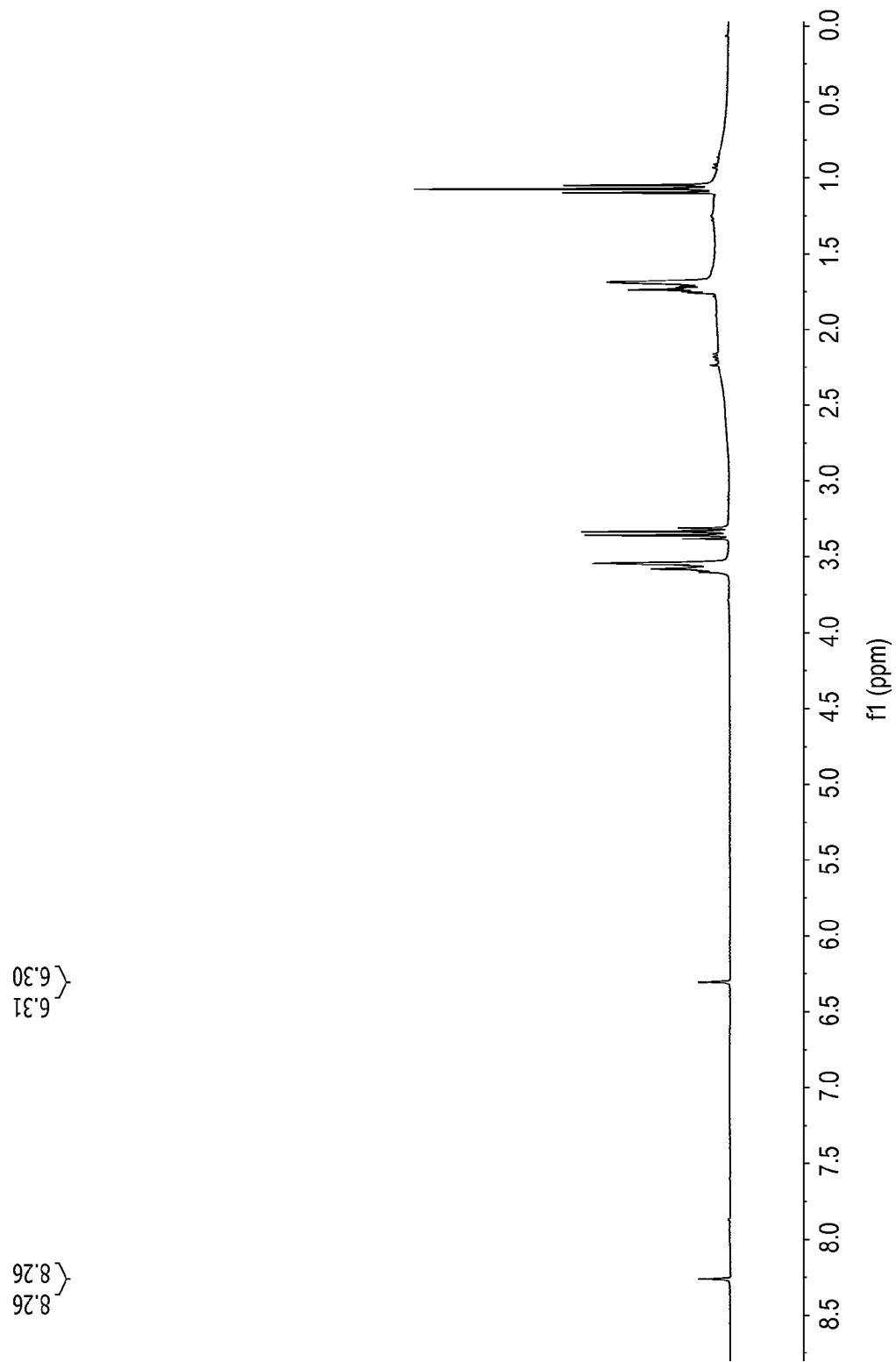
FIG. 26 shows $^1$H-NMR of 9 in THF-$d_8$, after precipitation in ether and removal of the trace amines.
Figure 27:
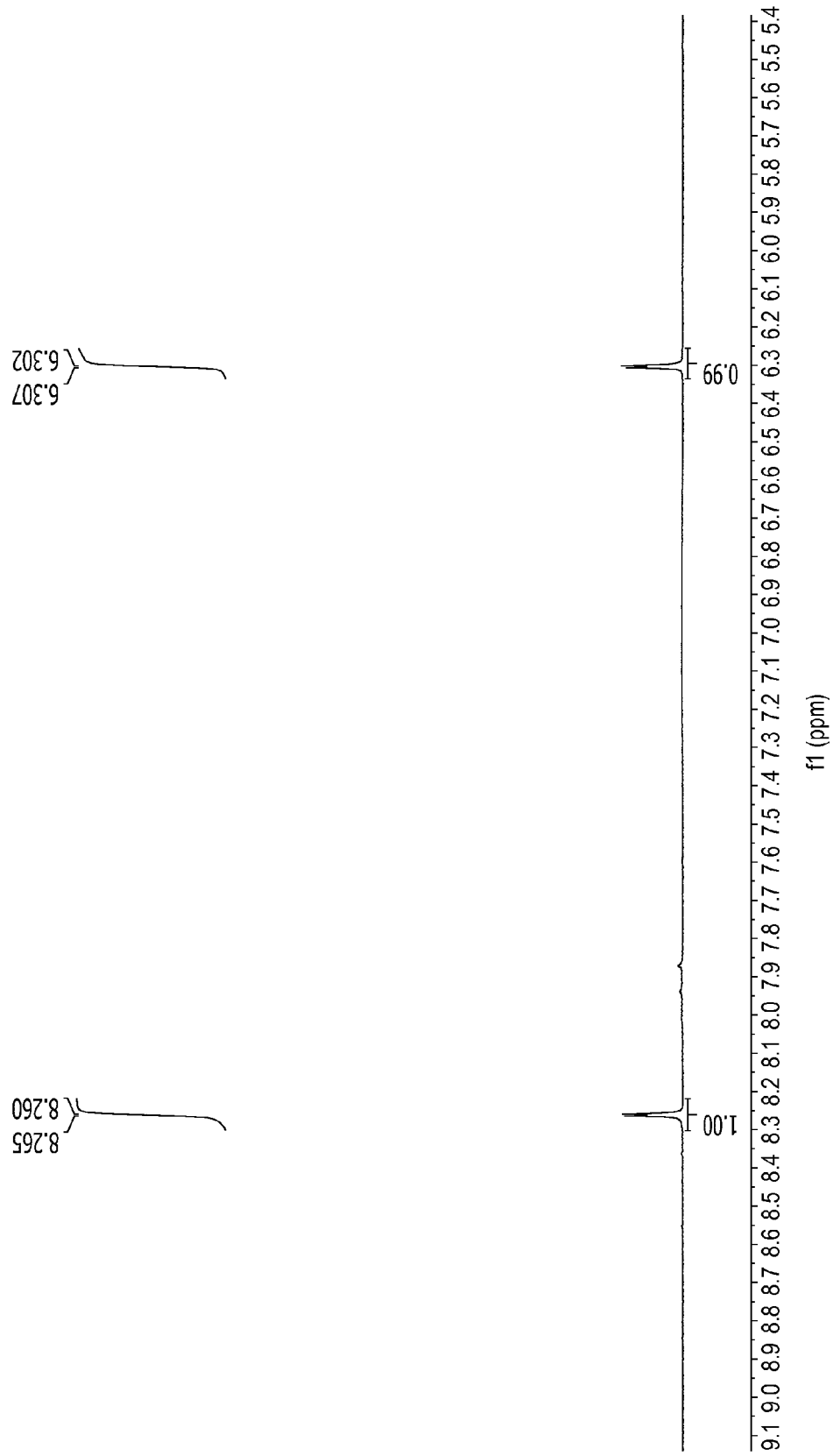
FIG. 27 shows An expanded view of the $^1$H-NMR aromatic region of 9 in THF-$d_8$, after precipitation in ether and removal of the trace amines.
Figure 28:
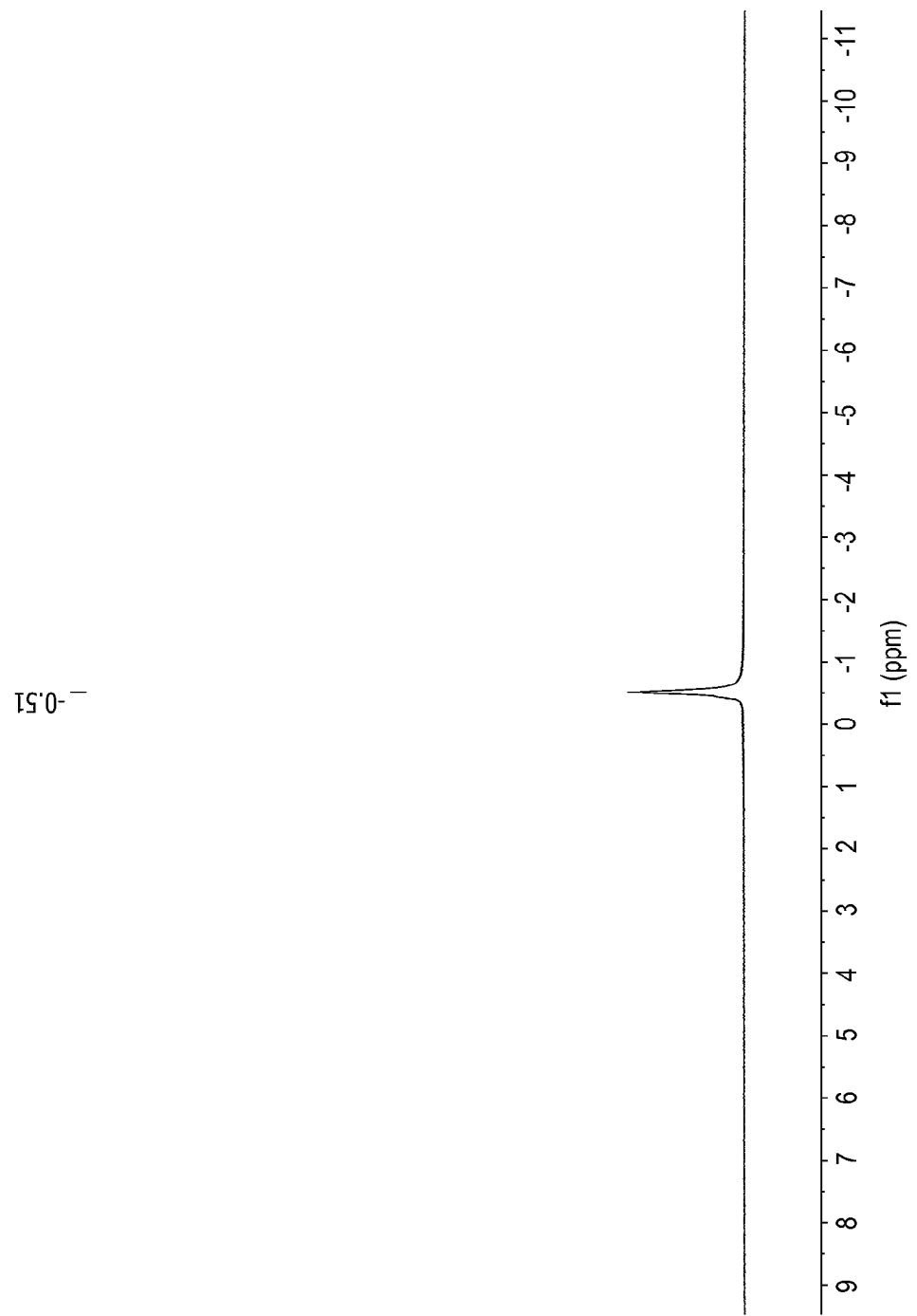
FIG. 28 shows $^7$Li-NMR spectrum of 9 in THF.
Figure 29:
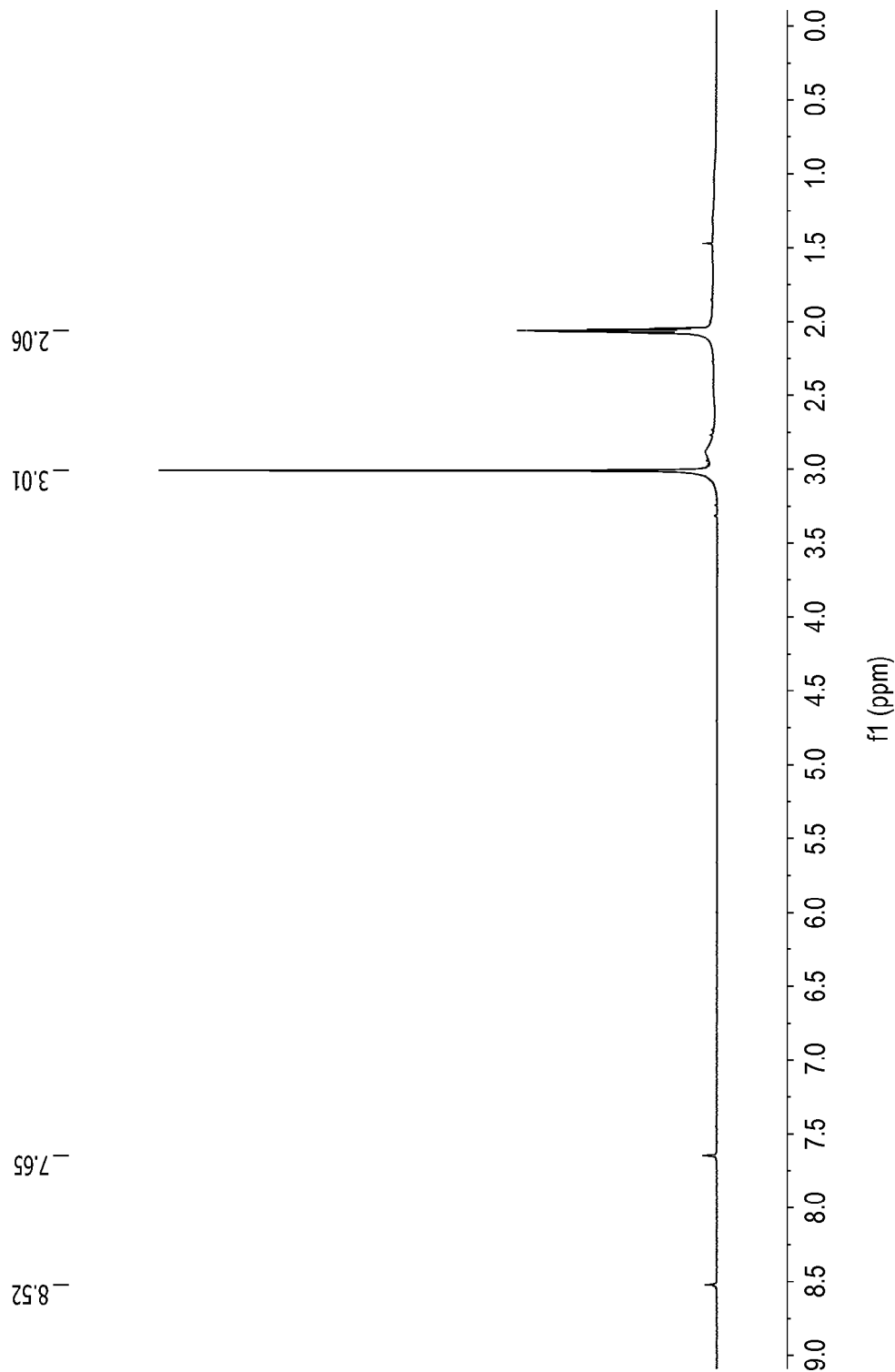
FIG. 29 shows $^1$H-NMR of $7_D$($HNMe_3^+$) in acetone-$d_6$
Figure 30:
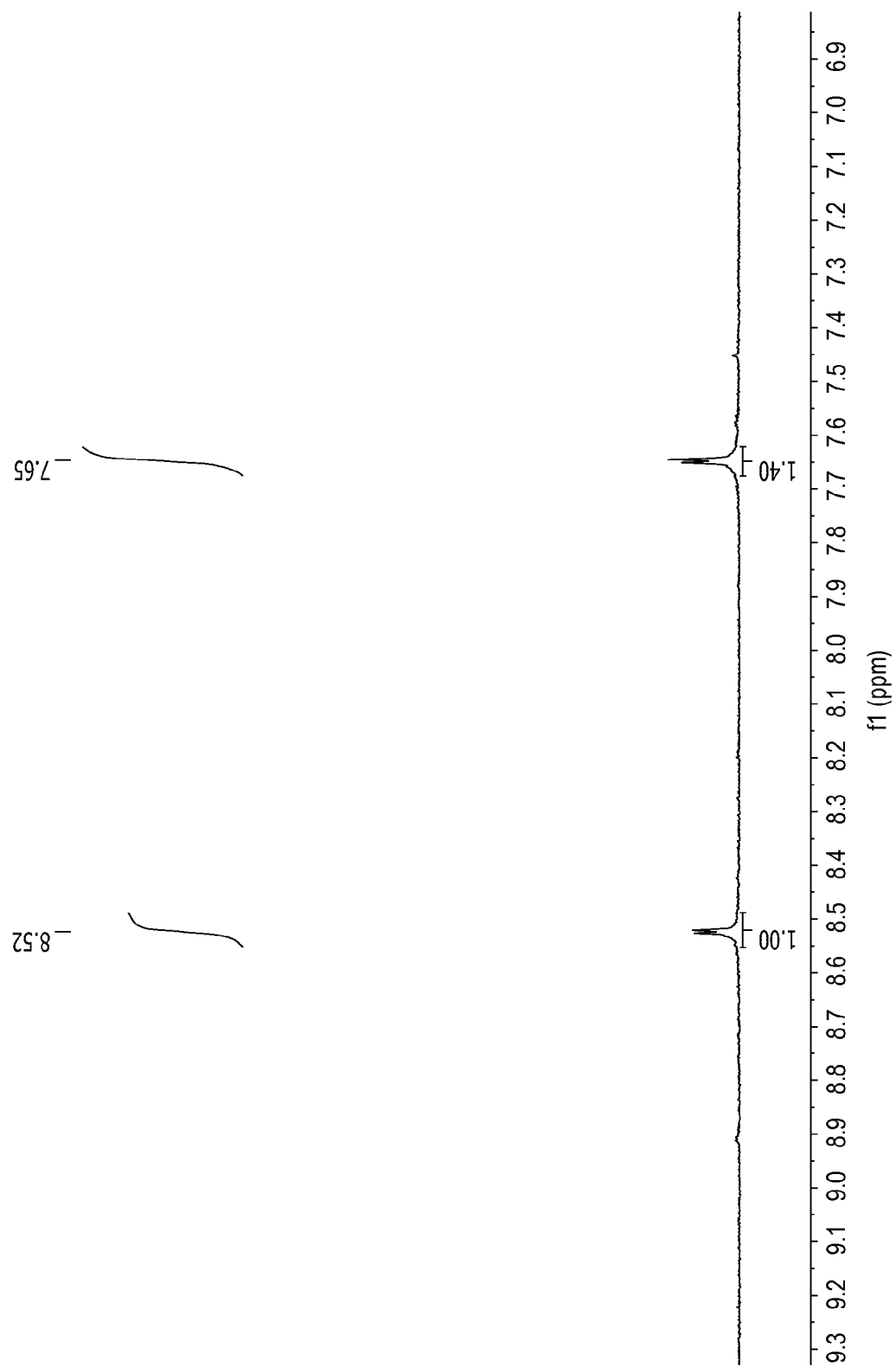
FIG. 30 shows a blow up of the $^1$H-NMR aromatic region of $7_D$($HNMe_3^+$) in acetone-$d_6$. Approximately 83% deuterium incorporation at C-5 is observed based on integration of the two doublets in the aromatic region. The doublet at 7.65 contains a small amount of overlapping C-2 deuterated product (singlet in the $^1$H NMR), which increases the height of the right hand side of the peak (and the area). Subtraction of this extra area and dividing by 2 (two protons for the C-2 imidazolium) gives the total area of 1.2. Thus, 1/1.2×

Next, isolation of the trianionic doubly deprotonated C-2/C-5 species 10, which can be cleanly formed (98% yield) by the treatment of 7 with three equivalents of n-BuLi, was studied. The $^{13}$C NMR of 10 showed an unsymmetrical imidazolium ring with two low field quaternary resonances at 195.6 and 169.5 ppm that correspond to the C-2 and C-5 carbon centers, respectively, as well as signals (89.1, 83.0 ppm) for the inequivalent hypercoordinate carborane carbons. Interestingly, two overlapping resonances appeared in the $^7$Li NMR spectrum of 10 (−0.18, −0.21 ppm), which suggests that both the C-2 and C-5 centers of the molecule are complexed to alkali cations. Indeed, a single crystal X-ray diffraction study showed that in the solid-state 10 is dimeric with the C-2 center bound to a single lithium cation, and the C-5 center bridging two other lithium cations (FIG. 5). The central heterocyclic ring bond lengths of 10 (N1-C2=1.364(3), N3-C2=1.353(3), N1-C5=1.429(3), C5-C4=1.363(3), C4-N3=1.402(3) Å) were similar (N1-C2=1.375(3), N3-C2=1.361(3), N1−O5=1.442(4), C5-C4=1.356(4), C4-N3=1.399(4) Å) to those reported by Robinson[8a] for an N-aryl substituted monoanionic C2/C-5 deprotonated species. The carborane nitrogen bond lengths of (N1-C7=1.448(3), N3-C6=1.446(3) Å) and carborane boron distances in the cluster (average C-B distances for carboranes 1.724(3), 1.712(3) Å) were nearly identical to imidazolium anion 7 and the normal C-2 dianionic carbene lithium adduct 8, indicating no disruption of the icosahedral carborane cluster. The C-2 carbon Li1 bond length of 2.103(4) was slightly shorter than the C-5 Li2 distance (2.157(5) Å), which can be attributed to the 3-center-2-electron nature of the latter interaction. [19] Several close B—H contacts with the lithium cations (H1-Li1=2.05, H2-Li1=2.16, H3-Li2=2.14 Å) suggest the occurrence of multiple agostic-like interactions.

As described herein, it is possible to prepare unusual families of multiply charged carbene lithium complexes that are fused to carborane anions. These results indicate that the carba-closo-dodecaborate anion is not simply a substitute for alkyl and aryl groups, but leads to superior control of carbene formation and the unique ability to allow the isolation of lithium complexes of two NHC constitutional isomers as well as a trianionic C-2/C-5 deprotonated species from a single precursor. Since the carba-closo-dodecaborate anion can be readily functionalized with a variety of substituents,[9a] this strategy paves the way for the development of a broad new generation of polyanionic N-heterocyclic carbenes with distinct steric and electronic profiles.

In some embodiments, the invention provides a process for preparing a compound according Formula (H):

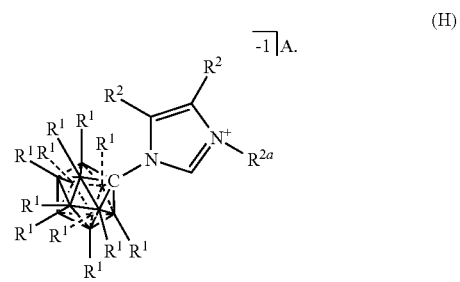

The process for preparing a compound according to Formula (H) includes condensing a compound according to Formula (A):

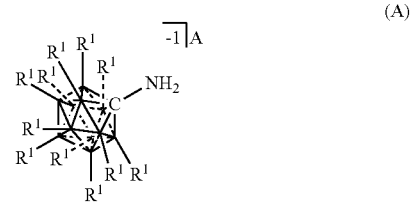

with a compound according to Formula (J):

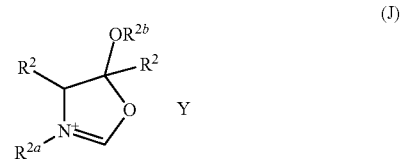

under conditions sufficient to form the compound of Formula (H).

In processes for preparing a compound according to Formula (H), each unlabeled vertex bonded to R$^1$ represents a boron atom; each R$^1$ and each R$^2$ is independently selected from H, halogen, alkyl, aryl, silyl, siloxy, alkoxy, aryloxy, haloalkyl, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, and nitro; wherein each alkyl, aryl, silyl, siloxy, alkoxy, and aryloxy is optionally substituted with a member independently selected from halogen, hydroxyl, hydroxide, haloalkyl, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxyl, nitro, and alkoxy; $R^{2a}$ is selected from alkyl and aryl; $R^{2b}$ is selected from —C(O)-alkyl and —C(O)-aryl; A is a cation; and Y is an anion.

In some embodiments, the invention provides processes for preparing a compound according to Formula (H) wherein each $R^1$ and each $R^2$ is independently selected from H, halogen, alkyl, aryl, silyl, siloxy, alkoxy, and aryloxy; wherein each alkyl, aryl, silyl, siloxy, alkoxy, and aryloxy is optionally substituted with a member independently selected from halogen, hydroxyl, and hydroxide; $R^{2a}$ is selected from alkyl and aryl; and $R^{2b}$ is selected from —C(O)-alkyl and —C(O)-aryl.

Zwitterionic imidazolium species 23 can be prepared according to methods of the invention by reacting the mesityl substituted oxazolinium cation 23a with anionic carboranyl amine 7, followed by treatment with acid (FIG. 37, top). The reaction sequence is effective, affording the imidazolium species 23 in 77% yield based on the carboranyl amine. The zwitterion is soluble in benzene as well as most other common solvents, with the exception of alkanes and $H_2O$. The $^1H$ NMR spectrum of 23 shows three distinct doublets of doublets for the imidazolium ring protons (8.8 ppm, $^4J_{H-H}$=2.0, 1.8 Hz, (C-2); 7.7 ppm, $^3J_{H-H}$=2.0 Hz, $^4J_{H-H}$=1.8 Hz, (C-4); 7.3 ppm, $^4J_{H-H}$=2.0 Hz, $^3J_{H-H}$=2.0 Hz, (C-5)). Assignment of the imidazolium backbone protons was determined by NOESY NMR experiments that show coupling between the resonance at 7.7 ppm and the B—H pentagonal belt adjacent to the carborane carbon. In addition, through-space coupling is observed between the signal at 7.3 ppm and the ortho-mesityl methyl protons. The $^{13}C$ NMR spectrum of 23 displays three resonances (142.0 (C-2), 124.7 (C-4), 124.8 (C-5) ppm) for the imidazolium carbons.

Deprotonation of the zwitterionic imidazolium species 23 with LiHMDS dissolved in THF results in rapid precipitation of a white powder 27. Analysis of the material by $^1H$ NMR showed the disappearance of the low field C-2 proton at 8.8 ppm and the appearance of two doublets (7.4 ppm and 6.8 ppm; d, $^3J_{H-H}$=1.5 Hz), which is consistent with the formation of the normal C-2 NHC. The $^{13}C$ NMR spectrum of 27 displayed a broad resonance at 199.9 ppm for the carbene center, which is in the expected range for aryl substituted imidazolylidenes and very close to the lithium complex of NHC 8 shown in FIG. 2 (195.0 ppm). Interestingly, deprotonating 23 with KHMDS in lieu of LiHMDS, results in the formation of 28, which is very soluble in THF and benzene. The $^1H$ NMR spectrum of 28 is nearly identical to 27, however the $^{13}C$ NMR spectrum reveals a downfield shifted carbene resonance (211.1 ppm). The difference in chemical shift compared to 27 is likely due to the formation of an NHC Li$^+$ complex in solution, whereas the K$^+$ salt 28 exists as a solvent separated ion pair. The $^7Li$ NMR of 27 shows a broad resonance at 2.3 ppm, which also supports the formation of a NHC Li$^+$ adduct in solution. Our hypothesis is in line with previous studies[24, 25] that have shown that alkali metal free NHCs are formed when K bases are implemented in lieu of Li reagents.

The solid-state structure of 27 was unambiguously determined by a single crystal X-ray diffraction study, and shows the NHC and three THF molecules coordinated to the Li$^+$ (FIG. 38). Both N1 and N3 are planar (sum of C—N—C angles=360°), indicating they are both sp$^2$ hybridized. The nitrogen carbene bond lengths of 27 (N1-C2=1.3671(17), N3-C2=1.3799(17) Å) are in the range reported for standard NHC Li adducts,[25] and comparable to compound 8 (FIG. 2).

The carborane-N bond length (N3-C1=1.4597(16) Å) and carbon boron distances in the cluster (average C-B distance 1.7724(19) Å) are close to that reported for 8, and suggest no exo-π-conjugation[26] between the carborane substituent and the carbene ring. The carbene/lithium bond length of 27 (C2-Li1=2.214(3) Å) is in the range reported for standard NHC lithium complexes.[25]

Forming an abnormal NHC by reaction of 23 with LDA was also investigated. Attempts to selectively deprotonate the backbone of imidazolium 23 with LDA led to intractable mixtures of 27 and multiple unidentified compounds (FIG. 37). Subsequently, double deprotonation reactions with n-BuLi were studied. Treatment of a solution of 23 dissolved in ether with 2 equivalents of n-BuLi results in the formation of a precipitate (FIG. 37). After stirring the mixture for two hours the precipitate was collected and analysed by NMR spectroscopy, which revealed clean formation of a single isomer of the doubly deprotonated dianionic species 31. In contrast to monoanionic 27, dianionic 31 is very soluble in THF. The $^1H$ NMR spectrum displayed a single resonance for the imidazolium ring at 6.6 ppm, which was assigned to the C-4 proton adjacent to the carborane anion through NOESY NMR analysis. This data indicates that lithiation of the imidazolium backbone occurs solely at the C-5 position of the ring. Without being bound by any particular theory, this directing effect is believed to result from a combination of steric and electrostatic effects induced by the carborane anion substituent. The $^{13}C$ NMR of 31 showed an unsymmetrical imidazolium ring with two low field quaternary resonances at 193.0 and 166.8 ppm that correspond to the C-2 and C-5 deprotonated carbon centers, respectively. The $^7Li$ NMR spectrum of 31 displays two resonances (3.5, 2.3 ppm), which suggests that both the C-2 and C-5 carbons are coordinated to Li$^+$ ions.

A single crystal X-ray diffraction study confirms the identity of 31 (FIG. 39). In contrast to the related trianionic N,N-dicarboranyl species 10 shown in FIG. 2, which is a Li$^+$-bridged dimer in the solid-state, 31 is monomeric. The central heterocyclic ring bond lengths of 31 (N1-C2=1.363 (2), N3-C2=1.364(2), N1-C5=1.426(2), N3-C4=1.407(2), C4-C5=1.369(3), Å) are similar to those reported for the trianionic species 10, as well as monoanionic hydrocarbon derivatives reported by Robinson.[27] The carborane nitrogen bond length of (N3-C1=1.446(2) Å) and carbon boron distances in the cluster (average C-B distances for carboranes 1.716(1) Å), are only slightly different compared to the normal C-2 dianionic carbene lithium adduct 27. A single close B—H contact with the lithium cation bound to C2 (H1-Li1=2.14 Å) suggests the occurrence of an agostic-like[28] interaction. The C2-Li1 bond length of 2.079(4) Å is shorter than the C5-Li2 distance (2.133(4) Å), which is perhaps a result of the B—H—Li bonding interaction that draws the C-2 carbene center closer to the alkali metal cation.

The present invention provides convenient methods for the synthesis of zwitterionic imidazolium species 23 and related compounds having N-hydrocarbon and N-carboranyl groups. Deprotonation of this zwitterion with alkali hexamethyl disilazide bases cleanly affords the normal C-2 NHC complexes 27 or 28. Attempted deprotonation of the zwitterion 23 with LDA to selectively form an abnormal NHC, leads to an intractable mixture. This result indicates that two anionic N-carboranyl groups promote selective imidazolium backbone deprotonation. Double deprotonation reactions of 23 with n-BuLi result in the selective formation of C-2/C-5 lithiated species 31, revealing an unprecedented directing effect of the anionic icosahedral carborane substituent.

V. Catalytic Reactions

The NHCs and related compounds described herein can be employed as ligands for catalysts or as catalysts in their own right. The instant application sets forth methods of catalyzing chemical reactions, wherein the methods include contacting a complex, set forth herein, with suitable reagents for the chemical reaction to occur. In some embodiments, the chemical reaction catalyzed is the insertion of reactive metal carbenes or nitrenes into C—H bonds. In some embodiments, the chemical reaction catalyzed is the dehydrogenation of an alkane to form olefins. In some embodiments, the chemical reaction catalyzed is olefin polymerization. In some embodiments, the chemical reaction catalyzed is hydroaddition. In some embodiments, the chemical reaction catalyzed is hydroamination. In some embodiments, the chemical reaction catalyzed is cross coupling. In some embodiments, the chemical reaction catalyzed is hydrogenation. In some embodiments, the chemical reaction catalyzed is hydroformylation. In some embodiments, the chemical reaction catalyzed is olefin metathesis.

Transition metal complexes are particularly useful as catalysts in a variety of synthetic organic reactions. In particular, the catalysts or complexes comprise a transition metal and a carbene ligand selected from the carborane-NHC's provided above. One of skill in the art will appreciate that such complexes can employ a number of transition metals and have a variety of geometries (e.g., linear, trigonal, square planar, trigonal bipyramidal and the like) depending on the nature of the transition metal and its oxidation state and other factors including, for example, additional ligands.

In general, any transition metal (e.g., a metal having d electrons) can be used to form the complexes/catalysts of the present invention. For example, suitable transition metals are those selected from one of Groups 3-12 of the periodic table or from the lanthanide series. Preferably, the metal will be selected from Groups 5-12 and even more preferably Groups 7-11. For example, suitable metals include platinum, palladium, iron, nickel, cobalt, iridium, ruthenium and rhodium. The particular form of the metal to be used in the reaction is selected to provide, under the reaction conditions, metal centers which are coordinately unsaturated and not in their highest oxidation state.

To further illustrate, suitable transition metal complexes and catalysts include soluble or insoluble complexes of platinum, palladium, iridium, iron, rhodium, ruthenium and nickel. Palladium, rhodium, iridium, ruthenium and nickel are particularly preferred and palladium is most preferred.

As noted above, the complexes further comprise a carborane-NHC ligand as described herein. The catalyst complex can include additional ligands as required to obtain a stable complex. The additional ligands can be neutral ligands, anionic ligands and/or electron-donating ligands. The ligand can be added to the reaction mixture in the form of a metal complex, or added as a separate reagent relative to the addition of the metal.

Anionic ligands suitable as additional ligands are preferably halide, pseudohalide, tetraphenylborate, perhalogenated tetraphenylborate, tetrahaloborate, hexahalophosphate, hexahaloantimonate, trihalomethanesulfonate, alkoxide, carboxylate, tetrahaloaluminate, tetracarbonylcobaltate, hexahaloferrate(III), tetrahaloferrate(III) or/and tetrahalopalladate(II). Preferably, an anionic ligand is selected from halide, pseudohalide, tetraphenylborate, perfluorinated tetraphenylborate, tetrafluoroborate, hexafluorophosphate, hexafluoroantimonate, trifluoromethanesulfonate, alkoxide, carboxylate, tetrachloroaluminate, tetracarbonylcobaltate, hexafluoroferrate (III), tetrachloroferrate(III) or/and tetrachloropalladate(II). Preferred pseudohalides are cyanide, thiocyanate, cyanate, isocyanate and isothiocyanate. Neutral or electron-donor ligands suitable as additional ligands can be, for example, amines, imines, phosphines, phosphites, carbonyl compounds, alkenyl compounds (e.g., allyl compounds, cyclooctadiene), carboxyl compounds, nitriles, alcohols, ethers, thiols or thioethers.

While the present invention describes a variety of transition metal complexes useful in catalyzing organic reactions, one of skill in the art will appreciate that many of the complexes can be formed in situ. Accordingly, ligands (either carborane-NHC ligands or additional ligands) can be added to a reaction solution as a separate compound, or can be complexed to the metal center to form a metal-ligand complex prior to its introduction into the reaction solution. The additional ligands are typically compounds added to the reaction solution which can bind to the catalytic metal center. In some preferred embodiments, the additional ligand is a chelating ligand. While the additional ligands can provide stability to the catalytic transition metal complex, they may also suppress unwanted side reactions as well as enhance the rate and efficiency of the desired processes. Still further, in some embodiments, the additional ligands can prevent precipitation of the catalytic transition metal. Although the present invention does not require the formation of a metal-additional ligand complex, such complexes have been shown to be consistent with the postulate that they are intermediates in these reactions and it has been observed the selection of the additional ligand has an effect on the course of the reaction.

As noted above, the complexes of the present invention are useful in catalyzing a variety of synthetic organic reactions including amine arylation reactions, Suzuki coupling reactions (aryl-aryl or aryl-alkyl coupling reactions), and α-arylation reactions. Still other reactions that can benefit from the above-noted complexes include, for example, hydroformylation (of alkenes and alkynes), hydrosilylation (of alkenes, alkynes, ketones and aldehydes), metathesis (olefin(RC, CM, ROM, ROMp) ene-yne), carbonylation, carbene/nitrene C—H insertion, alkane dehydrogenation, hydroarylation, and hydroamination.

The reactions of the present invention can be performed under a wide range of conditions, and the solvents and temperature ranges recited herein should not be considered limiting. In general, it is desirable for the reactions to be run using mild conditions which will not adversely affect the reactants, the catalyst, or the product. For example, the reaction temperature influences the speed of the reaction, as well as the stability of the reactants and catalyst. The reactions will typically be run at temperatures in the range of 25° C. to 300° C., more preferably in the range 25° C. to 150° C.

Additionally, the reactions are generally carried out in a liquid reaction medium, but in some instances can be run without addition of solvent. For those reactions conducted in solvent, an inert solvent is preferred, particularly one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aromatic hydrocarbon solvents such as benzene, xylene, toluene, and the like; esters and ketones such as ethyl acetate, acetone, and 2-butanone; polar aprotic solvents such as acetonitrile, dimethylsulfoxide, dimethylformamide and the like; or combinations of two or more solvents.

In some embodiments, reactions utilizing the catalytic complexes of the present invention can be run in a biphasic mixture of solvents, in an emulsion or suspension, or in a lipid vesicle or bilayer. In certain embodiments, the catalyzed reactions can be run in the solid phase with one of the reactants tethered or anchored to a solid support.

In certain embodiments, the reactions are performed under an inert atmosphere of a gas such as nitrogen or argon.

The reaction processes of the present invention can be conducted in continuous, semi-continuous or batch fashion and may involve a liquid recycle operation as desired. The processes of this invention are preferably conducted in batch fashion. Likewise, the manner or order of addition of the reaction ingredients, catalyst and solvent are also not generally critical to the success of the reaction, and may be accomplished in any conventional fashion.

In some embodiments, the instant application provides methods of catalyzing olefin polymerization reactions comprising contacting a complex described herein with suitable olefin polymerization reagents.

In some embodiments, the instant application provides methods of catalyzing hydroaddition reactions comprising contacting a complex described herein with suitable hydroaddition reagents.

In some embodiments, the instant application provides methods of catalyzing hydroamination reactions comprising contacting a complex described herein with suitable hydroamination reagents.

In some embodiments, the instant application provides methods of catalyzing cross coupling reactions contacting a complex described herein with suitable cross coupling reagents.

In some embodiments, the instant application provides methods of catalyzing olefin metathesis reactions comprising contacting a complex described herein with suitable olefin metathesis reagents.

In some embodiments, the instant application provides methods of catalyzing hydroformylation reactions comprising contacting a complex described herein with suitable hydroformylation reagents.

In some embodiments, the instant application provides methods of catalyzing hydrogenation reactions comprising contacting a complex described herein with suitable hydrogenation reagents.

In some embodiments, the instant application provides methods of catalyzing hydroaminomethylation reactions comprising contacting a complex described herein with suitable hydroaminomethylation reagents.

In some embodiments, the chemical reaction catalyzed is the insertion of reactive metal carbenes or nitrenes into C—H bonds.

In some embodiments, the chemical reaction catalyzed is the dehydrogenation of an alkane to form olefins.

VI. Applications

The compounds and compositions described herein may be suitable for use as components in a battery. For example, and without limitation, the compositions set forth herein may be suitable for use as a charge carrier. Also, for example, the compositions set forth herein may be suitable for use as a battery electrolyte.

Accordingly, certain embodiments of the invention provide batteries comprising one or more carborane compounds described herein. In some embodiments, the invention provides a battery component comprising a compound described herein. In some embodiments, the component is selected from a soluble electrolyte, an immobilized electrolyte, a polymer supported anion/zwitterion, a cathode or anode immobilized anion/zwitterion.

In some embodiments, the invention provides an alkali or alkali earth metal battery that contains a carborane compound of claims as described herein. In some embodiments, the metal is selected from Li, Na, K, Al, Rb, Be, Mg, Ca, Sr, and Ba.

In some embodiments, compositions described herein contain Mg counterions and are suitable electrolytes for Mg-based batteries. In some embodiments, compositions described herein that contain combinations of Li and Mg counterions are suitable electrolytes for Mg-based batteries. Such electrolytes typically display reversible electrochemical deposition and stripping of Mg with a low overpotential (0.001-0.075 V, vs $Mg^{0/+2}$). Typically, such electrolytes are anodically stable from 1-5 V vs $Mg^{0/+2}$. Such electrolytes generally have solubility (0.1-5 M) in ethereal solvents (THF, DME, other glymes).

The following references are cited above:

[1] a) M. Melaimi, M. Soleilhavoup, G. Bertrand, Angew. Chem. 2010, 122, 8992-9032; Angew. Chem. Int. Ed. 2010, 49, 8810-8849; b) S. Diez-Gonzalez, N. Marion, S. P. Nolan, Chem. Rev. 2009, 109, 3612-3676; c) P. L. Arnold, I. J. Casely, Chem. Rev. 2009, 109, 3599-3611; d) J. Vignolle, X. Cattoën, D. Bourissou, Chem. Rev. 2009, 109, 3333-3384; e) J. C. Y. Lin, R. T. W. Huang, C. S. Lee, A. Bhattacharyya, W. S. Hwang, I. J. B. Lin, Chem. Rev. 2009, 109, 3561-3598; f) F. E. Hahn, M. C. Jahnke, Angew. Chem. 2008, 120, 3166-3216; Angew. Chem. Int. Ed. 2008, 47, 3122-3172. For the first examples of stable carbenes, see: g) A. Igau, H. Grutzmacher, A. Baceiredo, G. Bertrand, J. Am. Chem. Soc. 1988, 110, 6463-6466. h) A. J. Arduengo, R. L. Harlow, M. Kline, J. Am. Chem. Soc. 1991, 113, 361-363.

[2] For recent reviews discussing NHCs as ligands for catalysis, see: a) L.-A. Schaper, S. J. Hock, W. A. Herrmann, F. E. Kühn, Angew. Chem. 2013, 125, 284-304; Angew. Chem. Int. Ed. 2013, 52, 270-289; b) T. Dröge, F. Glorius, Angew. Chem. 2010, 122, 7094-7107; Angew. Chem. Int. Ed. 2010, 49, 6940-6952; c) C. Samojlowicz, M. Bieniek, K. Grela, Chem. Rev. 2009, 109, 3708-3742.

[3] For reviews discussing the use of NHCs to stabilize reactive species, see: a) C. D. Martin, M. Soleilhavoup, G. Bertrand, Chem. Sci. 2013, 4, 3020-3030; b) Y. Wang, G. H. Robinson, Dalton Trans. 2012, 41, 337-345; For recent examples of the use of NHCs to stabilize reactive species, see: c) Y. Xiong, S. Yao, S. Inoue, J. D. Epping, M. Driess, Angew. Chem. 2013, 125, 7287-7291; Angew. Chem. Int. Ed. 2013, 52, 7147-7150; d) K. C. Mondal, H. W. Roesky, A. C. Stuckl, F. Ehret, W. Kaim, B. Dittrich, B. Maity, D. Koley, Angew. Chem. 2013, 125, 12020-12023; Angew. Chem. Int. Ed. 2013, 52, 11804-11807.

[4] For recent reviews discussing the use of NHCs as organocatalysts, see: a) A. Grossmann, D. Enders, Angew. Chem. 2012, 124, 320-332; Angew. Chem. Int. Ed. 2012, 51, 314-325; b) S. E. Denmark, G. L. Beutner, Angew. Chem. 2008, 120, 1584-1663; Angew. Chem. Int. Ed. 2008, 47, 1560-1638; c) N. Marion, S. Díez-González, S. P. Nolan, Angew. Chem. 2007, 119, 3046-3058; Angew. Chem. Int. Ed. 2007, 46, 2988-3000.

[5] S. Grundemann, A. Kovacevic, M. Albrecht, J. W. Faller, R. H. Crabtree, Chem. Commun. 2001, 2274-2275.

[6] For reviews discussing abnormal NHCs, see: a) R. H. Crabtree, Coord. Chem. Rev. 2013, 257, 755-766; b) A.

Kruger, M. Albrecht, RSC Catal. Ser. 2011, 6, 134-165; c) O. Schuster, L. R. Yang, H. G. Raubenheimer, M. Albrecht, Chem. Rev. 2009, 109, 3445-3478; d) A. Krüger, M. Albrecht, Aust. J. Chem. 2011, 64, 1113-1117; e) P. L. Arnold, S. Pearson, Coord. Chem. Rev. 2007, 251, 596-609; For select examples of the unusual properties of abnormal NHCs, see; f) L. Yang, A. Krüger, A. Neels, M. Albrecht, Organometallics 2008, 27, 3161-3171; g) M. Heckenroth, E. Kluser, A. Neels, M. Albrecht, Angew. Chem. 2007, 119, 6409-6412; Angew. Chem. Int. Ed. 2007, 46, 6293-6296.

[7] a) E. Aldeco-Perez, A. J. Rosenthal, B. Donnadieu, P. Parameswaran, G. Frenking, G. Bertrand, Science 2009, 326, 556-559; b) M. Albrecht, Science 2009, 326, 532-533.

[8] a) Y. Wang, Y. Xie, M. Y. Abraham, P. Wei, H. F. Schaefer, P. v. R. Schleyer, G. H. Robinson, J. Am. Chem. Soc. 2010, 132, 14370-14372; For an elegent strategy to form C-2/C-5 bound dimetallic species and C-5 abnormal carbene complexes containing an H at C-2, see: b) A. Kruger, E. Kluser, H. Müller-Bunz, A. Neels, M. Albrecht, Eur. J. Inorg. Chem. 2012, 1394-1402; For a related example of a dicarbene based on a the 1,2,4-triazole framework that can form heterodimetallic transitionmetal complexes, see: c) E. Mas-Marza, Jose A. Mata, E. Penis Angew. Chem. 2007, 119, 3803-3805; Angew. Chem. Int. Ed. 2007, 46, 3729-3731.

[9] For recent reviews discussing icosahedral carboranes and related molecules, see: a) C. Douvris, J. Michl, Chem. Rev. 2013, 113, PR179-PR233; b) A. M. Spokoyny, Pure Appl. Chem. 2013, 85, 903-919; c) D. Brusselle, P. Bauduin, L. Girard, A. Zaulet, C. Viñas, F. Teixidor, I. Ly, O. Diat, Angew. Chem. 2013, 125, 12336-12340; Angew. Chem. Int. Ed. 2013, 52, 12114-12118; d) D. Olid, R. Nuñez, C. Viñas, F. Teixidor, Chem. Soc. Rev. 2013, 42, 3318-3336; e) P. Farras, E. J. Juarez-Perez, M. Lepsik, R. Luque, R. Nuñez, F. Teixidor, Chem. Soc. Rev. 2012, 41, 3445-3463; f) M. Scholz, E. Hey-Hawkins, Chem. Rev. 2011, 111, 7035-7062.

[10] W. H. Knoth, J. Am. Chem. Soc. 1967, 89, 1274-1275.

[11] For a recent review discussing the use of the carba-closo-dodecaborate anion to stabilize reactive species, see: a) C. A. Reed, Acc. Chem. Res. 2009, 43, 121-128; For recent examples, see: b) R. T. Boeré, C. Bolli, M. Finze, A. Himmelspach, C. Knapp, T. L. Roemmele, Chem. Eur. J. 2013, 19, 1784-1795; c) C. Bolli, T. Köchner, C. Knapp, Z. Anorg. Allg. Chem. 2012, 638, 559-564; d) R. Ramirez-Contreras, N. Bhuvanesh, J. Zhou, O. V. Ozerov, Angew. Chem. 2013, 125, 10503-10505; Angew. Chem. Int. Ed. 2013, 52, 10313-10315; e) A. Himmelspach, M. Finze, S. Raub, Angew. Chem. 2011, 123, 2676-2679; Angew. Chem. Int. Ed. 2011, 50, 2628-2631; f) C. Douvris, C. M. Nagaraja, C.-H. Chen, B. M. Foxman, O. V. Ozerov, J. Am. Chem. Soc. 2010, 132, 4946-4953; g) C. Douvris, O. V. Ozerov, Science 2008, 321, 1188-1190.

[12] a) V. Lavallo, J. H. Wright, F. S. Tham, S. Quinlivan, Angew. Chem. 2013, 125, 3254-3258; Angew. Chem. Int. Ed. 2013, 52, 3172-3176; b) A. El-Hellani, C. E. Kefalidis, F. S. Tham, L. Maron, V. Lavallo, Organometallics 2013, 32, 6887-6890.

[13] Tamm and coworkers have recently described the elegant synthesis and applications of a family of anionic NHCs, bearing weakly coordinating borate groups covalently linked to the normal NHC C-C backbone a) E. L. Kolychev, S. Kronig, K. Brandhorst, M. Freytag, P. G. Jones, M. Tamm, J. Am. Chem. Soc. 2013, 135, 12448-12459; b) S. Kronig, E. Theuergarten, C. G. Daniliuc, P. G. Jones, M. Tamm, Angew. Chem. 2012, 124, 3294-3298; Angew. Chem. Int. Ed. 2012, 51, 3240-3244.

[14] T. Jelinek, J. Plešek, S. Heřmánek, B. Štíbr, Collect. Czech. Chem. Commun. 1986, 51, 819-829.

[15] For recent discussions of cluster exo-π-bonding, see: a) J. H. Wright, C. E. Kefalidis, F. S. Tham, L. Maron, V. Lavallo, Inorg. Chem. 2013, 52, 6223-6229; b) M. Asay, C. E. Kefalidis, J. Estrada, D. S. Weinberger, J. Wright, C. E. Moore, A. L. Rheingold, L. Maron, V. Lavallo, Angew. Chem. 2013, 125, 11774-11777; Angew. Chem. Int. Ed. 2013, 52, 11560-11563; c) L. A. Boyd, W. Clegg, R. C. B. Copley, M. G. Davidson, M. A. Fox, T. G. Hibbert, J. A. K. Howard, A. Mackinnon, R. J. Peace, K. Wade, Dalton Trans. 2004, 2786-2799.

[16] a) A. S. Weller, M. F. Mahon, J. W. Steed, J. Organomet. Chem. 2000, 614-615, 113-119; b) C. Viñas, R. Nuñez, F. Teixidor, R. Kivekäs, R. Sillanpää, Organometallics 1996, 15, 3850-3858; c) F. Teixidor, J. A. Ayllon, C. Viñas, R. Kivekäs, R. Sillanpää, J. Casabo, Organometallics 1994, 13, 2751-2760; d) F. Teixidor, J. A. Ayllon, C. Viñas, R. Kivekäs, R. Sillanpää, J. Casabo, J. Chem. Soc., Chem. Commun. 1992, 1281-1282.

[17] For an example of the isomerization of transient C-5 abnormal to stable C-2 NHCs, via the migration of main group substituents, see: a) D. Mendoza-Espinosa, B. Donnadieu, G. Bertrand, J. Am. Chem. Soc. 2010, 132, 7264-7265; For an example of C-2 to C-5 NHC isomerization at a transition metal center, see: B. M. Day, T. Pugh, D. Hendriks, C. F. Guerra, D. J. Evans, F. M. Bickelhaupt, R. A. Layfield, J. Am. Chem. Soc. 2013, 135, 13338-13341.

[18] a) D. Brusselle, P. Bauduin, L. Girard, A. Zaulet, C. Viñas, F. Teixidor, I. Ly, O. Diat, Angew. Chem. 2013, 125, 12336-12340; Angew. Chem. Int. Ed. 2013, 52, 12114-12118; b) J. G. Planas, C. Viñas, F. Teixidor, A. Comas-Vives, G. Ujaque, A. Lledos, M. E Light, M. B. Hursthouse, J. Am. Chem Soc. 2005, 127, 15976-15982.

[19] The dimeric structure of 10 is similar to some aryllithium species. For a review on the structure of lithium stabilized carbanions, see: R. A. Gossage, J. T. B. H. Jastrzebski, G. van Koten, Angew. Chem. 2005, 117, 1472-1478; Angew. Chem. Int. Ed. 2005, 44, 1448-1454.

[20] R. Van Noorden, Nature 2014, 507, 26.

[21] a) R. Mohtadi, F. Mizuno, Beilstein J. Nanotechnol. 2014, 5, 1291; b) H. D. Yoo, I. Shterenberg, Y. Gofer, G. Gershinsky, N. Pour, D. Aurbach, Energy Environ. Sci. 2013, 6, 2265; c) J. Muldoon, C. B. Bucur, A. G. Oliver, T. Sugimoto, M. Matsui, H. S. Kim, G. D. Allred, J. Zajicek, Y. Kotani, Energy Environ. Sci. 2012, 5, 5941-5950.

[22] C. Douvris, J. Michl, Chem. Rev. 2013, 113, PR179.

[23] T. J. Carter, R. Mohtadi, T. S. Arthur, F. Mizuno, R. Zhang, S. Shirai, J. W. Kampf, Angew. Chem. Int. Ed. 2014, 53, 3173.

The literature describing Au-based catalysts includes a) H. Schmidbaur, et al., B: J. Chem. Sci. 2011, 66, 329-350; Synthesis (Eds.: A. S. K. Hashmi, F. D. Toste), Wiley-VCH, Weinheim, 2012; A. Gómez-Suárez, et al., Angew. Chem. 2012, 124, 8278-8281; Angew. Chem. Int. Ed. 2012, 51, 8156-8159; C. C. J. Loh, et al., Chem. Eur. J. 2012, 18, 10212-10225; D. Garayalde, et al., ACS Catal. 2012, 2, 1462-1479; D. Wang, et al., J. Am. Chem. Soc. 2012, 134, 9012-9019; f) B.-L. Lu, L. Dai, M. Shi, Chem. Soc. Rev. 2012, 41, 3318-3339; L.-P. Liu, et al., Chem. Soc. Rev. 2012, 41, 3129-3139; M. Rudolph, et al., Chem. Soc. Rev. 2012, 41, 2448-2462; C. D. Pina et al., Chem. Soc. Rev. 2012, 41, 350-369; M. Rudolph, et al., Chem. Commun. 2011, 47, 6536-6544; M. Bandini, Chem. Soc. Rev. 2011, 40, 1358-1367; M. Malacria, Top. Curr. Chem. 2011, 302, 157-182; A. S. K. Hashmi, Angew. Chem. 2010, 122, 5360-5369; Angew. Chem. Int. Ed. 2010, 49, 5232-5241; D. J. Gorin, et al., Chem. Rev. 2008, 108, 3351-3378.

The literature describing hydroamination reactions includes J. L. Klinkenberg, et al., Angew. Chem. 2011, 123, 88-98; Angew. Chem. Int. Ed. 2011, 50, 86-95; I. Krossing, Angew. Chem. 2011, 123, 11781-11783; Angew. Chem. Int. Ed. 2011, 50, 11576-11578; T. E. Müller, et al., Chem. Rev. 2008, 108, 3795-3892; R. A. Widenhoefer, et al., Eur. J. Org. Chem. 2006, 2006, 4555-4563.

The literature describing gold catalyzed hydroamination of alkynes includes S. Fleischer, et al., Chem. Eur. J. 2012, 18, 9005-9010; E. Alvarado, et al., Chem. Eur. J. 2012, 18, 12112-12121; R. Kinjo, et al., Angew. Chem. 2011, 123, 5674-5677; Angew. Chem. Int. Ed. 2011, 50, 5560-5563; K. L. Butler, et al., Angew. Chem. 2012, 124, 5265-5268; Angew. Chem. Int. Ed. 2012, 51, 5175-5178; K. D. Hesp, et al., J. Am. Chem. Soc. 2010, 132, 18026-18029; A. Leyva-Perez, et al., J. Org. Chem. 2010, 75, 7769-7780; V. Lavallo, et al., Angew. Chem. 2008, 120, 5302-5306; Angew. Chem. Int. Ed. 2008, 47, 5224-5228; E. Mizushima, et al., Org. Lett. 2003, 5, 3349-3352).

[24] E. Aldeco-Perez, A. J. Rosenthal, B. Donnadieu, P. Parameswaran, G. Frenking and G. Bertrand, Science, 2009, 326, 556.

[25] S. Bellemin-Laponnaz and S. Dagorne, Chem. Rev., 2014, 114, 8747.

[26] L. A. Boyd, W. Clegg, R. C. B. Copley, M. G. Davidson, M. A. Fox, T. G. Hibbert, J. A. K. Howard, A. Mackinnon, R. J. Peace and K. Wade, Daltons Trans. 2004, 2786.

[27] Y. Wang, Y. Xie, M. Y. Abraham, P. Wei, H. F. Schaefer, P. v. R. Schleyer and G. H. Robinson, J. Am. Chem. Soc., 2010, 132, 14370.

[28] (a) M. Etienne and A. S. Weller, Chem. Soc. Rev., 2014, 43, 242; (b) M. Brookhart, M. L. H. Green and G. Parkin, Proc. Natl. Acad. Sci. U.S.A., 2007, 104, 6908.

VII. EXAMPLES

The following examples are offered to illustrate, but not to limit the claimed invention.

General Considerations

Unless otherwise stated, all manipulations were carried out using standard Schlenk or glovebox techniques ($O_2$, $H_2O$<1 ppm) under a dinitrogen or argon atmosphere. Solvents were dried on K or $CaH_2$, and distilled under argon before use. $CsNH_2CB_{11}H_{11}$ 5 was prepared by literature methods (1). Reagents were purchased from commercial vendors and used without further purification. NMR spectra were recorded on Bruker Avance 300 MHz, Bruker Avance 600 MHz, Varian Inova 300 MHz, or Varian Inova 400 MHz spectrometers. NMR chemical shifts are reported in parts per million (ppm). $^1$H NMR and $^{13}$C NMR chemical shifts were referenced to residual solvent. $^{11}$B NMR chemical shifts were externally referenced to $BF_3OEt_2$. $^{31}$P NMR chemical shifts were externally referenced to 80% $H_3PO_4$ in $H_2O$. $^7$Li NMR chemical shifts were externally referenced to a 0.1 M solution of LiCl in THF. HRMS was recorded on Agilent Technologies 6210 (time of flight LC/MS) using ESI technique. Complete crystallographic data for compounds 7(Cs+), 8 and 10 are available free of charge from the Cambridge Crystallographic Data Center under reference numbers 973664, 973666 and 973665, respectively.

Example 1. Synthesis of Carborane Imidazolium Compounds

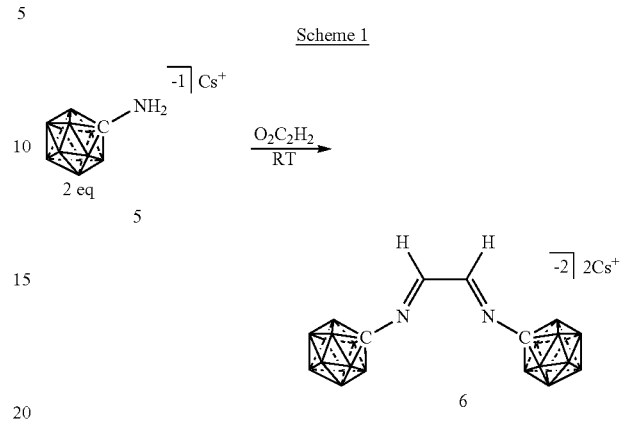

Scheme 1

Synthesis of Diimine 6(Cs+).

To a solution of $CsNH_2CB_{11}H_{11}$ 5 (1.115 g, 3.83 mmol) in methanol (20 mL) was added glyoxal ($O_2C_2H_2$) aqueous solution (40% w/w, 290 mg, 1.9 mmol) and the reaction mixture stirred for 3 hours. Volatiles were removed under reduced pressure to afford the diimine 6(Cs$^+$) as a light brown powder in 98% yield (1.135 g, 1.88 mmol). 6(Cs$^+$) was used for subsequent steps without further purification. To obtain a more pure product (see FIG. S2), 6(Cs$^+$) can be converted to its $HNMe_3^+$ salt 6($HNMe_3^+$) by dissolving it in $H_2O$ (100 mL) followed by the addition of 2 eq. (3.83 mmol, 336.0 mg) of $HNMe_3Cl$. The precipitate of 6($HNMe_3^+$) was collected by filtration and dried under high vacuum to afford the product in 97% yield (796.0 mg, 1.85 mmol). Spectroscopic data for 6(Cs$^+$); $^1$H NMR (300 MHz, acetone-$d_6$, 25° C.): δ=7.73 (s, 2H), 3.50-0.50 (bm, 22H, B—H); $^{13}$C-($^1$H-dec) NMR (125 MHz, acetone-$d_6$, 25° C.): δ=162.3; $^{11}$B-($^1$H-dec) NMR (96 MHz, acetone-$d_6$, 25° C.): δ=−11.2, −15.0 ppm. HRMS (negative mode ESI/APCI) [M+H]$^-$ m/z calc'd for $N_2C_4B_{22}H_{25}^-$: 339.4215. found 339.4203.

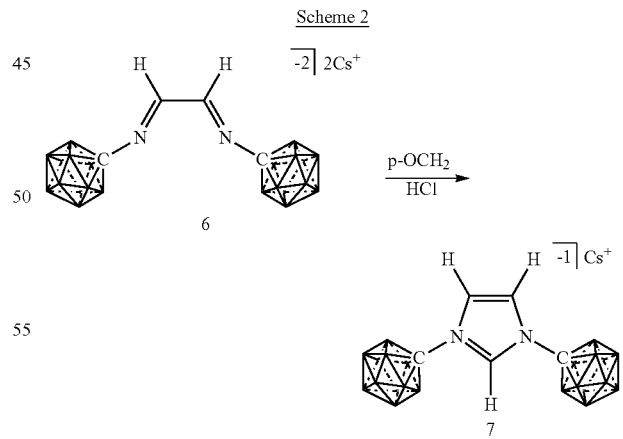

Scheme 2

Synthesis of Imidazolium Salt 7(Cs$^+$).

A solution of HCl/dioxane (4.0 M, 0.75 mL) was added to paraformaldehyde (68.0 mg, 2.2 mmol) and stirred for 20 min., then the mixture was added to an EtOAc (0.5 M, 4 mL) solution of the diimine 6(Cs+) (1.15 g, 1.9 mmol) and the reaction mixture was stirred for 3 hours. Subsequent removal of all volatiles under high vacuum afforded 7(Cs$^+$)

as a crude mixture with CsCl, and the material was subsequently used to form the corresponding 7(HNMe$_3^+$) salt without further purification. At the expense of a lower yield, pure 7(Cs$^+$), lacking the CsCl byproduct, can be obtained by washing the residue with 100 mL of boiling water (74%, 869 mg, 1.41 mmol). Crystals suitable for a single crystal X-ray diffraction study were obtained by slow evaporation of a methanol solution of 7(Cs$^+$). m.p.=245-246° C. $^1$H NMR (500 MHz, acetone-d$_6$, 25° C.): δ=8.36 (t, $^4$J(H,H)=1.74 Hz, 1H), 7.41 (d, $^4$J(H,H)=1.74 Hz, 2H), 3.25-0.75 (bm, 22H, B—H). $^{13}$C-($^1$H-dec) NMR (125 MHz, acetone-d$_6$, 25° C.): δ=134.6, 123.7, 67.6; $^{11}$B-($^1$H-dec) NMR (96 MHz, acetone-d$_6$, 25° C.): δ=-8.7, -13.2, -14.1 ppm. HRMS (negative mode ESI/APCI) [M]$^-$ m/z calc'd for N$_2$C$_5$B$_{22}$H$_{25}^-$: 351.4215. Found=351.4226.

Synthesis of a Mixture of Li$^+$ NHC Complexes 8, 9, 10.

A vial with a stir bar was loaded with 435.0 mg (1.06 mmol) of imidazolium salt 7(HNMe$_3^+$) and 3.5 equivalents (397.4 mg, 3.71 mmol) of LDA. THF (10 mL) was subsequently added and the vial was capped and the mixture stirred for 24 hours. Removal of the volatiles under high vacuum and subsequent $^1$H NMR analysis revealed a mixture of normal C-2 8, abnormal C-5 9 and di C-2,C-5 10 Li$^+$ NHC complexes. $^1$H NMR (300 MHz, THF-d$_8$, 25° C.): δ=8.26 (d, $^4$J(H,H)=1.0 Hz, 1H, NHC 9), 6.91 (s, 2H, NHC 8), 6.30 (d, $^4$J(H,H)=1.0 Hz, 1H, NHC 9), 6.13 (s, 1H, NHC 10).

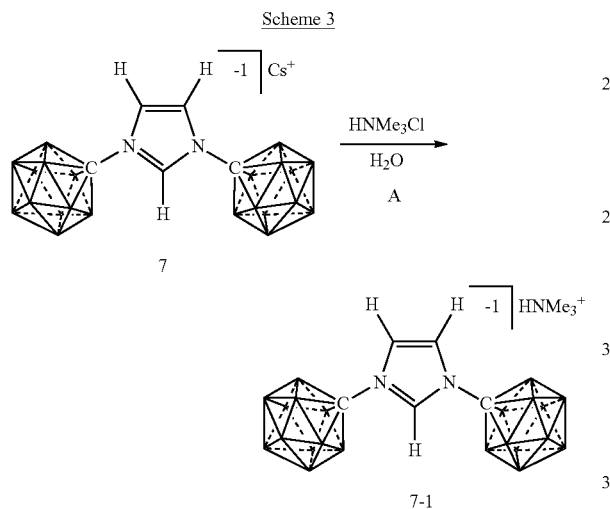

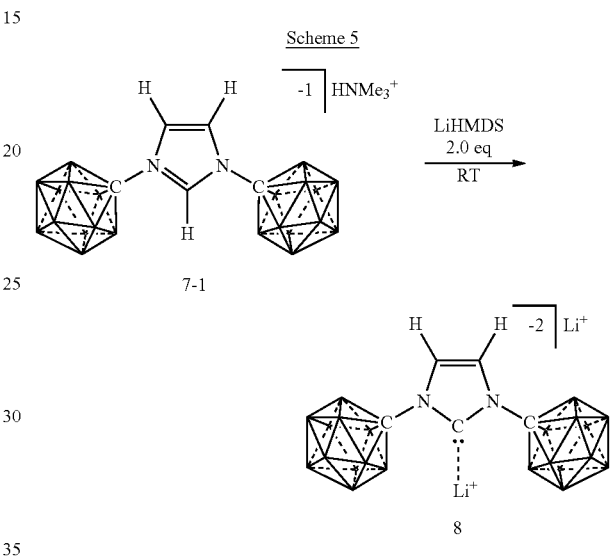

Synthesis of Imidazolium Salt 7-1.

The crude mixture of 7 and CsCl (described above) was dissolved in H$_2$O (100 mL) and HNMe$_3$Cl (173.0 mg, 2.0 mmol) was added, whereupon a precipitate instantly formed. The precipitate was collected by filtration and dried under high vacuum to afford 7-1 in 98% yield (764.1 mg, 1.86 mmol) overall starting from the diimine 6(Cs+). $^1$H NMR (300 MHz, acetone-d$_6$, 25° C.): δ=8.36 (t, $^4$J(H,H)=1.74 Hz, 1H), 7.41 (d, $^4$J(H,H)=1.74 Hz, 2H), 2.84 (d, $^3$J(H,H))=8.5 Hz, 9H, Me$_{HNMe3+}$), 3.25–0.75 (bm, 22H, B—H). HRMS (negative mode ESI/APCI) [M]$^-$ m/z calc'd for N$_2$C$_5$B$_{22}$H$_{25}^-$: 351.4215. Found=351.4223.

Example 2. Synthesis of Carborane NHC Complexes

Synthesis of Normal Li$^+$ NHC 8.

A vial with a stir bar was loaded with 435.0 mg (1.06 mmol) of imidazolium salt 7-1 and 2.0 equivalents (354.7 mg, 2.12 mmol) of LiHMDS. THF (10 mL) was subsequently added and the vial was capped and the mixture stirred for 1 hour. Removal of the volatiles under high vacuum and subsequent washing of the residue with benzene (3×5 mL) afforded 8 in 96% yield (811.7 mg, 1.02 mmol) (Note: Li$^+$ countercations contain 6 coordinated THF molecules). Crystals suitable for a single crystal X-ray diffraction study were grown at 23° C. by layering a F—C$_6$H$_5$ solution of 8 with hexane. m.p.=280-281° C., dec. $^1$H NMR (500 MHz, THF-d$_8$, 25° C.): δ=6.91 (s, 2H), 2.50-0.75 (bm, 22H, B—H); $^{13}$C-($^1$H-dec) NMR (125 MHz, THF-d$_8$, 25° C.): δ=196.9, 120.8, 81.4; $^{11}$B-($^1$H-dec) NMR (96 MHz, THF-d$_8$, 25° C.): δ=-10.1, -14.2 ppm. $^7$Li NMR (233 MHz, THF, 25° C.): δ=-0.52 ppm.

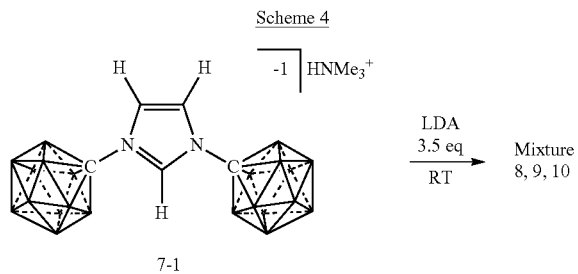

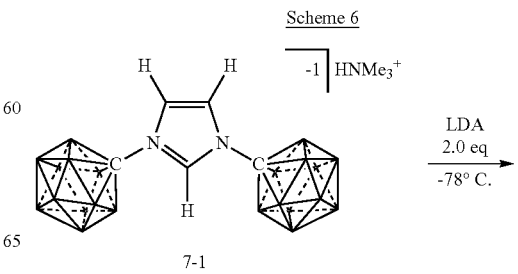

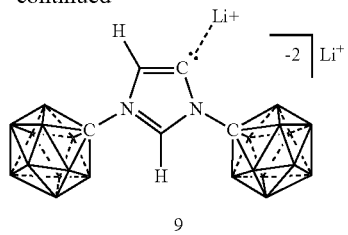

9

Synthesis of Abnormal Li+ NHC 9.

Two Schlenks containing stir bars were loaded with 435.0 mg (1.06 mmol) of imidazolium salt 7-1 and 227.1 mg (2.12 mmol) of LDA, respectively. To each Schlenk was added 10 mL of rigorously dried THF to dissolve the base and imidazolium salt and both solutions were cooled to −78° C. The solution of imidazolium salt 7-1 was quickly drawn up into a syringe and added dropwise to the vigorously stirred solution of LDA. No attempt was made to rinse the syringe or the Schlenk containing 7-1 in order to ensure a small excess of LDA to prevent any possibility of imidazolium catalyzed isomerization. The mixture was stirred for 2 hours, and the volatiles were subsequently removed by applying a vacuum immediately after removing the Schlenk from the −78° C. bath. The residue was washed at 0° C. with ether (3 mL) and dryed to afford 9 as an off-white solid in approximately 97% yield (893.0 mg, 1.03 mmol). The Li' countercations contain approx. 7 coordinated THF molecules as well as traces of coordinated ether, trimethylamine and diisopropylamine. The traces of coordinated amines can be removed by dissolving the product 9 in 3 mL of cold (−40° C.) THF and subsequently precipitating 9 by adding the solution to a vigorously stirred cold (−40° C.) flask containing 30 mL of ether. The coordinated amines and some of the THF molecules are displaced by the ether. $^1$H NMR (500 MHz, THF-$d_8$, 25° C.): δ=8.24 (d, $^4$J(H,H)=1.50 Hz, 1H), 6.29 (d, $^4$J(H,H)=1.50 Hz, 1H), 3.32 (Et$_2$O), 2.80-0.50 (bm, 22H, B—H), 2.79 (HN(C$_3$H$_7$)$_2$), 2.22 (Me$_3$N), 1.06 (Et$_2$O), 0.91 (HN(C$_3$H$_7$)$_2$); $^{13}$C-($^1$H-dec) NMR (125 MHz, THF-$d_8$, 25° C.): δ=174.7, 134.9, 126.2, 82.0, 76.4, 66.0 (Et$_2$O), 46.0 (Me$_3$N), 45.6 (HN(C$_3$H$_7$)$_2$), 23.6 (HN(C$_3$H$_7$)$_2$), 15.4 (Et$_2$O); $^{11}$B-($^1$H-dec) NMR (96 MHz, THF-$d_8$, 25° C.): δ=−11.1, −14.2 ppm. $^7$Li NMR (233 MHz, THF, 25° C.): δ=−0.51 ppm.

Scheme 7

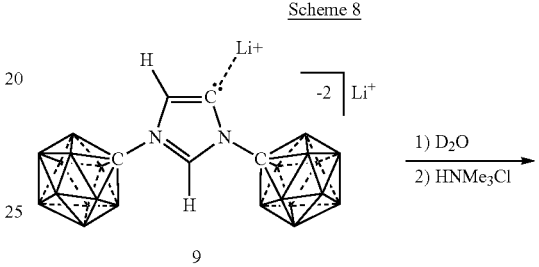

Isomerization of Abnormal Li+ NHC 9 to Normal Li+ NHC 8—

Procedure A (see, Scheme 7). A solution of 9 in THF was heated to 50° C. and monitored by $^1$H NMR (THF-$d_8$). Over a 24 hour period 9 completely isomerizes to 8 as judged by comparison with the $^1$H NMR spectra for isolated 9 and 8.

Isomerization of Abnormal Li+ NHC 9 to Normal Li+ NHC 8—

Procedure B (see, Scheme 7). At ambient temperature a solution of 9 (30 mg) in THF-$d_8$ was treated with 7(Cs+) (<1 mg) and immediately analyzed by $^1$H NMR spectroscopy to reveal complete isomerization of 9 to 8.

Scheme 8

Deuteration of 9 to form $7_D$(HNMe$_3$+).

To a Schlenk containing 9 (100 mg, 0.115 mmol) was added D$_2$O (20 mL) and the mixture was stirred vigorously for 10 minutes. Subsequent addition of HNMe$_3$Cl (43.0 mg, 0.5 mmol) to the mixture induced immediate precipitation of the C-5 deuterated product $7_D$(HNMe$_3$+), which was isolated by filtration and dried under high vacuum (85% yield, 0.098 mmol, 46.0 mg). $^1$H NMR (300 MHz, acetone-$d_6$, 25° C.): δ=8.52 (d, $^4$J(H,H)=1.73 Hz, 1H), 7.65 (d, $^4$J(H,H)=1.73 Hz, 1H), 3.01 (s, 9H), 3.25-0.75 (bm, 22H, B—H). HRMS (negative mode ESI/APCI) [M]$^-$ m/z calc'd for N$_2$C$_5$B$_{22}$H$_{24}$D$^-$: 352.4278. found 352.4284.

Scheme 9

-continued

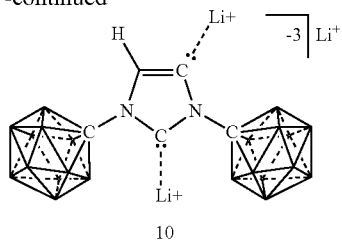

10

Synthesis of C-2,C-5-deprotonated Species 10.

n-BuLi (2.5 M, in hexane, 1.23 mL, 3.18 mmol) was added to a vial and placed under vacuum for 30 minutes to remove the hexane solvent. The n-BuLi was redissolved in diethyl ether (20 mL) and added to a separate vial containing 7-1 (435.0 mg, 1.06 mmol). The mixture was stirred vigorously and an oil formed over ten minutes. Continued stirring of the mixture for 4 hours resulted in the oil becoming a solid precipitate. The precipitate was collected by filtration and dried under high vaccum to afford 10 in 95% yield (596.0 mg, 1.00 mmol). (Note: the Li$^+$ countercations have three molecules of coordinated ether). $^1$H NMR (400 MHz, THF-d$_8$, 25° C.): δ=6.21 (s, 1H), 2.60-0.50 (bm, 22H, B—H); $^{13}$C-($^1$H-dec) NMR (125 MHz, THF-d$_8$, 25° C.): δ=195.6, 169.5, 126.8, 89.1, 83.0; $^{11}$B-($^1$H-dec) NMR (96 MHz, THF-d$_8$, 25° C.): δ=−10.7, −14.0 ppm. $^7$Li NMR (233 MHz, THF, 25° C.): δ=−0.18, −0.21 ppm.

Example 3. Solid State Structure of Carborane NHCs

Imidazolium Anion 7(Cs$^+$).

A colorless prism fragment (0.52×0.10×0.02 mm$^3$) was used for the single crystal x-ray diffraction study of C$_5$H$_{25}$B$_{22}$N$_2$Cs (sample vL85r_0m). The crystal was coated with paratone oil and mounted on to a cryo-loop glass fiber. X-ray intensity data were collected at 100(2) K on a Bruker APEX2 platform-CCD x-ray diffractometer system (fine focus Mo-radiation, λ=0.71073 Å, 50 KV/35 mA power). The CCD detector was placed at a distance of 5.0600 cm from the crystal.

A total of 3600 frames were collected for a sphere of reflections (with scan width of 0.3° in ω, starting ω and 2θ angles at −30°, and φ angles of 0°, 90°, 120°, 180°, 240°, and 270° for every 600 frames, 10 sec/frame exposure time). The frames were integrated using the Bruker SAINT software package and using a narrow-frame integration algorithm. Based on an monoclinic crystal system, the integrated frames yielded a total of 11553 reflections at a maximum 2θ angle of 60.06° (0.71 Å resolution), of which 3197 were independent reflections (R$_{int}$=0.0272, R$_{sig}$=0.0261, redundancy=3.6, completeness=100%) and 3191 (99.8%) reflections were greater than 2σ(I). The unit cell parameters were, a=12.6305(8) Å, b=7.1583(4) Å, c=12.1306(7) Å, β=91.091(1)°, V=1096.56(11) Å$^3$, Z=2, calculated density D$_c$=1.466 g/cm$^3$. Absorption corrections were applied (absorption coefficient μ=1.685 mm$^{-1}$; max/min transmission=0.9687/0.4739) to the raw intensity data using the SADABS program.

Normal Li$^+$ NHC Adduct 8.

A colorless prism fragment (0.41×0.30×0.17 mm$^3$) was used for the single crystal x-ray diffraction study of [CH$_{11}$B$_{11}$]$_2$C$_3$H$_2$N$_2$Li[C$_4$H$_8$O]$_2$·Li[C$_4$H$_8$O]$_4$ (sample vL96_190K_0m). The crystal was coated with paratone oil and mounted on to a cryo-loop glass fiber. X-ray intensity data were collected at 190(2) K on a Bruker APEX2 platform-CCD x-ray diffractometer system (fine focus Mo-radiation, λ=0.71073 Å, 50 KV/35 mA power). The CCD detector was placed at a distance of 5.0600 cm from the crystal.

A total of 3600 frames were collected for a sphere of reflections (with scan width of 0.3° in ω, starting ω and 2θ angles at −30°, and φ angles of 0°, 90°, 120°, 180°, 240°, and 270° for every 600 frames, 60 sec/frame exposure time). The frames were integrated using the Bruker SAINT software package and using a narrow-frame integration algorithm. Based on a monoclinic crystal system, the integrated frames yielded a total of 107401 reflections at a maximum 2θ angle of 59.14° (0.72 ⊢ resolution), of which 13501 were independent reflections (R$_{int}$=0.0366, R$_{sig}$=0.0215, redundancy=8.0, completeness=100%) and 9807 (72.6%) reflections were greater than 2σ(I). The unit cell parameters were, a=14.9789(7) Å, b=10.6400(5) Å, c=30.3932(15) Å, β=96.884(1°), V=4809.0(4) Å$^3$, Z=4, calculated density D$_c$=1.100 g/cm$^3$. Absorption corrections were applied (absorption coefficient μ=0.063 mm$^{-1}$; max/min transmission=0.9894/0.9744) to the raw intensity data using the SADABS program.

The Bruker SHELXTL software package was used for phase determination and structure refinement. The distribution of intensities (E$^2$-1=0.334) and systematic absent reflections indicated three possible space groups, C2, C2/m, and Cm. The space group C2 (#5) was later determined to be correct. Direct methods of phase determination followed by two Fourier cycles of refinement led to an electron density map from which most of the non-hydrogen atoms were identified in the asymmetric unit of the unit cell. With subsequent isotropic refinement, all of the non-hydrogen atoms were identified. There was half a polymeric molecule of C$_5$H$_{25}$B$_{22}$N$_2$Cs present in the asymmetric unit of the unit cell. The Cs1, C3 and H3 atoms are located on the 2-fold rotation axis parallel to the b-axis.

Atomic coordinates, isotropic and anisotropic displacement parameters of all the non-hydrogen atoms were refined by means of a full matrix least-squares procedure on F$^2$. The H-atoms were included in the refinement in calculated positions riding on the atoms to which they were attached, except H2A, H7A, and H8A were refined unrestrained. The Flack parameter, x=−0.024(15). The refinement converged at R1=0.0213, wR2=0.0496, with intensity, I>2σ(I). The largest peak/hole in the final difference map was 0.879/−0.510 e/Å$^3$.

TABLE 1

| Crystal data and structure refinement for 7(Cs+). | |
|---|---|
| Identification code | v185r_0m |
| Empirical formula | C5 H25 B22 Cs N2 |
| Unit cell dimensions | a = 12.6305(8) Å   α = 90°. |
|  | b = 7.1583(4) Å    β = 91.091(1)°. |
|  | c = 12.1306(7) Å   γ = 90°. |
| Volume | 1096.56(11) Å$^3$ |
| Z | 2 |
| Density (calculated) | 1.466 Mg/m$^3$ |
| Crystal size | 0.52 × 0.10 × 0.02 mm$^3$ |
| Theta range for data collection | 1.68° to 30.03° |

The Bruker SHELXTL software package was used for phase determination and structure refinement. The distribution of intensities (E$^2$-1=0.96) and systematic absent reflections indicated one possible space group, P2(1)/c. The space group P2(1)/c (#14) was later determined to be correct. Direct methods of phase determination followed by two Fourier cycles of refinement led to an electron density map from which most of the non-hydrogen atoms were identified in the asymmetric unit of the unit cell. With subsequent isotropic refinement, all of the non-hydrogen atoms were identified. There was one anion of $[CH_{11}B_{11}]_2C3H_2N_2Li[C_4H_8O]_2$ and one cation of $Li[C_4H_8O]_4$ present in the asymmetric unit of the unit cell. One of the two THF molecules of the anion was disordered (disordered site occupancy ratio was 54%/46%). All the four THF molecules of the cation ion were disordered (disordered site occupancy ratios were 51%/49%, 54%/46%, 58%/42%, and 81%/19%,). The alert levels B, C and G reported in the checkcif are probably due to the six disordered THF molecules and the calculated H-atom positions.

Atomic coordinates, isotropic and anisotropic displacement parameters of all the non-hydrogen atoms were refined by means of a full matrix least-squares procedure on $F^2$. The H-atoms were included in the refinement in calculated positions riding on the atoms to which they were attached. The refinement converged at R1=0.0545, wR2=0.1472, with intensity I>2σ(I). The largest peak/hole in the final difference map was 0.241/−0.258 e/Å$^3$.

TABLE 2

Crystal data and structure refinement for 8.

| | |
|---|---|
| Identification code | v196_190k_0m |
| Empirical formula | C29 H72 B22 Li2 N2 O6 |
| Crystal system | Monoclinic |
| Space group | P2(1)/c |
| Unit cell dimensions | a = 14.9789(7) Å    α = 90°. |
| | b = 10.6400(5) Å    β = 96.884(1)°. |
| | c = 30.3932(15) Å   γ = 90°. |
| Volume | 4809.0(4) Å$^3$ |
| Z | 4 |
| Crystal size | 0.41 × 0.30 × 0.17 mm$^3$ |

C-2,C-5 Deprotonated Species 10.

A light brown needle-plate fragment (0.47×0.31×0.08 mm$^3$) was used for the single crystal x-ray diffraction study of $[[CH_{11}B_{11}]_4[Li(C_4H_8O)_2]_2[LiC_4H_8O]_2[C_3HN_2]_2] \cdot [Li(C_4H_8O)_4]_2$ (sample vL87_0m). The crystal was coated with paratone oil and mounted on to a cryo-loop glass fiber. X-ray intensity data were collected at 100(2) K on a Bruker APEX2 platform-CCD x-ray diffractometer system (fine focus Mo-radiation, λ=0.71073 Å, 50 KV/35 mA power). The CCD detector was placed at a distance of 5.0600 cm from the crystal.

A total of 3600 frames were collected for a sphere of reflections (with scan width of 0.3° in ω, starting ω and 2θ angles at −30°, and φ angles of 0°, 90°, 120°, 180°, 240°, and 270° for every 600 frames, 60 sec/frame exposure time). The frames were integrated using the Bruker SAINT software package and using a narrow-frame integration algorithm. Based on a monoclinic crystal system, the integrated frames yielded a total of 89375 reflections at a maximum 2θ angle of 51.36° (0.82 Å resolution), of which 19841 were independent reflections ($R_{int}$=0.0429, $R_{sig}$=0.0350, redundancy=4.5, completeness=100%) and 16453 (82.9%) reflections were greater than 2σ(I). The unit cell parameters were, a=10.1405(4) Å, b=34.3107(13) Å, c=15.0780(6) Å, 13=95.469(1)°, V=5222.2(4) Å$^3$, Z=2, calculated density $D_c$=1.112 g/cm$^3$. Absorption corrections were applied (absorption coefficient μ=0.065 mm$^{-1}$; max/min transmission=0.9950/0.9703) to the raw intensity data using the SADABS program.

The Bruker SHELXTL software package was used for phase determination and structure refinement. The distribution of intensities ($E^2$-1=0.732) and systematic absent reflections indicated two possible space groups, P2(1) and P2(1)/m. The space group P2(1) (#4) was later determined to be correct. Direct methods of phase determination followed by two Fourier cycles of refinement led to an electron density map from which most of the non-hydrogen atoms were identified in the asymmetric unit of the unit cell. With subsequent isotropic refinement, all of the non-hydrogen atoms were identified. There was one disordered anion of $[CH_{11}B_{11}]_4[Li(C_4H_8O)_2]_2[LiC_4H_8O]_2[C_3HN_2]_2$ and two disordered cations of $Li(C_4H_8O)_4$ present in the asymmetric unit of the unit cell. One of the four carboranes and four of the six THFs of the anion were modeled with disordered (carborane disordered ratio was 76%/24%, four THFs disordered ratios were 37%/36%/27%, 52%/48%, 59%/41%, and 69%/31%). Three of the four THFs of both Li-cations were modeled with disordered (THFs disordered ratios for Li5-cation were 41%/59%, 60%/40% and 66%/34%; THFs disordered ratios for Li6-cation were 53%/47%, 61%/39%, and 67%/33%). The alert levels B, C and G reported in the checkcif are probably due to the ten THFs and one carborane disorders. The space group P2(1) is chiral. Because the structure consist of only light atoms (H, Li, C, N, O) the anomalous scattering is very weak. Hence the absolute configuration cannot be determined (Flack parameter, x=−0.2(6) is meaningless) by x-ray diffraction technique using Mo-radiation.

Atomic coordinates, isotropic and anisotropic displacement parameters of all the non-hydrogen atoms were refined by means of a full matrix least-squares procedure on $F^2$. The H-atoms were included in the refinement in calculated positions riding on the atoms to which they were attached. The refinement converged at R1=0.0615, wR2=0.1483, with intensity I>2σ(I). The largest peak/hole in the final difference map was 0.414/−0.170 e/Å$^3$.

TABLE 3

Crystal data and structure refinement for dicarbene 10.

| | |
|---|---|
| Identification code | v187_0m |
| Empirical formula | C66 H158 B44 Li6 N4 O14 |
| Crystal system | Monoclinic |
| Space group | P2(1) |
| Unit cell dimensions | a = 10.1405(4) Å    α = 90°. |
| | b = 34.3107(13) Å   β = 95.469(1)°. |
| | c = 15.0780(6) Å    γ = 90°. |
| Volume | 5222.2(4) Å$^3$ |
| Z | 2 |

Example 4. Preparation of Carborane-NHC Magnesium Compositions

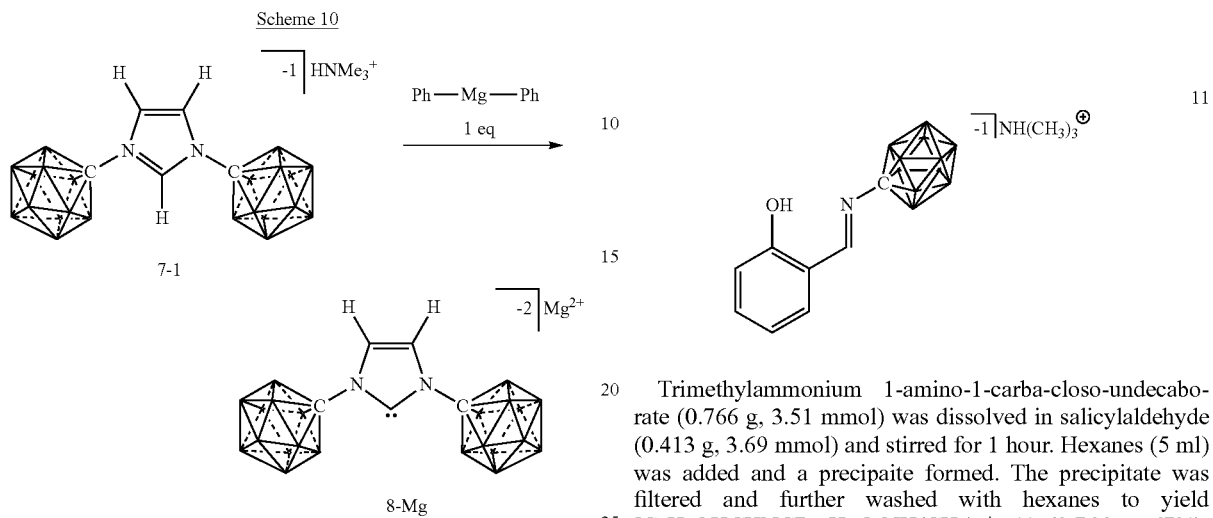

Scheme 10

Synthesis of Normal Mg$^{+2}$NHC 8-Mg.

A vial with a stir bar was loaded with 435.0 mg (1.06 mmol) of imidazolium salt 7-1 and 1.0 equivalent of diphenyl magnesium (MgPh$_2$). THF (10 mL) was subsequently added and the vial was capped and the mixture stirred for 1 hour. Removal of the volatiles under high vacuum and subsequent washing of the residue with benzene (3×5 mL) afforded 8-1 in 98% yield. $^1$H NMR (500 MHz, THF-d$_8$, 25° C.): δ=6.94 (s, 2H), 2.53-0.71 (bm, 22H, B—H).

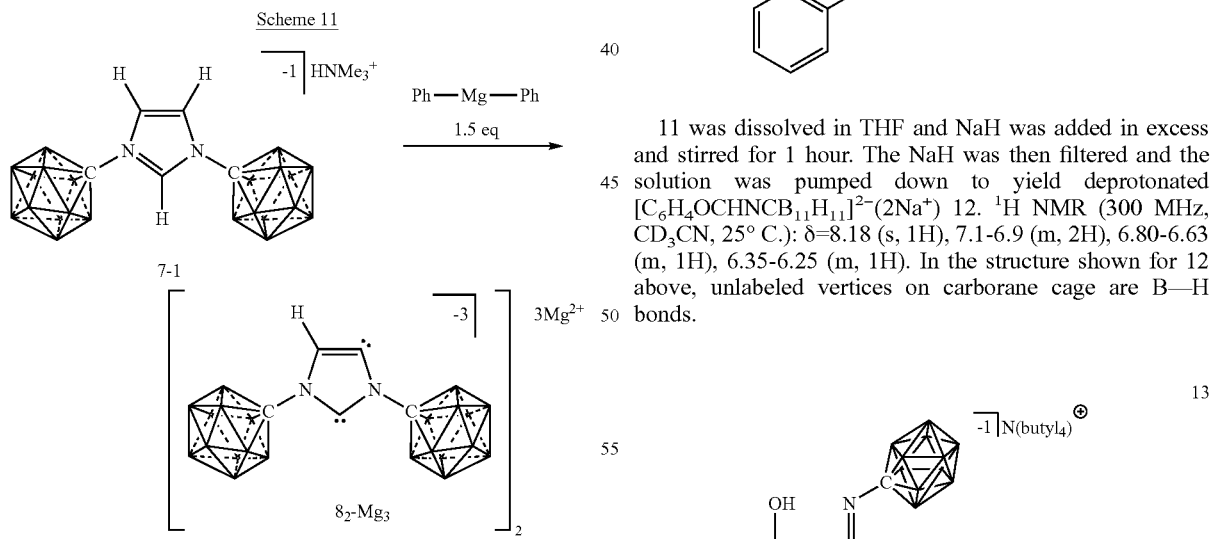

Scheme 11

Synthesis of C-2/C-5 Deprotonated Mg$^{+2}$NHC 8$_2$-Mg$_3$.

A vial with a stir bar was loaded with 435.0 mg (1.06 mmol) of imidazolium salt 7-1 and 1.5 equivalent of diphenyl magnesium (MgPh$_2$). THF (10 mL) was subsequently added and the vial was capped and the mixture stirred for 24 hours. Removal of the volatiles under high vacuum and subsequent washing of the residue with benzene (3×5 mL) afforded 8$_2$-Mg$_3$ in 98% yield. $^1$H NMR (500 MHz, THF-d$_8$, 25° C.): δ=6.43 (s, 2H), 2.56-0.69 (bm, 22H, B—H).

Example 5. Synthesis of Carborane Imines and Carborane Diimines

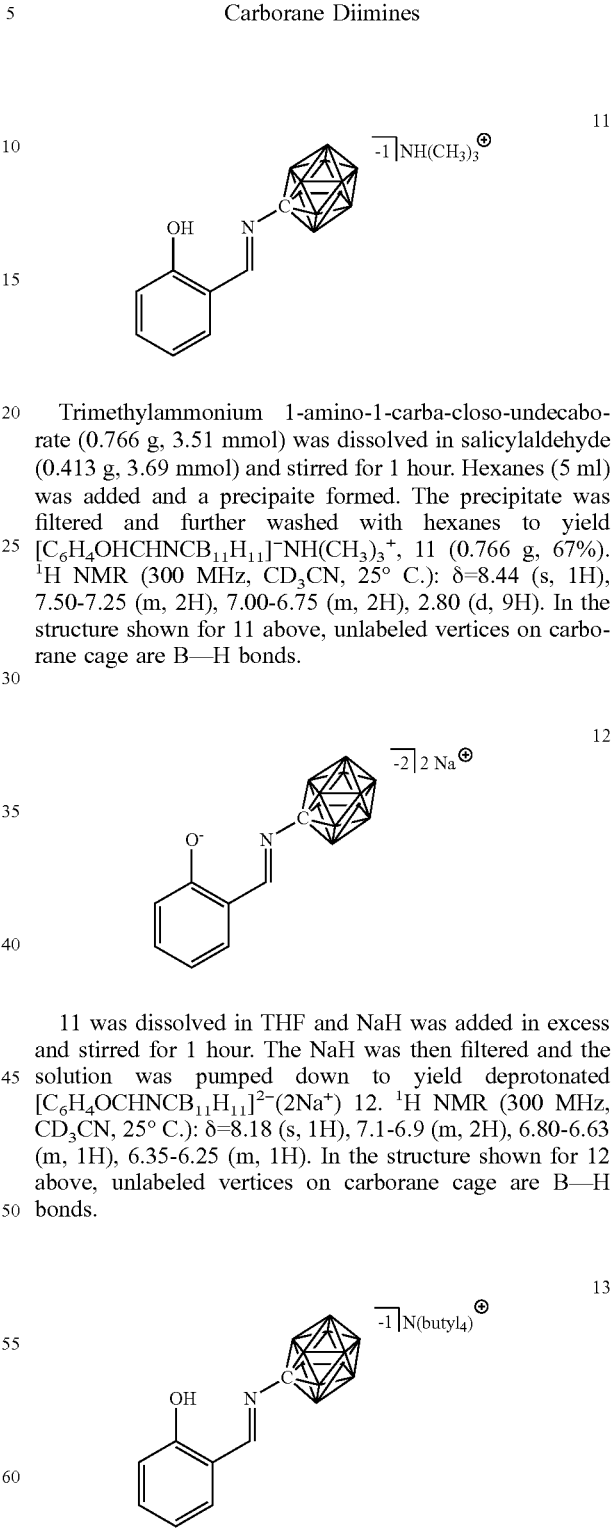

Trimethylammonium 1-amino-1-carba-closo-undecaborate (0.766 g, 3.51 mmol) was dissolved in salicylaldehyde (0.413 g, 3.69 mmol) and stirred for 1 hour. Hexanes (5 ml) was added and a precipaite formed. The precipitate was filtered and further washed with hexanes to yield [C$_6$H$_4$OHCHNCB$_{11}$H$_{11}$]$^-$NH(CH$_3$)$_3^+$, 11 (0.766 g, 67%). $^1$H NMR (300 MHz, CD$_3$CN, 25° C.): δ=8.44 (s, 1H), 7.50-7.25 (m, 2H), 7.00-6.75 (m, 2H), 2.80 (d, 9H). In the structure shown for 11 above, unlabeled vertices on carborane cage are B—H bonds.

11 was dissolved in THF and NaH was added in excess and stirred for 1 hour. The NaH was then filtered and the solution was pumped down to yield deprotonated [C$_6$H$_4$OCHNCB$_{11}$H$_{11}$]$^{2-}$(2Na$^+$) 12. $^1$H NMR (300 MHz, CD$_3$CN, 25° C.): δ=8.18 (s, 1H), 7.1-6.9 (m, 2H), 6.80-6.63 (m, 1H), 6.35-6.25 (m, 1H). In the structure shown for 12 above, unlabeled vertices on carborane cage are B—H bonds.

11 was dissolved in THF and excess tetrabutylammnoium chloride was added. After 5 minutes of stirring, the tetrabutylammonium chloride was filtered off and the resulting solution was removed to yield 13 [C$_6$H$_4$OHCHNCB$_{11}$H$_{11}$]$^-$ N(butyl$_4$)$^+$. $^1$H NMR (300 MHz, CD$_3$CN, 25° C.): δ=8.15 (s, 1H), 7.13-7.07 (m, 2H), 6.53-6.50 (m, 1H), 6.35-6.30 (m, 1H). In the structure shown for 13 above, unlabeled vertices on carborane cage are B—H bonds.

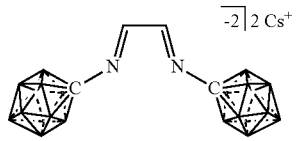

6

To a solution of CsNH$_2$CB$_{11}$H$_{11}$ (1115 mg, 3.83 mmol) was added glyoxal aqueous solution (40% w/w, 290 mg, 1.9 mmol) and the reaction mixture was allowed to stir for 3 hours. Volatiles were removed under reduced pressure and the material was used in the next step without further purification. Diimine 6 was obtained as a light brown-beige colored powder (1120 mg, 98% yield). $^1$H NMR (300 MHz, acetone-d6, 25° C.): δ=7.73 (s, 2H). In the structure shown for 6 above, unlabeled vertices on carborane cage are B—H bonds.

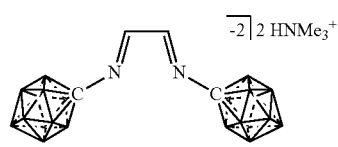

15

Me3NHCl was added to 14 and a light-brown powder precipitated out and was filtered using a fitted funnel. Finally, the powder was dried under high vacuum to obtain product 15 in a high yield (740 mg, 90%). $^1$H NMR (300 MHz, acetone-d$_6$, 25° C.): δ=8.50 (t, $^4$J(H,H)=1.74 Hz, 1H), 7.64 (d, $^4$J(H,H)=1.74 Hz, 12H), 3.20 (s, 9H). In the structure shown for 15 above, unlabeled vertices on carborane cage are B—H bonds.

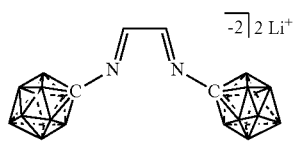

16

15 was dissolved in dry tetrahydrofuran and an excess of lithium hydride was added. After 30 minutes of stirring, the reaction solution was filtered and the solution was pumped down to yield 16. $^1$H NMR (300 MHz, acetone-d$_6$, 25° C.): δ=7.64 (s, 2H). In the structure shown for 16 above, unlabeled vertices on carborane cage are B—H bonds.

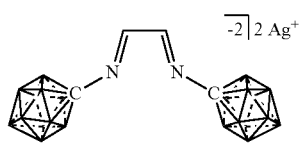

17

16 (70 mg, 0.0982 mmol) was dissolved in tetrahydrofuran. Two equivalents of silver tetrafluoroborate (40 mg, 0.196 mmol) was dissolved in tetrahydrofuran and added to the solution of 16. After one hour of stirring, the solution was filtered and tetrahydrofuran was vacuumed off. The precipitate was washed with ether to yield 17. $^1$H NMR (300 MHz, THF-d$_8$, 25° C.): δ=7.99 (s, 2H). In the structure shown for 17 above, unlabeled vertices on carborane cage are B—H bonds.

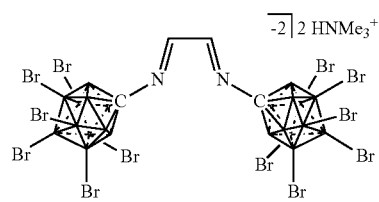

18

Hexa-brominated trimethylammonium 1-amino-1-carba-closo-undecaborate (2630 mg, 3.803 mmol) was dissolved in tetrahydrofuran and glyoxal (0.22 mL, 1.917 mmol) was added. The reaction was refluxed at 75° C. for 48 hours. The solvent was removed under reduced pressure, yielding 18. $^1$H NMR (300 MHz, THF-d$_8$, 25° C.): δ=7.99 (s, 2H). In the structure shown for 18 above, each unlabeled vertex in the carborane cage is a boron atom and each unsubstituted, unlabeled vertex in the carborane cage represents a B—H bond.

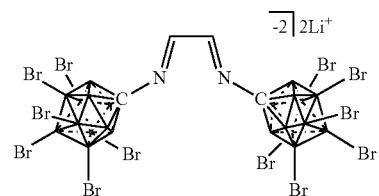

19

18 was dissolved in dry tetrahydrofuran and an excess of lithium hydride was added. After 30 minutes of stirring, the reaction solution was filtered and the solution was pumped down to yield 19. $^1$H NMR (300 MHz, THF-d$_8$, 25° C.): δ=7.85 (s, 2H). In the structure shown for 19 above, each unlabeled vertex in the carborane cage is a boron atom and each unsubstituted, unlabeled vertex in the carborane cage represents a B—H bond.

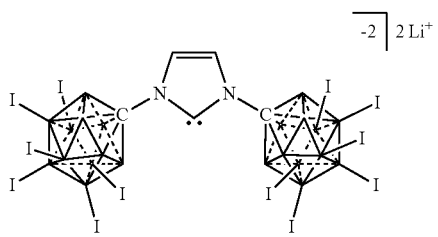

20

Hexa-iodinated trimethylammonium 1-amino-1-carba-closo-undecaborate (1480 mg, 0.923 mmol) was dissolved in tetrahydrofuran and glyoxal (0.05 mL, 0.436 mmol) was added. The reaction was refluxed at 75° C. for 48 hours.

Additional glyoxal (0.20 mL, 1.744 mmol) was added to the solution, and reaction was refluxed at 75° C. for an additional 12 hours. The solvent was removed under reduced pressure. The collected precipitate was dissolved in dry tetrahydrofuran and an excess of lithium hydride was added. After 30 minutes of stirring, the reaction solution was filtered and the solution was pumped down to yield 20. $^1$H NMR (300 MHz, THF-d$_8$, 25° C.): δ=7.70 (s, 2H). In the structure shown for 20 above, each unlabeled vertex in the carborane cage is a boron atom and each unsubstituted, unlabeled vertex in the carborane cage represents a B—H bond.

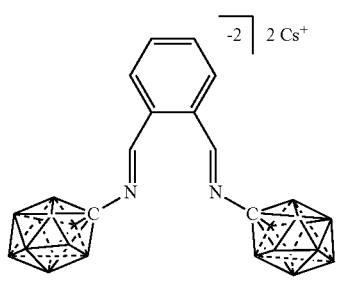

21

To a solution of cesium 1-amino-1-carba-closo-undecaborate (500 mg, 1.72 mmol) in tetrahydrofuran was added o-phthaldehyde (115 mg, 0.86 mmol) and the reaction mixture was allowed to stir for 24 hours. The solvent was removed under reduced pressure, yielding 21. $^1$H NMR (300 MHz, acetone-d6, 25° C.): δ=8.95 (s, 2H), 7.80-7.76 (m, 2H), 7.44-7.40 (m, 2H). In the structure shown for 21 above, unlabeled vertices on carborane cage are B—H bonds.

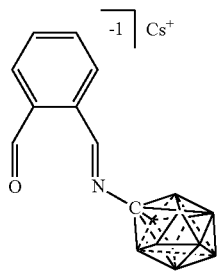

22

Cesium 1-amino-1-carba-closo-undecaborate (100 mg, 0.344 mmol) was dissolved in H$_2$O and placed in an ice bath solution while stirring. O-phthaldehyde (46 mg, 0.344 mmol) was dissolved in a second solution of H$_2$O and cooled in the ice bath. The aqueous solution of CsNH$_2$CB$_{11}$H$_{11}$ was added to the solution of o-phthaldehyde in the ice bath while stirring. Within five minutes, a light yellow precipitate formed and was filtered from the solution, yielding 22. $^1$H NMR (300 MHz, CD$_3$CN, 25° C.): δ=10.22 (s, 1H), 8.95 (s, 1H), 7.80-7.70 (m, 2H), 7.63-7.59 (m, 2H). In the structure shown for 11 above, unlabeled vertices on carborane cage are B—H bonds.

Example 6. Synthesis of Carborane Imidazoliums

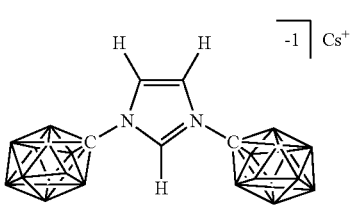

7

A solution of HCl/dioxane (4 M, 0.75 mL) was added to paraformaldehyde (68 mg, 2.2 mmol) and stirred for 20 min., then the mixture was added to an EtOAc (0.5 M, 4 mL) solution of the carborane diimine 14 (1.9 mmol) and the reaction mixture was stirred for 3 hours. $^1$H NMR (500 MHz, acetone-d6, 25° C.): δ=8.36 (t, 1H), 7.41 (d, 2H). In the structure shown for 7 above, unlabeled vertices on carborane cage are B—H bonds.

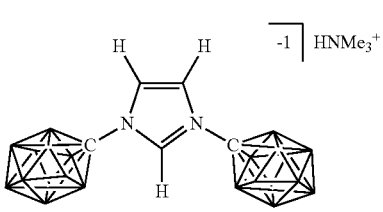

7-1

Me$_3$NHCl was added to 7 and a light-brown powder precipitated out and was filtered using a fitted funnel. Finally, the powder was dried under high vacuum to obtain product 7-1 in a high yield (740 mg, 90%). 1H NMR (300 MHz, acetone-d6, 25° C.): δ=8.36 (t, 1H), 7.41 (d, 2H). In the structure shown for 7 above, unlabeled vertices on carborane cage are B—H bonds.

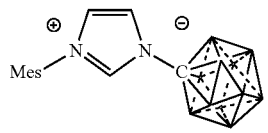

23

A Teflon stoppered Schlenk was equipped with a stir bar and loaded with 1-mesityl-3-acetoxyoxazolinium tetrafluoroborate 23a (1.515 g, 4.52 mmol) and cesium 1-amino-1-carba-closo-undecaborate (1.45 g, 4.97 mmol). Dry acetonitrile (4 mL) was added to the schlenk which was tightly sealed and heated to 70° C. for 24 hours. To the crude reaction mixture tetrafluoroboric acid diethyl ether complex (1.35 mL, 1.61 mmol) was added. The Schlenk was sealed and heated to 110° C. for 24 hours. The solution was cooled then poured into a beaker containing sodium bicarbonate (200 mL). Methylene chloride (200 mL) was added and the aqueous phase was further washed with methylene chloride (2×100 ml). The organic phase was collected, washed with brine (300 ml) and dried over magnesium sulfate. All volatiles were subsequently removed under vacuum to give a brown solid. This solid was crystallized from a concentrated acetonitrile solution at 5° C. to give 23 as light colorless blocks. Further concentration of the supernatant led to two further crops of crystals (1.14 g, 77%). 1H NMR (500 MHz, acetonitrile-d3, 25° C.): δ=8.76 (dd, 4 J(H,H) =2.0, 1.8 Hz, 1H), 7.73 (dd, 3 J(H,H)=2.0 Hz, 4 J(H,H)=1.8 Hz, 1H), 7.34 (dd, 4 J(H,H)=2.0 Hz, 3 J(H,H)=2.0 Hz, 1H), 7.09 (s, 2H), 2.34 (s, 3H), 1.98 (s, 6H), 2.72-1.22 (bm, 11H, BH). 1H[11B] NMR (192.5 MHz, acetonitrile-d3, 25° C.): δ=8.76 (1H), 7.73 (1H), 7.34 (1H), 7.09 (2H), 2.34 (3H), 1.98 (6H), 2.14 (5H), 1.68 (6H). In the structure shown for 25 above, unlabeled vertices on carborane cage are B—H bonds.

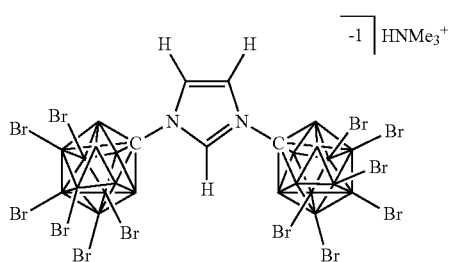

24

Starting from H11 imidazolium salt 7, Br$_2$ (4 ml) and triflic acid (2 ml) added and stirred at 50° C. for 3 days. Excess bromine removed by rotovap. Compound dissolved in acetone and removed by rotovap. Water and HNMe3$^+$ were added and stirred overnight. Solid compound 24 was collected on a frit and washed with water to remove excess HNMe3$^+$. $^1$H NMR (300 MHz, acetone-d6, 25° C.): δ=9.51 (t, 1H), 7.99 (d, 2H). In the structure shown for 24 above, each unlabeled vertex in the carborane cage is a boron atom and each unsubstituted, unlabeled vertex in the carborane cage represents a B—H bond.

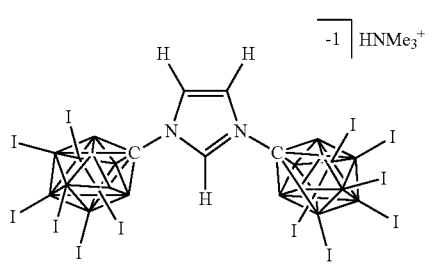

25

300 mg of H11 imidazolium salt 7, 3 g ICl, and 2 mL of triflic acid mixed together in a RBF. Reaction heated to 60° C. with a needle and septum on the reaction. This mixture was heated for 4 days. Reaction was filtered. Solid washed with dichloromethane. Solid dissolved in ethyl acetate. Ethyl acetate was washed with 5 mL of 10% sodium sulfite. Solution then was twice with 5 ml water and once with 5 mL brine. Solvent then removed by rotovap. 100 mL water added and excess trimethyl ammonium added. Solution stirred overnight and collected on a frit. $^1$H NMR (300 MHz, acetone-d6, 25° C.): δ=9.72 (t, 1H), 8.02 (d, 2H). In the structure shown for 25 above, each unlabeled vertex in the carborane cage is a boron atom and each unsubstituted, unlabeled vertex in the carborane cage represents a B—H bond.

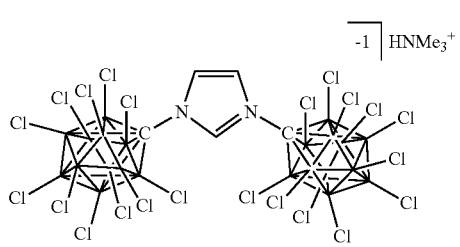

26

To 500 mg of imidazolium salt 7 was added 10 mL of antimony pentachloride. The reaction mixture was heated to reflux for 10 days under an argon atmosphere. Excess antimony pentachloride removed under vacuum. 100 mL 10% NaOH added to the reaction mixture and passed through celite. Reaction vessile then washed with 100 mL of acetone and passed over the same celite filter. Acetone then removed, 200 mL water added and solid collected on a medium porosity frit. Collected solid then added to 100 mL of water and excess trimethyl ammonium HCl added and stirred overnight and collected on a frit. Compound then washed with water to remove excess salt. $^1$H NMR (300 MHz, acetone-d6, 25° C.): δ=10.54 (t, 1H), 8.96 (d, 2H). In the structure shown for 26 above, each unlabeled vertex in the carborane cage is a boron atom.

Example 7. Synthesis of Carborane Carbenes

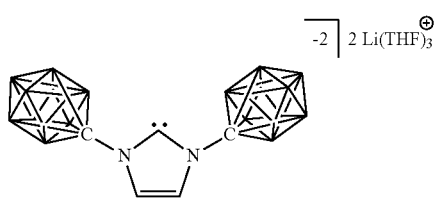

8

A THF (2 mL) solution of 7 (205.4 mg, 0.5 mmol) was treated with LiHMDS (167.33 mg, 1 mmol) and stirred for 1 hour, then volatiles were evaporated and the product was washed with benzene or diethyl ether and then with hexanes, and the product was quantitavely obtained as a light brown powder. $^1$H NMR (500 MHz, THF-d$_8$, 25° C.): δ=6.91 (s, 2H). In the structure shown for 8 above, unlabeled vertices on carborane cage are B—H bonds.

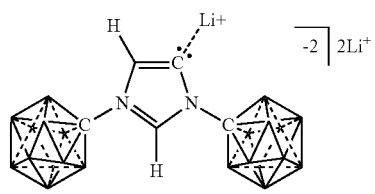

9

Two Schlenks containing stir bars were loaded with with 435.0 mg (1.06 mmol) of imidazolium salt 7 and 227.1 mg (2.12 mmol) of LDA, respectively. To each Schlenk was added 10 mL of rigorously dried THF to dissolve the base and imidazolium salt and both solutions were cooled to −78° C. The solution of imidazolium salt 7 was quickly drawn up into a syringe and added dropwise to the vigorously stirred solution of LDA. The mixture was stirred for 2 hours, and the volatiles were subsequently removed by applying a vacuum S14 immediately after removing the Schlenk from the −78° C. bath. The residue was washed at 0° C. with ether (3 mL) and dried to afford 9 as an off-white solid in approximately 97% yield (893.0 mg, 1.03 mmol) $^1$H NMR (500 MHz, THF-d8, 25° C.): δ=8.24 (d, 1H), 6.29 (d, 1H). In the structure shown for 9 above, unlabeled vertices on carborane cage are B—H bonds.

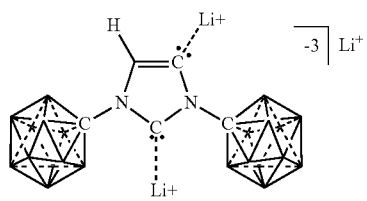

10

N-BuLi (2.5 M, in hexane, 1.23 mL, 3.18 mmol) was added to a vial and placed under vacuum for 30 minutes to remove the hexane solvent. The n-BuLi was redissolved in diethyl ether (20 mL) and added to a separate vial containing 7 (435.0 mg, 1.06 mmol). The mixture was stirred vigorously and an oil formed over ten minutes. Continued stirring of the mixture for 4 hours resulted in the oil becoming a solid precipitate. The precipitate was collected by filtration and dried under high vacuum to afford 10 in 95% yield (596.0 mg, 1.00 mmol). $^1$H NMR (400 MHz, THF-d8, 25° C.): δ=6.21 (s, 1H). In the structure shown for 10 above, unlabeled vertices on carborane cage are B—H bonds.

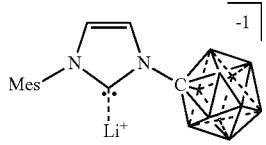

27

A glass scintillation vial equipped with a stir bar was loaded with 23 (60.0 mg, 0.18 mmol) and lithium hexamethyldisilazide (61.2 mg, 0.37 mmol). THF (1.2 mL) was added to the stirring mixture and allowed to react for one hour. After an hour a yellow-brown precipitate formed and the supernate was carefully removed. The solid was subsequently washed with ether (3×3 mL) and dried in vacuo to furnish the desired compound, 27 (78.0 mg, 76%). 1H NMR (300 MHz, THF-d8, 25° C.): δ=7.40 (d, 3 J(H,H)=1.5 Hz, 1H), 6.98 (s, 2H), 6.79 (d, 3 J(H,H)=1.5 Hz, 1H), 2.30 (s, 3H), 1.95 (s, 6H). In the structure shown for 27 above, unlabeled vertices on carborane cage are B—H bonds.

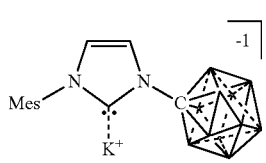

28

A vial was equipped with a stir bar and loaded with 23 (1.23 g, 3.75 mmol) and KHMDS (0.63 g, 5.61 mmol). THF (5 mL) was added to dissolve the stirring solids. After 1 h the mixture was filtered and crystallized by adding diethyl ether (2 mL). Light brown cubes of 28 formed at −30° C. $^1$H NMR (400 MHz, THF-d8, 25° C.): δ=7.35 (d, 1H), 6.96 (s, 2H), 6.70 (d, 1H), 2.29 (s, 3H), 1.94 (s, 6H). In the structure shown for 33 above, unlabeled vertices on carborane cage are B—H bonds.

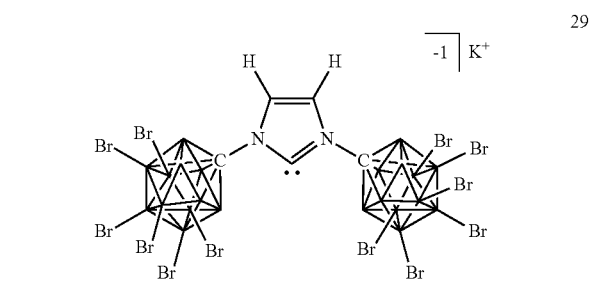

29

Reaction of imidazolium salt 24 with 2 equivalents of potassium tertbutoxide in THF. Solution then concentrated and added dropwise to a stirring solution of diethyly ether. $^1$H NMR (300 MHz, THF-d8, 25° C.): δ=7.02 (s, 2H). In the structure shown for 29 above, each unlabeled vertex in the carborane cage is a boron atom and each unsubstituted, unlabeled vertex in the carborane cage represents a B—H bond.

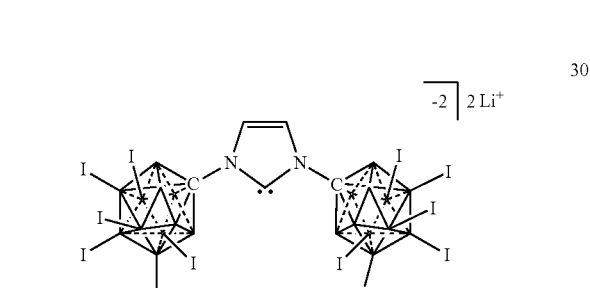

30

380 mg of I12 imidazolium trimethyl ammonium salt 25 dissolved in 15 ml THF. 0.0788 g of LiHMDS added and stirred for 30 mins. Solution concentrated by vacuum. THF solution then added dropwise to a stirring diethyl ether solution. Precipitate 30 was then collected and dried by vacuum. $^1$H NMR (300 MHz, THF-d8, 25° C.): δ=7.10 (s, 2H). In the structure shown for 30 above, each unlabeled vertex in the carborane cage is a boron atom and each unsubstituted, unlabeled vertex in the carborane cage represents a B—H bond.

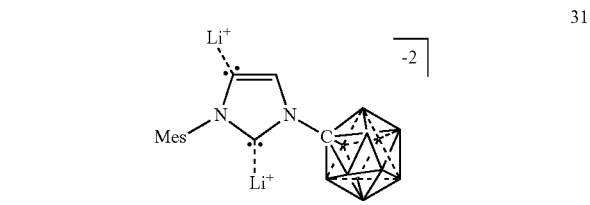

31

To a glass vial equipped with a stir bar was loaded with 23 (296.3 mg, 0.90 mmol) and diethyl ether (17 mL). Next, n-butyllithium (1.80 mmol) in ether (2 ml) was added to the stirring suspension of 23. Following the addition of the n-butyllithium an oil began to form along the walls of the vial. The reaction mixture was vigorously stirred and scraped with a spatula periodically over an hour until a yellow solid precipitated from the lime-green solution. The reaction was stirred for another hour and then filtered and washed with diethyl ether. The product, 31, was collected as a yellow solid (487.4 mg, 96%). $^1$H NMR (400 MHz, THF-d8, 25° C.): δ=6.84 (s, 2H), 6.58 (s, 1H), 2.25 (s, 3H), 1.92 (s, 6H). In the structure shown for 36 above, unlabeled vertices on carborane cage are B—H bonds.

Example 8. Synthesis of Metal Complexes with Carborane-Based Ligands

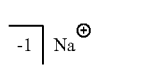

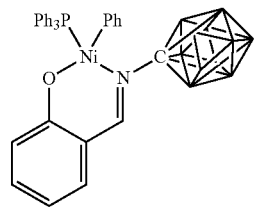

Imine 12 (54 mg, 0.1034 mmol) was dissolved in THF and Ni(PPh$_3$)$_2$PhCl (72 mg, 0.134 mmol) was added. After stirring for 30 minutes, the red solution was vacuumed off and the precipitate 32 was washed with hexanes. $^{31}$P (121 MHz, F—C$_6$H$_5$, 25° C.): δ=25.00. In the structure shown for 32 above, unlabeled vertices on carborane cage are B—H bonds.

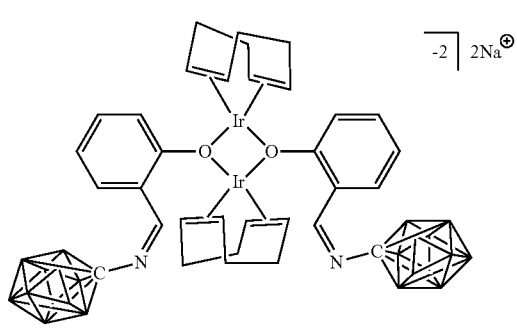

Imine 12 (76 mg, 0.188 mmol) was dissolved in THF and added to a solution of Bis(1,5-cyclooctadiene)diiridium(I) dichloride (65 mg, 0.188 mmol) in THF. After 1 hr, THF was vacuumed off and the precipitate was washed with hexanes. $^1$H NMR (300 MHz, CD$_3$CN, 25° C.): δ=12.77 (s, 2H). In the structure shown for 33 above, unlabeled vertices on carborane cage are B—H bonds.

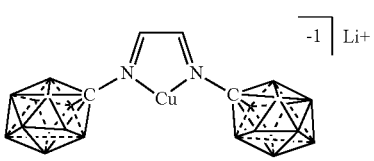

Diimine 16 (86 mg, 0.119 mmol) was dissolved in tetrahydrofuran, and one equivalent of copper (I) chloride (12 mg, 0.119 mmol) was added. After three hours of stirring, the solution was filtered and tetrahydrofuran was vacuumed off, yielding 34. $^1$H NMR (300 MHz, THF-d$_8$, 25° C.): δ=7.85 (s, 2H). In the structure shown for 34 above, unlabeled vertices on carborane cage are B—H bonds.

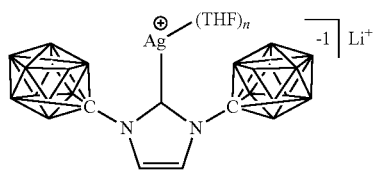

A scintillation vial was equipped with a stir bar was loaded with compound 8 (250 mg, 314 µmol) and dissolved in 1 mL of THF and gently stirred. Next silver tetrafluoroborate (67.2 mg, 345 µmol) was dissolved in THF (1 mL) and added to the vial containing compound 8 and stirred for 15 minutes. After 15 minutes the compound was pipette filtered (glass fiber 2 µm) then added drop wise to 15 mL of vigorously stirring hexane. The hexane was stirred for another ten minutes before being decanted off. The wash was performed once more and the compound dried on the high vacuum for 2 hours. In the structure shown for 35 above, unlabeled vertices on carborane cage are B—H bonds.

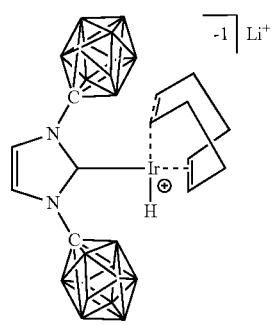

A scintillation vial was equip with a stir bar and loaded with silver tetrafluoroborate (11.6 mg, 59.6 µmol), Bis(1,5-cyclooctadiene)diiridium(I) dichloride (20 mg, 29.8 µmol) and dissolved in 2 mL of THF. To the gently stirring solution compound 8 (39.9 mg, 59.6 µmol) was added and the resulting dark solution stirred for 12 hours and then filtered (glass fiber 2 µm). The filtrate was added to a vigorously stirring solution of hexane (15 mL) for ten minutes at which point the hexane was decanted and solid pumped down. $^1$H NMR (300 MHz, THF-d8, 25° C.): δ=7.21 (d, 3J(H,H)=1.0 Hz, 1H), 7.10 (d, 3J(H,H)=1.0 Hz, 1H), 5.1 (s, 4H), 2.0 (m, 8H), 1.2 to 2.7 (bm, 21H, B—H), −6.3 (bs, 1H, agnostic), −13.4 (s, 1H, Ir—H). In the structure shown for 36 above, unlabeled vertices on carborane cage are B—H bonds.

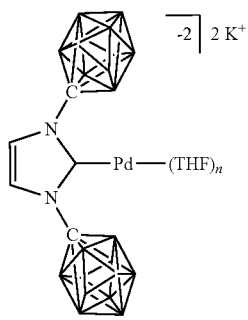

37

A glass scintillation vial was loaded with (COD)Pd(TMS)2 (10 mg, 25.7 mmol), compound 7 (10.5 mg, 25.4 mmol), and potassium tert-butoxide (5.9 mg, 52.2 mmol). The solids were dissolved in acetonitrile and hand swirled for two minutes. After two minutes the acetonitrile suspension was added to vigorously stirring diethyl ether. After 15 minutes the ether was decanted and product dried on the high vacuum thus furnishing compound 37. 1H NMR (300 MHz, THF-d8, 25° C.): 7.12 (s, 2H), 1.32 (s, 2H), 0.12 (s, 9H).

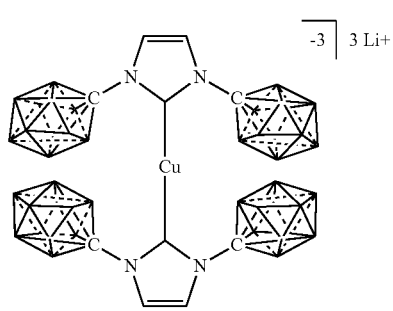

38

In a glove box under dinitrogen atmosphere compound 8 (40 mg, 50 μmol) was loaded in to a scintillation vial equip with a stir bar and copper(I) chloride (2.5 mg, 25 μmol). The solids were dissolved in THF and stirred vigorously for 24 hours in lue of slight darkening of the suspension. After 24 hours the suspension was filtered and solvents removed to furnish compound 38. $^1$H NMR (300 MHz, THF-d$_8$, 25° C.): δ=7.1 (s, 4H).

Example 9. Carborane NHC-Catalyzed C—H Activation

Scheme 12

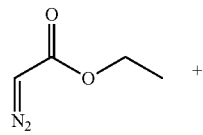

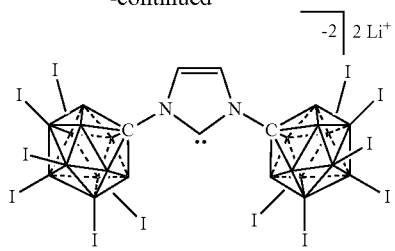

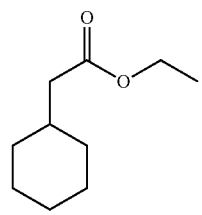

4.0% Catalyst Loading.

The catalyst shown in Scheme 12 was prepared from 1 equivalent CuCl$_2$ and 3 equivalents of hexa iodinated carborane NHC in tetrahydrofuran. The solution was stirred for 6 hours, filtered, and the solvent was removed under reduced pressure. The precipitate (28 mg, 0.0122 mmol) was directly added to 20 mL of cyclohexane, and heated to 90° C. under argon. Once the reaction reached reflux, 20 mL of cyclohexane containing ethyl diazoacetate (32 μL, 0.304 mmol) was added via syringe pump over 3 hours. $^1$H NMR analysis of the reaction solution revealed 74% conversion of ethyl diazoacetate to the expected insertion product ethyl 2-cyclohexylacetate (87.7%), in addition to dimer side products (12.3%), diethyl maleate and diethyl fumarate. TON=16.0, TOF=5.3 per hour Scheme 13

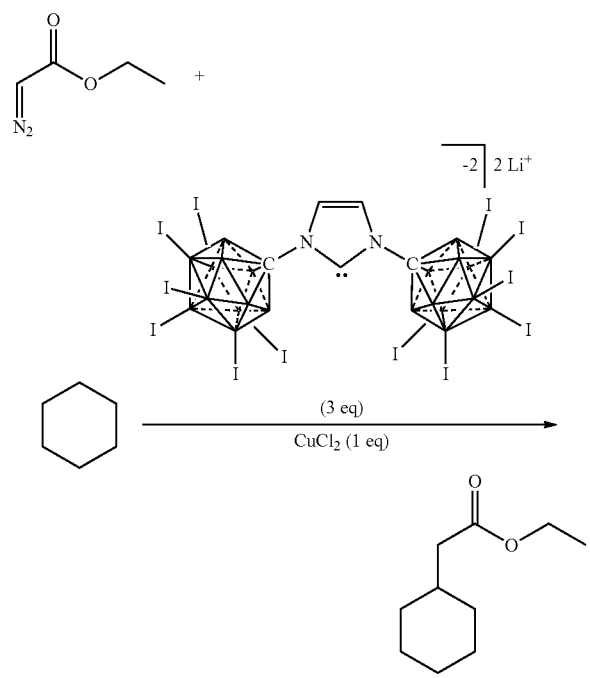

1.0% Catalyst Loading.

The precipitate (17 mg, 0.0072 mmol), prepared as described above, was directly added to 5 mL of cyclohexane, and heated to 90° C. under argon. Once the reaction reached reflux, 20 mL of cyclohexane containing ethyl diazoacetate (75 µL, 0.72 mmol) was added via syringe pump over 3 hours. See, Scheme 13. $^1$H NMR analysis of the reaction solution revealed full conversion of ethyl diazoacetate to the expected insertion product ethyl 2-cyclohexylacetate (52.3%), in addition to dimer side products (47.7%), diethyl maleate and diethyl fumarate. TON=52.0, TOF=17.3 per hour

Scheme 14

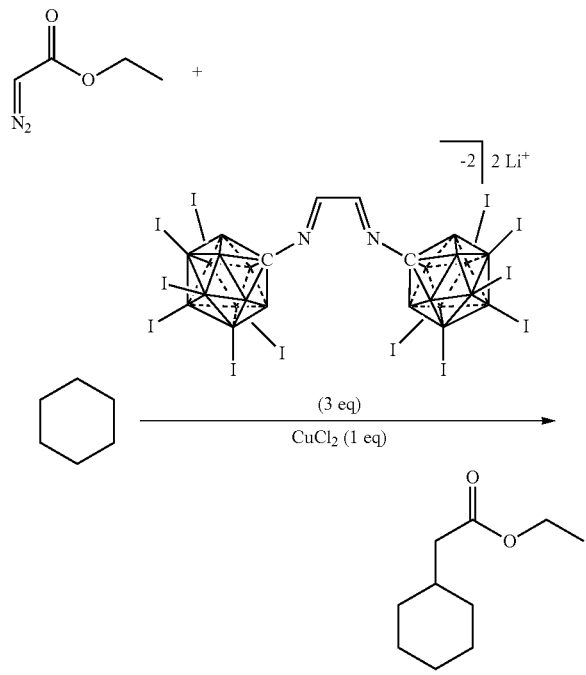

4.6% Catalyst Loading.

The catalyst shown in Scheme 14 was prepared from 1 equivalent CuCl$_2$ and 3 equivalents of the diimine I12 in tetrahydrofuran. The solution was stirred for 6 hours, and the solvent was removed under reduced pressure. The precipitate (71 mg, 0.0355 mmol) was directly added to 20 mL of cyclohexane, and heated to 90° C. under argon. Once the reaction reached reflux, 20 mL of cyclohexane containing ethyl diazoacetate (82 µL, 0.773 mmol) was added via syringe pump over 3 hours. $^1$H NMR analysis of the reaction solution revealed full conversion of ethyl diazoacetate to the expected insertion product ethyl 2-cyclohexylacetate (87.7%), in addition to dimer side products (12.3%), diethyl maleate and diethyl fumarate. TON=19.1, TOF=6.3 per hour

Scheme 15

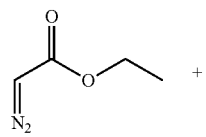

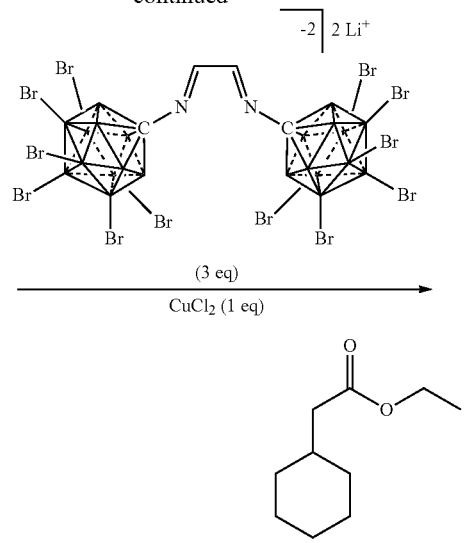

4.6% Catalyst Loading.

The catalyst shown in Scheme 15 was prepared from 1 equivalent CuCl$_2$ and 3 equivalents of the diimine Br12 in tetrahydrofuran. The solution was stirred for 6 hours, and the solvent was removed under reduced pressure. The precipitate (42 mg, 0.029 mmol) was directly added to 20 mL of cyclohexane, and heated to 90° C. under argon. Once the reaction reached reflux, 20 mL of cyclohexane containing ethyl diazoacetate (67 µL, 0.637 mmol) was added via syringe pump over 3 hours. $^1$H NMR analysis of the reaction solution revealed full conversion of ethyl diazoacetate to the expected insertion product ethyl 2-cyclohexylacetate (92.6%), in addition to dimer side products (7.4%), diethyl maleate and diethyl fumarate. TON=20.3, TOF=6.8 per hour

Scheme 16

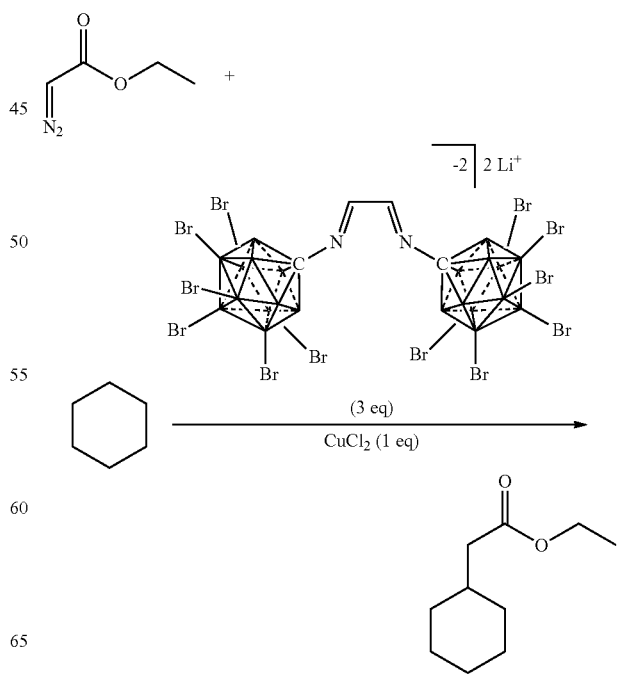

0.1% Catalyst Loading.

The precipitate (0.96 mg, 0.00066 mmol) was added to a schlenk tube from a stock solution prepared in THF. The solvent was removed from the schlenk under reduced pressure, and 20 mL of cyclohexane was added, forming a suspension with the precipitate. The schlenk tube was heated to 90° C. under argon. Once the reaction reached reflux, 20 mL of cyclohexane containing ethyl diazoacetate (69.7 µL, 0.662 mmol) was added via syringe pump over 3 hours. See, Scheme 16. The reaction progress was checked after 3 hours, and $^1$H NMR analysis of the reaction solution revealed 32% of ethyl diazoacetate was not yet converted (Of the converted ethyldiazoacetate, 58.5% was ethyl 2-cyclohexylacetate and 41.5% was dimer side products). The reaction was heated at reflux for an addition 3 hours, and $^1$H NMR analysis showed full conversion of ethyl diazoacetate to the expected insertion product ethyl 2-cyclohexylacetate (56.2%), in addition to dimer side products (43.8%), diethyl maleate and diethyl fumarate. TON=563, TOF=94 per hour (6 hours).

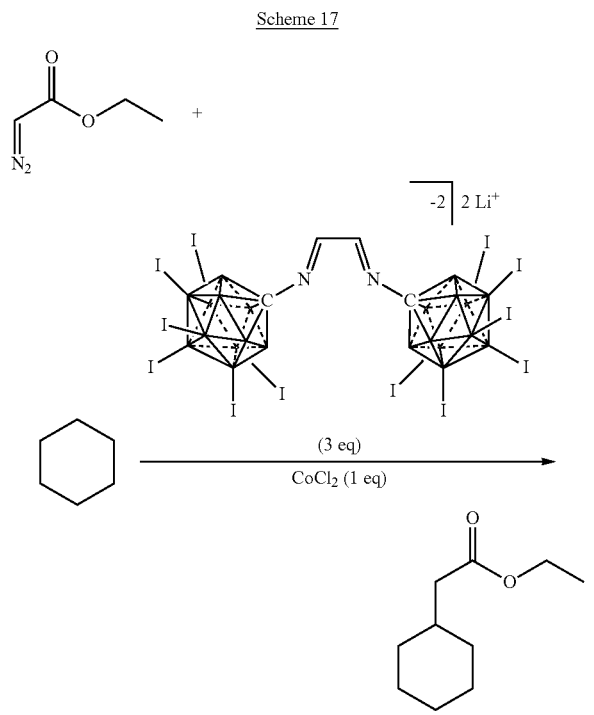

Scheme 17

4.6% Catalyst Loading.

The catalyst shown in Scheme 17 was prepared from 1 equivalent CoCl$_2$ and 3 equivalents of the diimine I12 in tetrahydrofuran. The solution was stirred for 6 hours, and the solvent was removed under reduced pressure. The precipitate (10 mg, 0.0082 mmol) was directly added to 20 mL of cyclohexane, and heated to 90° C. under argon. Once the reaction reached reflux, 20 mL of cyclohexane containing ethyl diazoacetate (16 µL, 0.176 mmol) was added via liquid addition funnel over 3 hours. $^1$H NMR analysis of the reaction solution revealed 85% conversion of ethyl diazoacetate to the expected insertion product ethyl 2-cyclohexylacetate (49.5%), in addition to dimer side products (50.5%), diethyl maleate and diethyl fumarate. TON=9.03, TOF=3.01.

Example 10. Caborane-NHC Battery Electrolytes

The Mg complexes 8-Mg and 8$_2$-Mg (Example 4) were screened for their suitability as Mg battery electrolytes via cyclic voltammetry experiments. Electrochemical Mg deposition/stripping was observed (overpotential 0.1 V) via cyclic voltammetry with a three-electrode cell using a standard Pt working electrode and Mg metal strip reference electrode. The concentration of the electrolytes was 0.25 M dissolved in dimethoxy ethane and the a constant scan rate of 25 mV/s. The anodic stability of both electrolyte formulations was +3.0 V vs Mg$^{0/+2}$.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:
1. A carborane compound according to Formula 1:

wherein:
Het$^N$ is an N-heterocyclic carbene (NHC) moiety;
R$^B$ is a carba-closo-dodecaborate substituent;
R$^W$ is selected from the group consisting of R$^B$, H, halogen, alkyl, aryl, silyl, siloxy, alkoxy, and aryloxy, wherein R$^B$, alkyl, aryl, silyl, siloxy, alkoxy, and aryloxy in R$^W$ are optionally substituted with at least one member independently selected from the group consisting of halogen, hydroxyl, hydroxide, alkyl, aryl, silyl, siloxy, alkoxy, aryloxy, amino, alkylamino, arylamino, dialkylamino, diarylamino, haloalkyl, thio, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, and nitro; and
A is absent, or
A represents one or more cations, each of which is optionally coordinated by 1-8 neutral or anionic ligands.
2. The carborane compound according to claim 1, wherein alkyl, aryl, silyl, siloxy, alkoxy, and aryloxy in R$^W$ are optionally substituted with a member independently selected from the group consisting of hydrogen, halogen, hydroxyl, and hydroxide.
3. The carborane compound according to claim 1, wherein R$^W$ is selected from alkyl and aryl.
4. The carborane compound according to claim 1, the compound having a structure according to Formula 2:

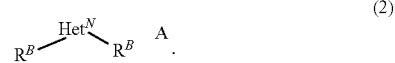

5. The carborane compound according to claim 1, wherein Het$^N$ is selected from the group consisting of:

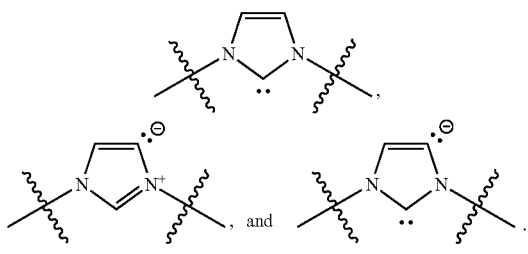
, and

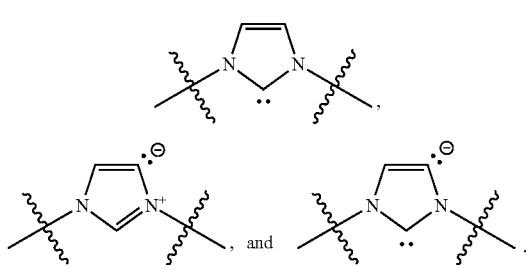
, and .

6. The carborane compound according to claim 1, wherein $R^B$ has the structure

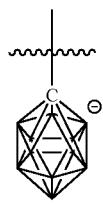

wherein each unlabeled vertex is a boron atom substituted with one $R^1$ group; and each $R^1$ is independently selected from H, halogen, hydroxyl, hydroxide, alkyl, aryl, silyl, siloxy, alkoxy, aryloxy, amino, alkylamino, arylamino, dialkylamino, diarylamino, haloalkyl, thio, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, nitro, and alkoxy, wherein each alkyl, aryl, silyl, siloxy, alkoxy, and aryloxy in $R^1$ is optionally substituted with a member independently selected from the group consisting of halogen, hydroxyl, hydroxide, alkyl, aryl, silyl, siloxy, alkoxy, aryloxy, amino, alkylamino, arylamino, dialkylamino, diarylamino, haloalkyl, thio, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, and nitro.

7. The carborane compound according to claim 6, wherein each $R^1$ is independently selected from H, halogen, alkyl, aryl, silyl, siloxy, alkoxy, and aryloxy, and wherein each alkyl, aryl, silyl, siloxy, alkoxy, and aryloxy in $R^1$ is optionally substituted with a member independently selected from the group consisting of halogen, hydroxyl, and hydroxide.

8. The carborane compound according to claim 6, wherein each $R^1$ is independently selected from the group consisting of H, alkyl, F, Cl, Br, and I.

9. The carborane compound according to claim 8, wherein five $R^1$ are H in each $R^B$ group and each of the remaining six $R^1$ groups is independently selected from the group consisting of alkyl, F, Cl, Br, and I in each $R^B$ group.

10. The carborane compound according to claim 8, wherein each of the eleven $R^1$ groups in each $R^B$ group is independently selected from the group consisting of alkyl, F, Cl, Br, and I.

11. The carborane compound according to claim 6, wherein $Het^N$ is selected from the group consisting of:

12. The carborane compound according to claim 1, wherein A is selected from the group consisting of $Li^+$, $HN(alkyl)_3^+$, $N(alkyl)_4^+$, and $Mg^{2+}$.

13. A carborane compound having a structure selected from the group consisting of Formula (I), Formula (II), Formula (III), Formula (IV), Formula (V), Formula (VI), Formula (VII), Formula (VIII), Formula (IX), Formula (X), Formula (XI), Formula (XII), Formula (XIII), Formula (XIV), Formula (XV), Formula (XVI), and Formula (XVII):

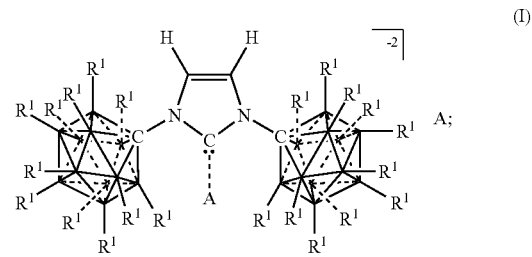
(I)

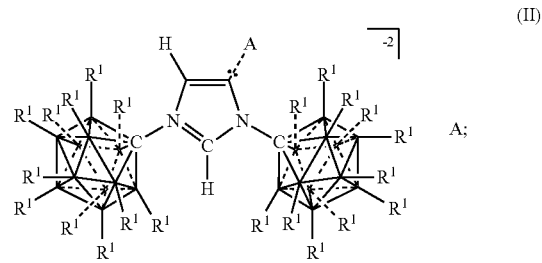
(II)

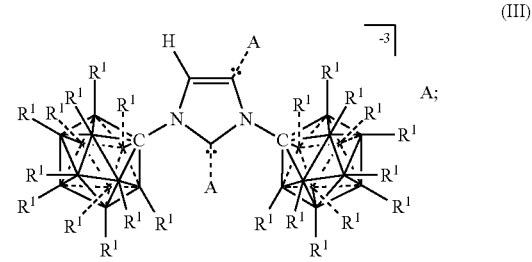
(III)

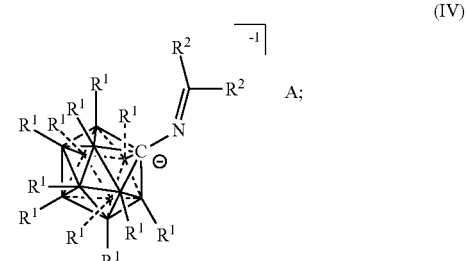
(IV)

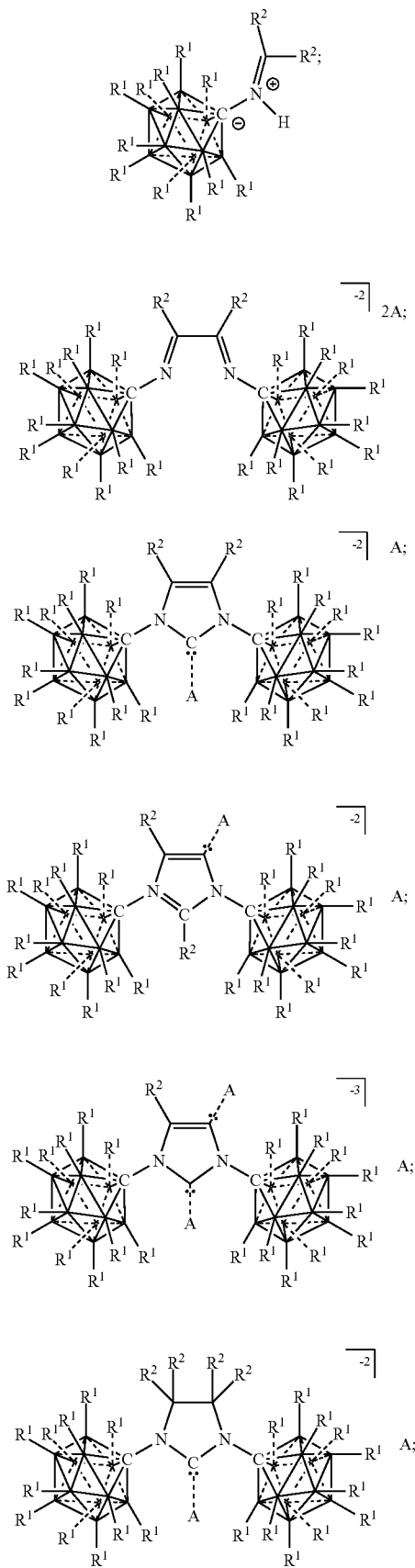
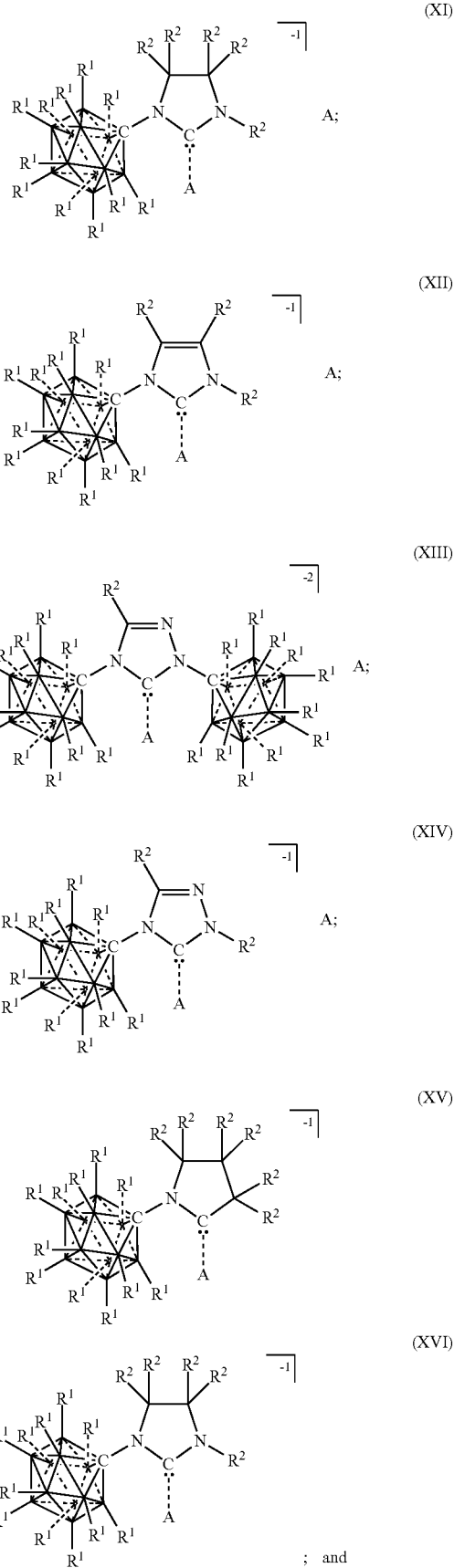

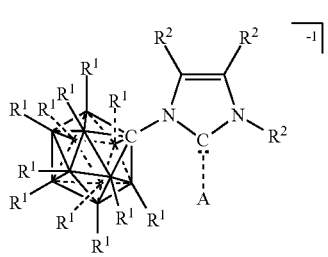

(XVII)

wherein each unlabeled vertex bonded to $R^1$ represents a boron atom, wherein each $R^1$ and each $R^2$ is independently selected from the group consisting of H, halogen, alkyl, aryl, silyl, siloxy, alkoxy, and aryloxy;

wherein each alkyl, aryl, silyl, siloxy, alkoxy, and aryloxy is optionally substituted with a member independently selected from the group consisting of halogen, hydroxyl, and hydroxide; and wherein A is a cation.

14. The carborane compound according to claim 13, having the following structure:

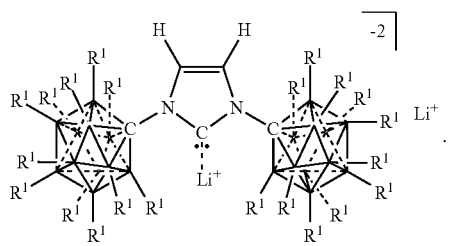

15. The carborane compound according to claim 13, having the following structure:

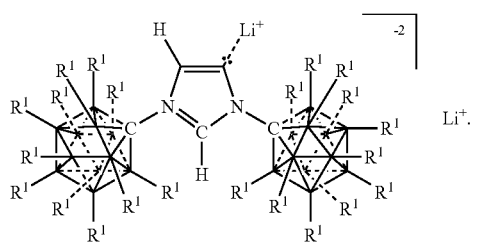

16. The carborane compound according to claim 13, having the following structure:

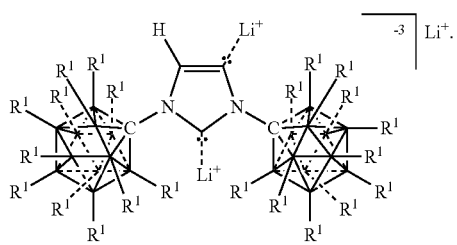

17. The carborane compound according to claim 13, having the following structure:

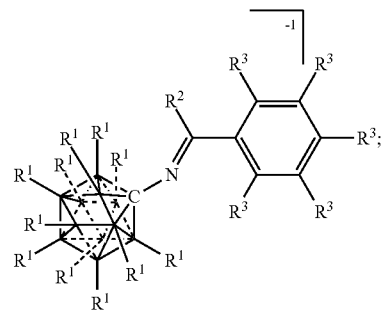

wherein each $R^3$ is independently selected from the group consisting of H, hydroxyl, hydroxide, and halogen.

18. The carborane compound according to any of claims 14-17, wherein each $R^1$ is independently selected from the group consisting of H, alkyl, F, Cl, Br, and I.

19. A carbene complex comprising a transition metal and a carborane compound according to claim 13.

20. A complex according to claim 19, wherein the transition metal is selected from the group consisting of Fe, Ru, Os, Co, Rh, Ir, Ni, Pd, Pt, Cu, Ag, and Au.

21. A method of forming a carbon-carbon bond, the method comprising forming a reaction mixture comprising a carbene complex according to claim 19, a carbene transfer agent, and a substrate having at least one carbon-hydrogen bond under conditions sufficient for the insertion of the carbene into the carbon-hydrogen bond.

22. A process for preparing a compound according to Formula (C):

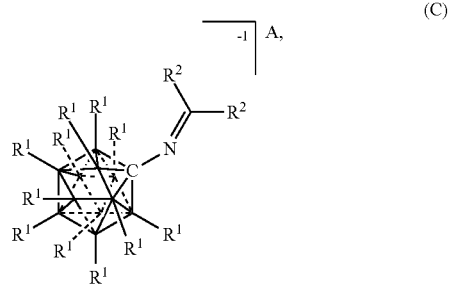

(C)

the process comprising condensing a compound according to Formula (A)

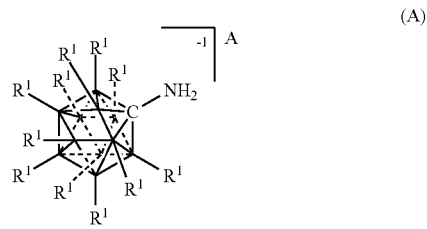

(A)

with a compound according to Formula (B)

(B)

under conditions sufficient to form the compound of Formula (C);

wherein
each unlabeled vertex bonded to $R^1$ represents a boron atom;

each $R^1$ and each $R^2$ is independently selected from the group consisting of H, halogen, hydroxyl, hydroxide, alkyl, aryl, silyl, siloxy, alkoxy, aryloxy, amino, alkylamino, arylamino, dialkylamino, diarylamino, haloalkyl, thio, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, and nitro;

each alkyl, aryl, silyl, siloxy, alkoxy, and aryloxy is optionally substituted with a member independently selected from the group consisting of phosphine, phosphite, halogen, hydroxyl, hydroxide, alkyl, aryl, silyl, siloxy, alkoxy, aryloxy, amino, alkylamino, arylamino, dialkylamino, diarylamino, haloalkyl, thio, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, and nitro; and A is a cation, which is optionally coordinated by 1-8 neutral or anionic ligands.

23. A process for preparing a compound according Formula (G),

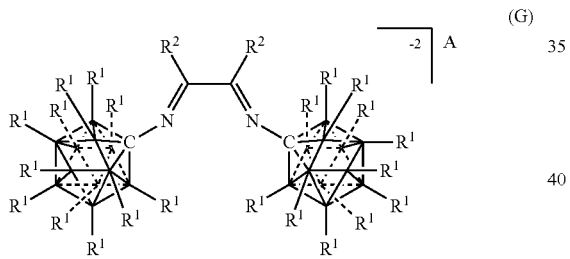

the process comprising condensing a compound according to Formula (A)

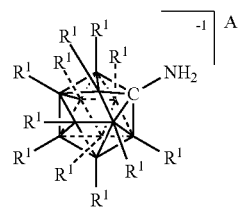

with a compound according to Formula (F):

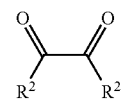

under conditions sufficient to form the compound of Formula (G) (C);
wherein
each unlabeled vertex bonded to $R^1$ represents a boron atom;

each $R^1$ and each $R^2$ is independently selected from the group consisting of H, halogen, hydroxyl, hydroxide, alkyl, aryl, silyl, siloxy, alkoxy, aryloxy, amino, alkylamino, arylamino, dialkylamino, diarylamino, haloalkyl, thio, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, and nitro;

each alkyl, aryl, silyl, siloxy, alkoxy, and aryloxy is optionally substituted with a member independently selected from the group consisting of phosphine, phosphite, halogen, hydroxyl, hydroxide, alkyl, aryl, silyl, siloxy, alkoxy, aryloxy, amino, alkylamino, arylamino, dialkylamino, diarylamino, haloalkyl, thio, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, and nitro; and A represents one or more cations, each of which is optionally coordinated by 1-8 neutral or anionic ligands.

* * * * *